United States Patent
Li et al.

(10) Patent No.: US 12,186,332 B2
(45) Date of Patent: *Jan. 7, 2025

(54) METHODS FOR OVERCOMING WNT/BETA-CATENIN ANTI-CANCER RESISTANCE IN LEUKEMIA STEM CELLS

(71) Applicants: STOWERS INSTITUTE FOR MEDICAL RESEARCH, Kansas City, MO (US); THE CHILDREN'S MERCY HOSPITAL, Kansas City, MO (US); UNIVERSITY OF KANSAS, Lawrence, KS (US)

(72) Inventors: Linheng Li, Kansas City, MO (US); John M. Perry, Olathe, KS (US); Fang Tao, Overland Park, KS (US); Xi C. He, Kansas City, MO (US); Anuradha Roy, Kansas City, MO (US); Scott J. Weir, Overland Park, KS (US); Tara Lin, Mission Hills, KS (US)

(73) Assignees: Stowers Institute for Medical Research, Kansas City, KS (US); The Children's Mercy Hospital, Kansas City, KS (US); University of Kansas, Lawrence, KS (US)

( * ) Notice: Subject to any disclaimer, the term of this patent is extended or adjusted under 35 U.S.C. 154(b) by 421 days.

This patent is subject to a terminal disclaimer.

(21) Appl. No.: 16/914,086

(22) Filed: Jun. 26, 2020

(65) Prior Publication Data
US 2021/0113597 A1    Apr. 22, 2021

Related U.S. Application Data

(60) Provisional application No. 62/867,780, filed on Jun. 27, 2019.

(51) Int. Cl.
| | | |
|---|---|---|
| *A61K 31/704* | (2006.01) | |
| *A61K 39/395* | (2006.01) | |
| *A61P 35/02* | (2006.01) | |
| *C07K 16/28* | (2006.01) | |

(52) U.S. Cl.
CPC ........ *A61K 31/704* (2013.01); *A61K 39/3955* (2013.01); *A61P 35/02* (2018.01); *C07K 16/2818* (2013.01)

(58) Field of Classification Search
None
See application file for complete search history.

(56) References Cited

U.S. PATENT DOCUMENTS

| 11,173,173 | B2* | 11/2021 | Kasi ........................ A61K 45/06 |
|---|---|---|---|
| 2003/0194400 | A1* | 10/2003 | Liu ........................ C07K 14/745 |
| | | | 424/178.1 |
| 2008/0221146 | A1* | 9/2008 | Mahadevan ............. A61P 35/04 |
| | | | 435/375 |
| 2015/0272992 | A1* | 10/2015 | Prockop ................... A61P 35/00 |
| | | | 424/93.7 |
| 2017/0129904 | A1* | 5/2017 | Park ....................... A61K 31/352 |
| 2018/0022700 | A1* | 1/2018 | Ran .......................... A61P 35/00 |
| | | | 514/34 |
| 2018/0207184 | A1* | 7/2018 | Kasi ........................ A61K 45/06 |
| 2019/0038645 | A1* | 2/2019 | Asai ...................... A61K 31/704 |
| 2019/0269629 | A1* | 9/2019 | Podestá .................. A61K 31/15 |
| 2020/0171165 | A1* | 6/2020 | Schnitzer ................ A61P 35/00 |
| 2021/0113597 | A1* | 4/2021 | Li .......................... A61K 31/704 |
| 2022/0105114 | A1* | 4/2022 | Kasi ...................... A61K 9/5138 |

OTHER PUBLICATIONS

Hsu et al. (2015) Oncotarget 6(42): 44134-44150.*
Kwak et al. (2017) Journal of Controlled Release 267: 203-213.*
Manso et al. (2013) Clin Transl Oncol 15: 467-471.*
Rahman et al. (1986) Cancer Chemother Pharmacol 16: 22-27.*
Doxorubicin Hydrochloride Label/Package Insert, 2013, 26 pages.*
Doxorubicin Hydrochloride Label/Package Insert, 2019, 26 pages.*
Daunorubicin Label (Hikma Pharmaceuticals USA Inc, revised May 2015); 10 pages.*
Xu, C. et al. beta-Catenin/POU5F1/SOX2 transcription factor complex mediates IGF-I receptor signaling and predicts poor prognosis in lung adenocarcinoma. Cancer Res 73, 3181-3189 (2013).
Cancer Genome Atlas Research, N. et al. Integrated genomic characterization of endometrial carcinoma. Nature 497, 67-73 (2013).
Guezguez, B. et al. GSK3 Deficiencies in Hematopoietic Stem Cells Initiate Pre-neoplastic State that Is Predictive of Clinical Outcomes of Human Acute Leukemia. Cancer Cell 29, 61-74 (2016).
Al-Dhfyan, A., Alhoshani, A. & Korashy, H. M. Aryl hydrocarbon receptor/cytochrome P450 1A1 pathway mediates breast cancer stem cells expansion through PTEN inhibition and beta-Catenin and Akt activation. Mol Cancer 16, 14 (2017).
Brown, J. B. et al. Epithelial phosphatidylinositol-3-kinase signaling is required for beta-catenin activation and host defense against Citrobacter rodentium infection. Infect Immun 79, 1863-1872 (2011).
Lee, G. et al. Phosphoinositide 3-kinase signaling mediates beta-catenin activation in intestinal epithelial stem and progenitor cells in colitis. Gastroenterology 139, 869-881, 881 e861-869 (2010).
Sharma, P., Hu-Lieskovan, S., Wargo, J. A. & Ribas, A. Primary, Adaptive, and Acquired Resistance to Cancer Immunotherapy. Cell 168, 707-723 (2017).
Spranger, S., Bao, R. & Gajewski, T. F. Melanoma-intrinsic beta-catenin signalling prevents anti-tumour immunity. Nature 523, 231-235 (2015).
Spranger, S. & Gajewski, T. F. Impact of oncogenic pathways on evasion of antitumour immune responses. Nat Rev Cancer 18, 139-147 (2018).

(Continued)

*Primary Examiner* — Ilia I Ouspenski

(74) *Attorney, Agent, or Firm* — Bryan Cave Leighton Paisner LLP

(57) ABSTRACT

The present disclosure provides, inter alia, methods for treating cancers including leukemia using low doses of an anthracycline such as doxorubicin.

10 Claims, 73 Drawing Sheets

Specification includes a Sequence Listing.

(56) References Cited

OTHER PUBLICATIONS

Galluzzi, L., Buque, A., Kepp, 0., Zitvogel, L. & Kroemer, G. Immunological Effects of Conventional Chemotherapy and Targeted Anticancer Agents. Cancer Cell 28, 690-714 (2015).
Casares, N. et al. Caspase-dependent immunogenicity of doxorubicin-induced tumor cell death. J Exp Med 202, 1691-1701 (2005).
Rabbani, A., Finn, R. M. & Ausio, J. The anthracycline antibiotics: antitumor drugs that alter chromatin structure. Bioessays 27, 50-56 (2005).
Gewirtz, D. A. A critical evaluation of the mechanisms of action proposed for the antitumor effects of the anthracycline antibiotics adriamycin and daunorubicin. Biochem Pharmacol 57, 727-741 (1999).
Gothert, J. R. et al. In vivo fate-tracing studies using the Scl stem cell enhancer: embryonic hematopoietic stem cells significantly contribute to adult hematopoiesis. Blood 105, 2724-2732 (2005).
Barker, N. & Clevers, H. Catenins, Wnt signaling and cancer. Bioessays 22, 961-965 (2000).
Hsu, J. M. et al. STT3-dependent PD-L1 accumulation on cancer stem cells promotes immune evasion. Nature communications 9, 1908 (2018).
Malta, T. M. et al. Machine Learning Identifies Stemness Features Associated with Oncogenic Dedifferentiation. Cell 173, 338-354 e315 (2018).
Jinesh, G. G., Manyam, G. C., Mmeje, C. 0., Baggerly, K. A. & Kamat, A. M. Surface PD-L1, E-cadherin, CD24, and VEGFR2 as markers of epithelial cancer stem cells associated with rapid tumorigenesis. Scientific reports 7, 9602 (2017).
Chen, G. Y., Tang, J., Zheng, P. & Liu, Y. CD24 and Siglec-10 selectively repress tissue damage-induced immune responses. Science 323, 1722-1725 (2009).
Tran, T. H. et al. Long circulating self-assembled nanoparticles from cholesterol-containing brush-like block copolymers for improved drug delivery to tumors. Biomacromolecules 15, 4363-4375 (2014).
Hong, D. et al. Initiating and cancer-propagating cells in TEL-AML 1-associated childhood leukemia. Science 319, 336-339 (2008).
Castor, A. et al. Distinct patterns of hematopoietic stem cell involvement in acute lymphoblastic leukemia. Nat Med 11, 630-637 (2005).
Kong, Y. et al. CD34+CD38+CD19+ as well as CD34+CD38−CD19+ cells are leukemia-initiating cells with self-renewal capacity in human B-precursor ALL. Leukemia 22, 1207-1213 (2008).
Wilson, K. et al. Flow minimal residual disease monitoring of candidate leukemic stem cells defined by the immunophenotype, CD34+CD38lowCD19+ in B-lineage childhood acute lymphoblastic leukemia. Haematologica 95, 679-683 (2010).
Eguchi, M., Eguchi-Ishimae, M. & Ishii, E. [Recent progress in leukemic stem cell research for childhood leukemia]. Rinsho Ketsueki 56, 1871-1881 (2015).
Kikushige, Y. et al. TIM-3 is a promising target to selectively kill acute myeloid leukemia stem cells. Cell Stem Cell 7, 708-717 (2010).
Jan, M. et al. Prospective separation of normal and leukemic stem cells based on differential expression of TIM3, a human acute myeloid leukemia stem cell marker. Proc Natl Acad Sci U S A 108, 5009-5014 (2011).
Weinberg, R. A. The biology of cancer. Second edition. edn, (2014).
Nitiss, J. L. Targeting DNA topoisomerase II in cancer chemotherapy. Nat Rev Cancer 9, 338-350 (2009).
Anderson, A. C. Tim-3: an emerging target in the cancer immunotherapy landscape. Cancer Immunol Res 2, 393-398 (2014).
Anderson, A. C., Joller, N. & Kuchroo, V. K. Lag-3, Tim-3, and TIGIT: Co-inhibitory Receptors with Specialized Functions in Immune Regulation. Immunity 44, 989-1004 (2016).
Lesche, R. et al. Cre/loxP-mediated inactivation of the murine Pten tumor suppressor gene. Genesis 32, 148-149 (2002).
Harada, N. et al. Intestinal polyposis in mice with a dominant stable mutation of the beta-catenin gene. Embo J 18, 5931-5942 (1999).
Hu, Y. & Smyth, G. K. ELDA: extreme limiting dilution analysis for comparing depleted and enriched populations in stem cell and other assays. Journal of immunological methods 347, 70-78 (2009).
Freireich, E. J., Gehan, E. A., Rall, D. P., Schmidt, L. H. & Skipper, H. E. Quantitative comparison of toxicity of anticancer agents in mouse, rat, hamster, dog, monkey, and man. Cancer chemotherapy reports. Part 1 50, 219-244 (1966).
Kim, D. et al. TopHat2: accurate alignment of transcriptomes in the presence of insertions, deletions and gene fusions. Genome Biol 14, R36 (2013).
Anders, S., Pyl, P. T. & Huber, W. HTSeq—a Python framework to work with high-throughput sequencing data. Bioinformatics 31, 166-169 (2015).
Robinson, M. D., McCarthy, D. J. & Smyth, G. K. edgeR: a Bioconductor package for differential expression analysis of digital gene expression data. Bioinformatics 26, 139-140 (2010).
Miao, Y. et al. Adaptive Immune Resistance Emerges from Tumor-Initiating Stem Cells. Cell 177, 1172-1186 e1114, doi:10.1016/j.cell.2019.03.025 (2019).
Kuttesch, J. F., Jr. Multidrug resistance in pediatric oncology. Invest New Drugs 14, 55-67 (1996).
Greaves, M. & Maley, C. C. Clonal evolution in cancer. Nature 481, 306-313 (2012).
Kreso, A. & Dick, J. E. Evolution of the cancer stem cell model. Cell Stem Cell 14, 275-291 (2014).
Dick, J. E. Stem cell concepts renew cancer research. Blood 112, 4793-4807 (2008).
Eppert, K. et al. Stem cell gene expression programs influence clinical outcome in human leukemia. Nat Med 17, 1086-1093 (2011).
Greaves, M. Darwinian medicine: a case for cancer. Nat Rev Cancer 7, 213-221 (2007).
Greaves, M. Cancer stem cells renew their impact. Nat Med 17, 1046-1048 (2011).
Ding, L. et al. Clonal evolution in relapsed acute myeloid leukaemia revealed by whole-genome sequencing. Nature 481, 506-510 (2012).
Hanahan, D. & Weinberg, R. A. Hallmarks of cancer: the next generation. Cell 144, 646-674 (2011).
Holohan, C., Van Schaeybroeck, S., Longley, D. B. & Johnston, P. G. Cancer drug resistance: an evolving paradigm. Nat Rev Cancer 13, 714-726 (2013).
Cleary, M. L. Regulating the leukemia stem cell. Best practice & research. Clinical haematology 22, 483-487 (2009).
Peng, W. et al. Loss of PTEN Promotes Resistance to T Cell-Mediated Immunotherapy. Cancer discovery 6, 202-216 (2016).
Fruman, D. A. et al. The PI3K Pathway in Human Disease. Cell 170, 605-635 (2017).
Ciraolo, E., Morello, F. & Hirsch, E. Present and future of PI3K pathway inhibition in cancer: perspectives and imitations. Current medicinal chemistry 18, 2674-2685 (2011).
Cully, M., You, H., Levine, A. J. & Mak, T. W. Beyond PTEN mutations: the PI3K pathway as an integrator of multiple inputs during tumorigenesis. Nat Rev Cancer 6, 184-192 (2006).
Fruman, D. A. & Rommel, C. PI3K and cancer: lessons, challenges and opportunities. Nature reviews. Drug discovery 13, 140-156 (2014).
Hennessy, B. T., Smith, D. L., Ram, P. T., Lu, Y. & Mills, G. B. Exploiting the PI3K/AKT pathway for cancer drug discovery. Nature reviews. Drug discovery 4, 988-1004 (2005).
Koren, S. & Bentires-Alj, M. Tackling Resistance to PI3K Inhibition by Targeting the Epigenome. Cancer Cell 31, 616-618 (2017).
Thorpe, L. M., Yuzugullu, H. & Zhao, J. J. PI3K in cancer: divergent roles of isoforms, modes of activation and therapeutic targeting. Nat Rev Cancer 15, 7-24 (2014).
Gutierrez, A. et al. High frequency of PTEN, PI3K, and AKT abnormalities in T-cell acute lymphoblastic leukemia. Blood 114, 647-650 (2009).
Hogan, L. E. et al. Integrated genomic analysis of relapsed childhood acute lymphoblastic leukemia reveals therapeutic strategies. Blood 118, 5218-5226 (2011).
Bhatla, T. et al. Epigenetic reprogramming reverses the relapse-specific gene expression signature and restores chemosensitivity in childhood B-lymphoblastic leukemia. Blood 119, 5201-5210 (2012).

(56) References Cited

OTHER PUBLICATIONS

Bolouri, H. et al. The molecular landscape of pediatric acute myeloid leukemia reveals recurrent structural alterations and age-specific mutational interactions. Nat Med 24, 103-112 (2018).

Griffiths, E. A. et al. Acute myeloid leukemia is characterized by Wnt pathway inhibitor promoter hypermethylation. Leukemia & lymphoma 51, 1711-1719 (2010).

Dandekar, S. et al. Wnt inhibition leads to improved chemosensitivity in paediatric acute lymphoblastic leukaemia. Br J Haematol 167, 87-99 (2014).

Kandoth, C. et al. Mutational landscape and significance across 12 major cancer types. Nature 502, 333-339 (2013).

Huang, J., Nguyen-McCarty, M., Hexner, E. 0., Danet-Desnoyers, G. & Klein, P. S. Maintenance of hematopoietic stem cells through regulation of Wnt and mTOR pathways. Nat Med 18, 1778-1785 (2012).

Korkaya, H. et al. Regulation of mammary stem/progenitor cells by PTEN/Akt/beta-catenin signaling. PLoS Biol 7, e1000121 (2009).

Huang, J. et al. Pivotal role for glycogen synthase kinase-3 in hematopoietic stem cell homeostasis in mice. J Clin Invest 119, 3519-3529 (2009).

Conley, S. J. et al. Antiangiogenic agents increase breast cancer stem cells via the generation of tumor hypoxia. Proc Natl Acad Sci U S A 109, 2784-2789 (2012).

He, X. C. et al. PTEN-deficient intestinal stem cells initiate intestinal polyposis. Nat Genet 39, 189-198 (2007).

Perry, J. M. et al. Cooperation between both Wnt/{beta}-catenin and PTEN/PI3K/Akt signaling promotes primitive hematopoietic stem cell self-renewal and expansion. Genes Dev 25, 1928-1942 (2011).

Knapp, D. J. et al. Distinct signaling programs control human hematopoietic stem cell survival and proliferation. Blood 129, 307-318 (2017).

Shlush, L. I. et al. Identification of pre-leukaemic haematopoietic stem cells in acute leukaemia. Nature 506, 328-333 (2014).

Reya, T., Morrison, S. J., Clarke, M. F. & Weissman, I. L. Stem cells, cancer, and cancer stem cells. Nature 414, 105-111 (2001).

Nguyen, L. V., Vanner, R., Dirks, P. & Eaves, C. J. Cancer stem cells: an evolving concept. Nat Rev Cancer 12, 133-143 (2012).

Clevers, H. The cancer stem cell: premises, promises and challenges. Nat Med 17, 313-319 (2011).

Zhou, H. et al. Combined inhibition of beta-catenin and Bcr-Abl synergistically targets tyrosine kinase inhibitor-resistant plast crisis chronic myeloid leukemia blasts and progenitors in vitro and in vivo. Leukemia (2017).

Kurtova, A. V. et al. Blocking PGE-induced tumour repopulation abrogates bladder cancer chemoresistance. Nature (2014).

Heidel, F. H. et al. Genetic and pharmacologic inhibition of beta-catenin targets imatinib-resistant leukemia stem cells in CML. Cell Stem Cell 10, 412-424 (2012).

Zhao, C. et al. Loss of beta-catenin impairs the renewal of normal and CML stem cells in vivo. Cancer Cell 12, 528-541 (2007).

Toska, E. et al. PI3K pathway regulates ER-dependent transcription in breast cancer through the epigenetic regulator KMT2D. Science 355, 1324-1330 (2017).

Tenbaum, S. P. et al. beta-catenin confers resistance to PI3K and AKT inhibitors and subverts FOXO3a to promote metastasis in colon cancer. Nat Med 18, 892-901 (2012).

Kaveri, D. et al. beta-Catenin activation synergizes with Pten loss and Myc overexpression in Notch-independent T-ALL. Blood 122, 694-704 (2013).

Guo, W. et al. Multi-genetic events collaboratively contribute to Pten-null leukaemia stem-cell formation. Nature 453, 529-533 (2008).

Roderick, J. E. et al. c-Myc inhibition prevents leukemia initiation in mice and impairs the growth of relapsed and induction failure pediatric T-ALL cells. Blood 123, 1040-1050 (2014).

Schubbert, S. et al. Targeting the MYC and PI3K Pathways Eliminates Leukemia-Initiating Cells in T-cell Acute Lymphoblastic Leukemia. Cancer Res 74, 7048-7059 (2014).

Dail, M. et al. Loss of oncogenic Notch1 with resistance to a PI3K inhibitor in T-cell leukaemia. Nature 513, 512-516 (2014).

Huang, W., Chang, H. Y., Fei, T., Wu, H. & Chen, Y. G. GSK3 beta mediates suppression of cyclin D2 expression by tumor suppressor PTEN. Oncogene 26, 2471-2482 (2007).

Lechman, E. R. et al. Attenuation of miR-126 activity expands HSC in vivo without exhaustion. Cell Stem Cell 11, 799-811 (2012).

\* cited by examiner

Fig. 3B
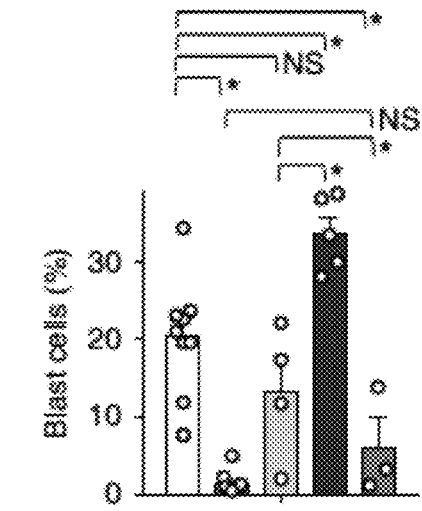
*P < 0.05
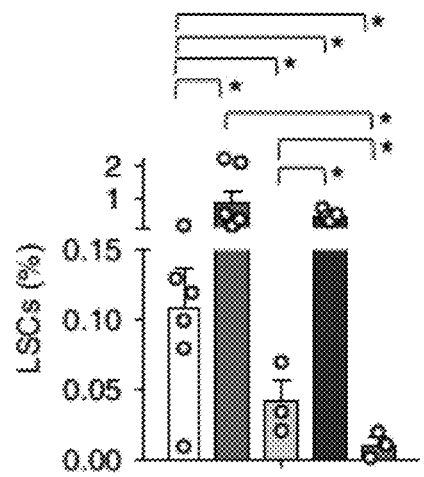
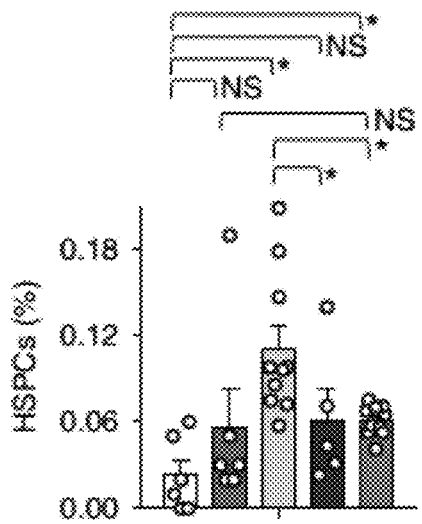
Fig. 3C
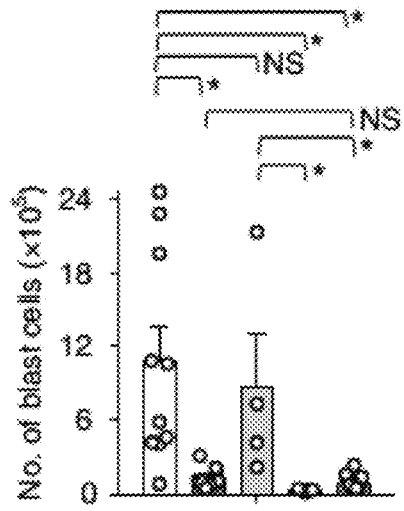
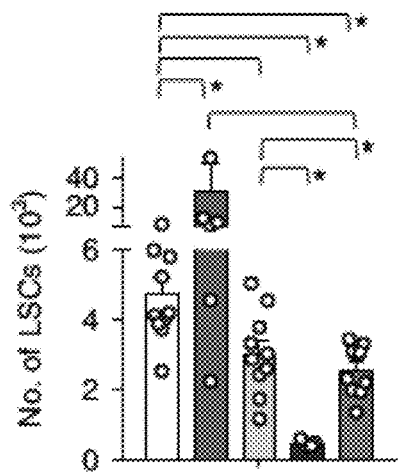
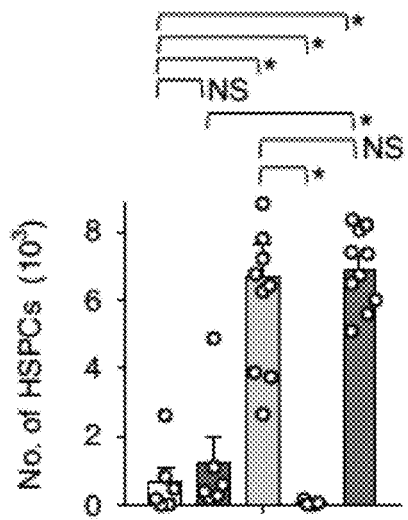

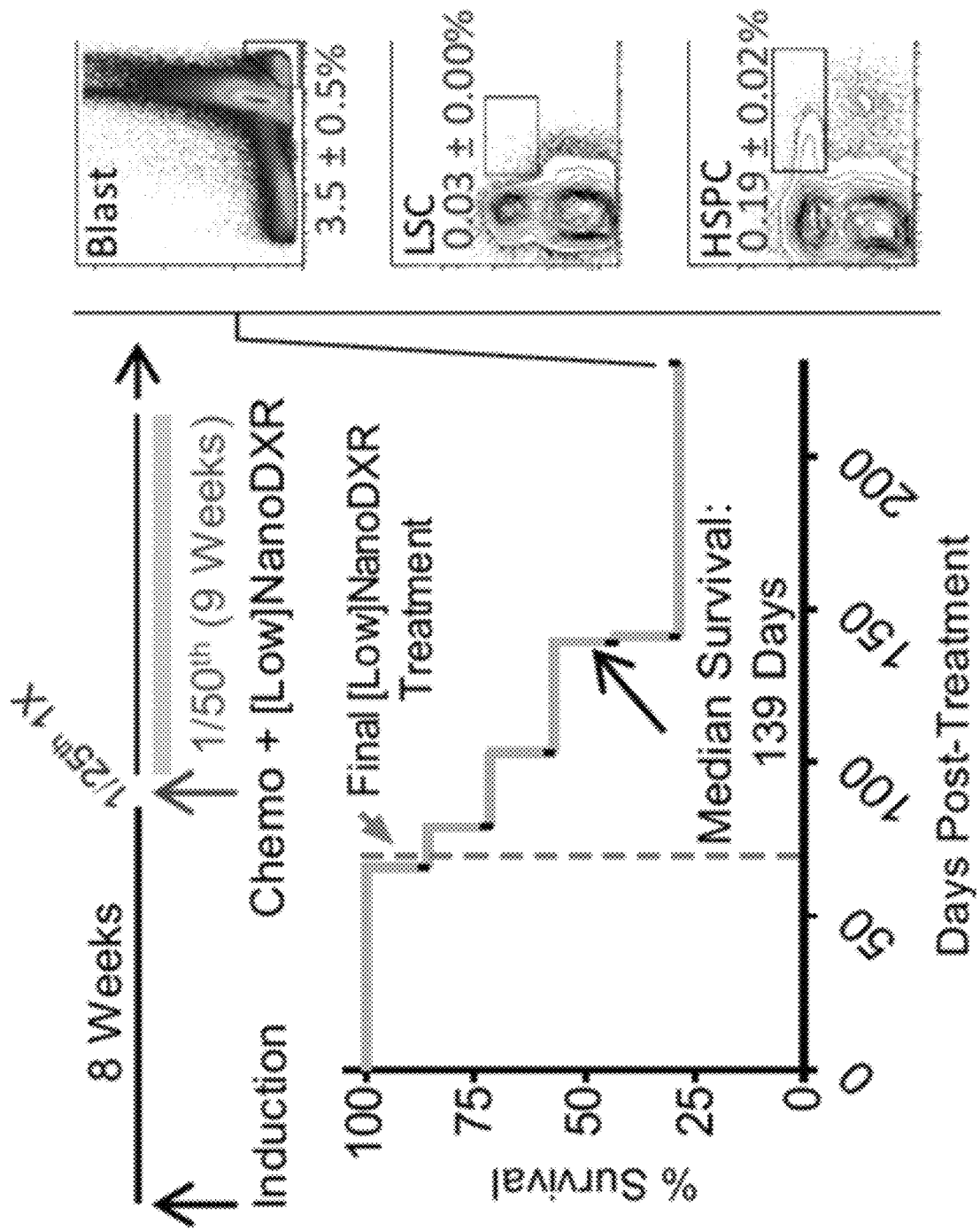

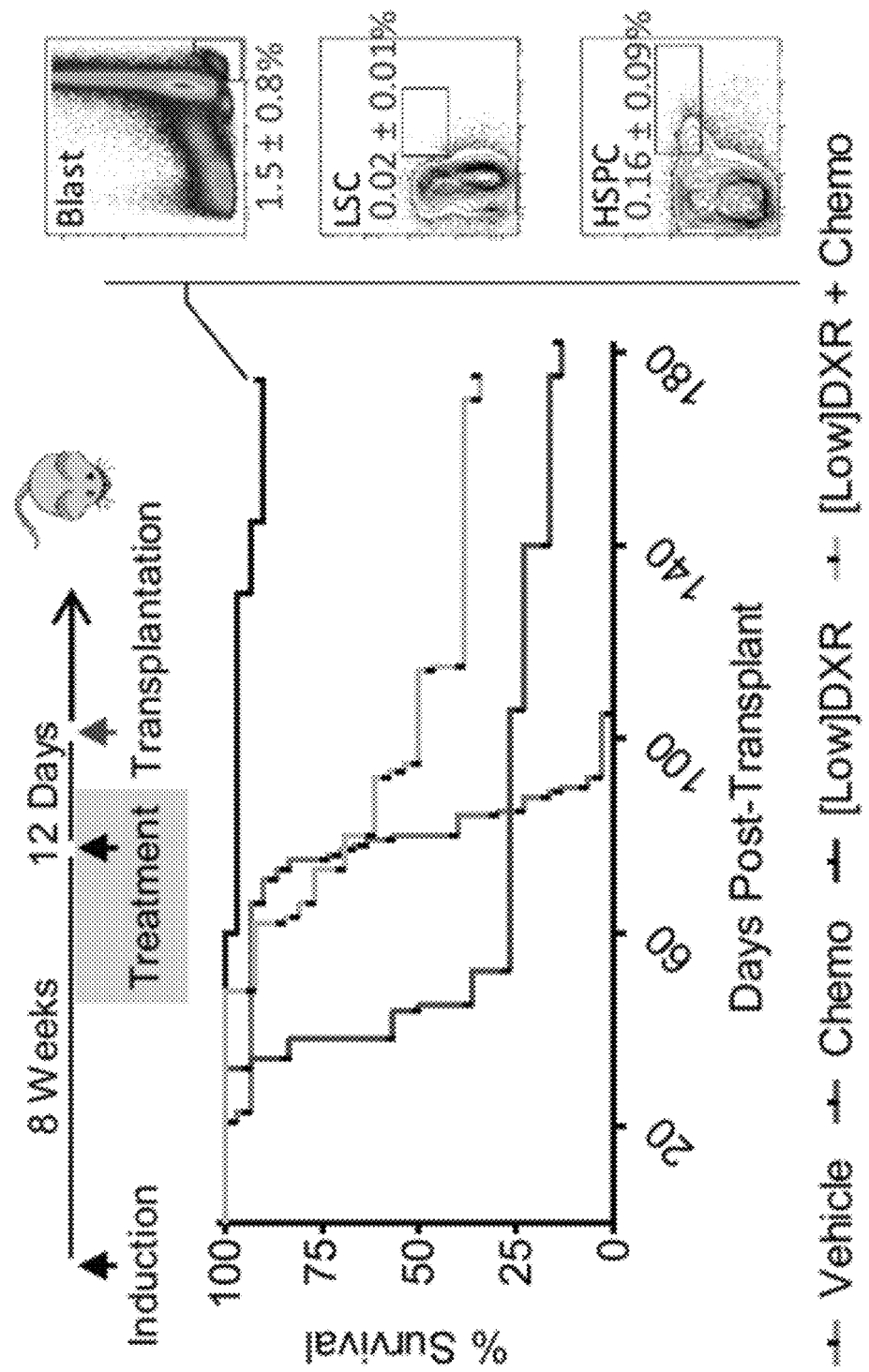

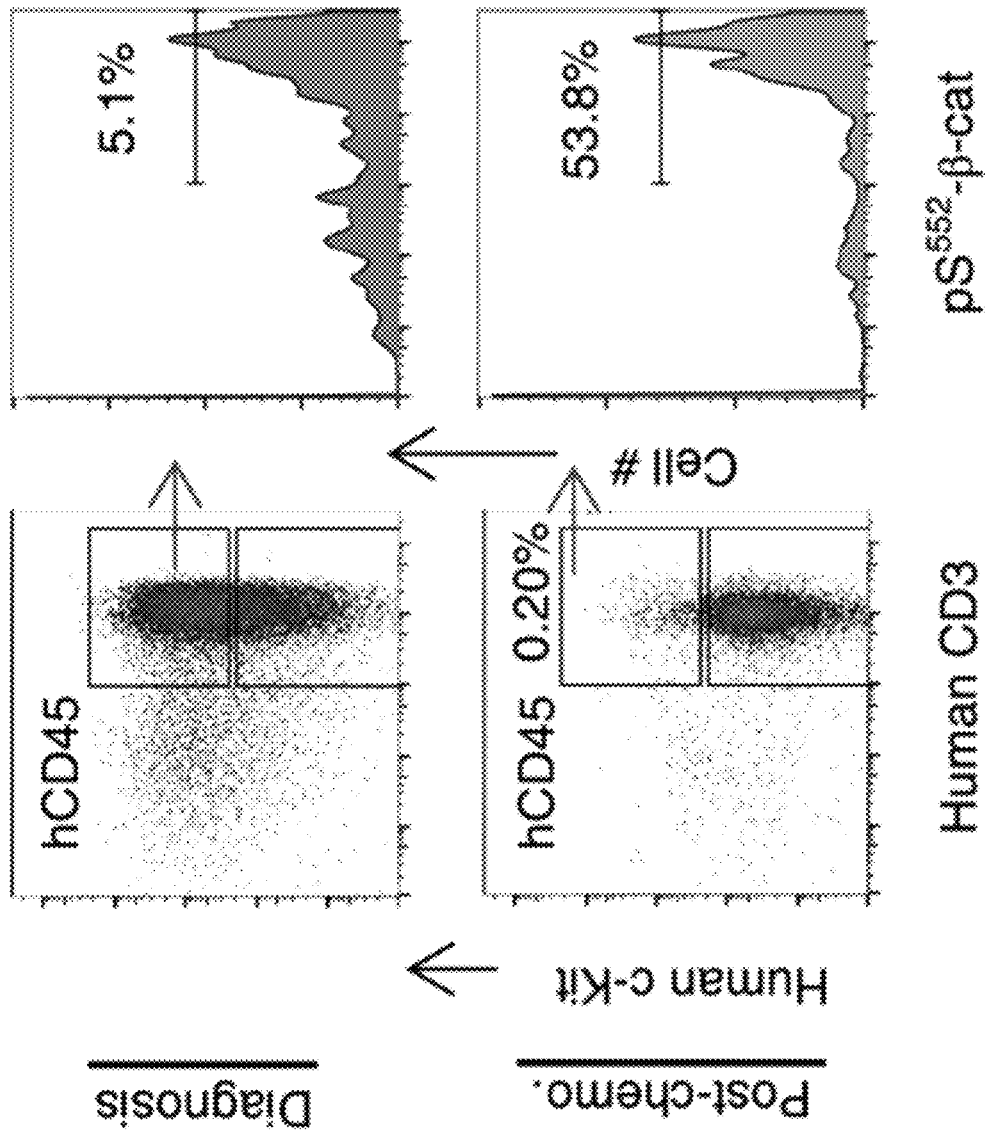

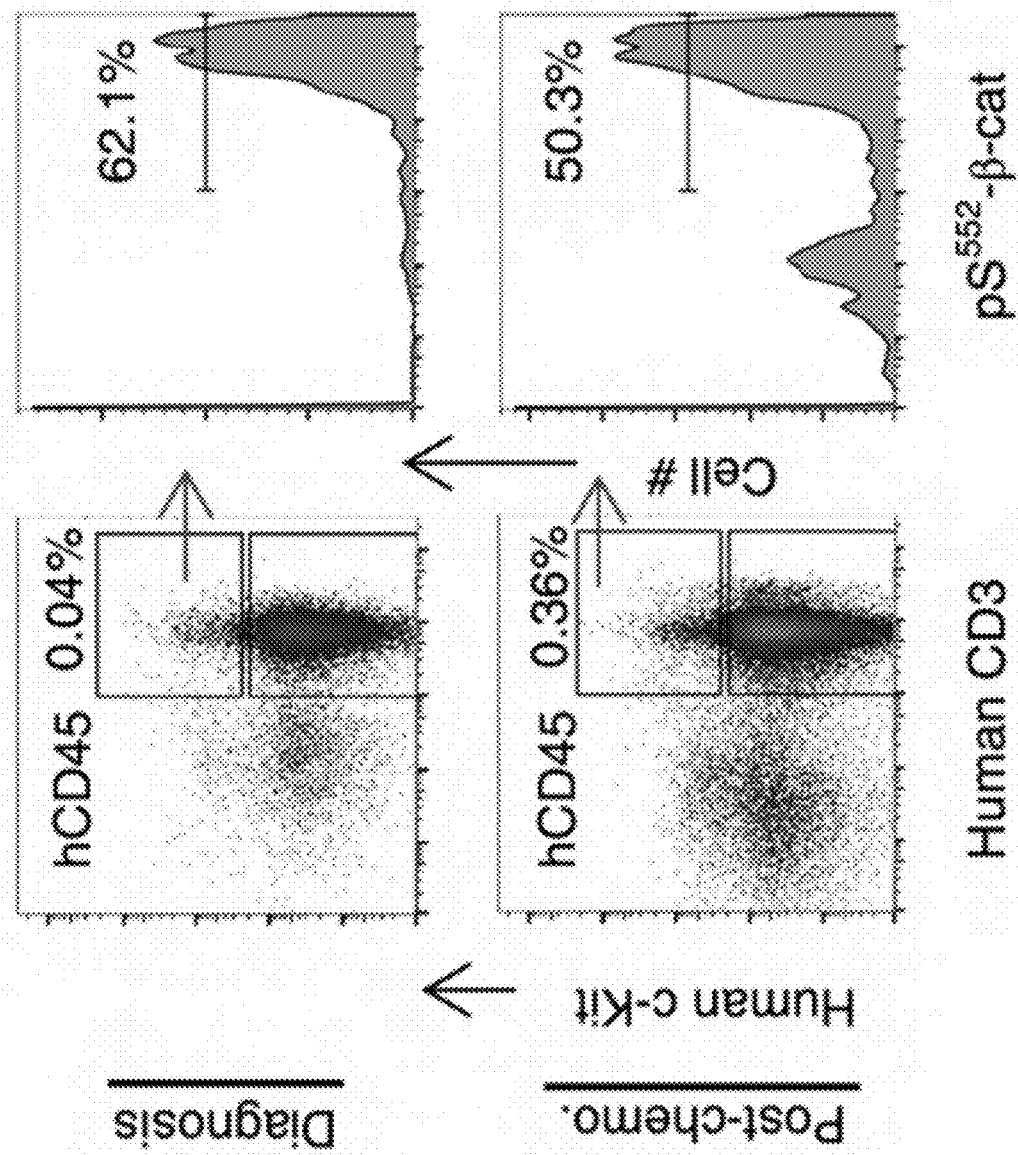

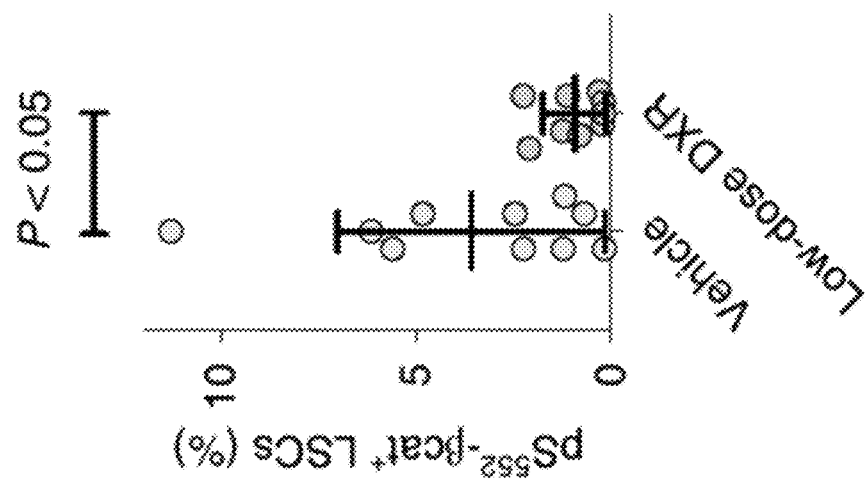
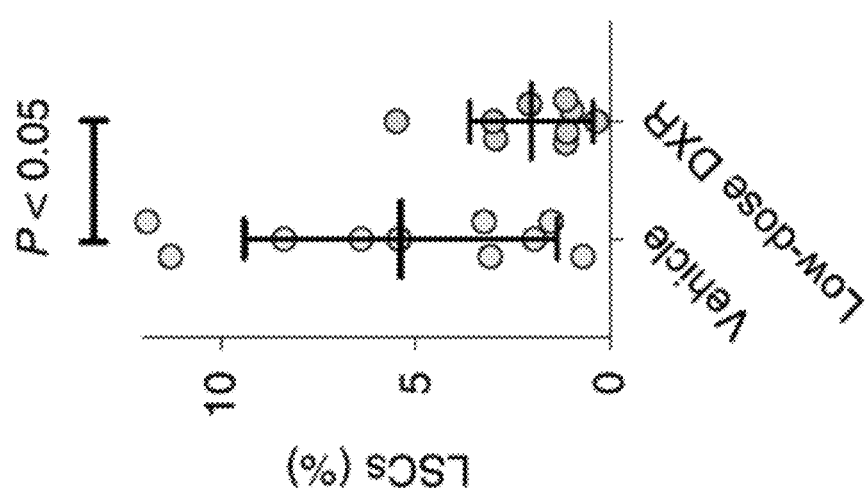
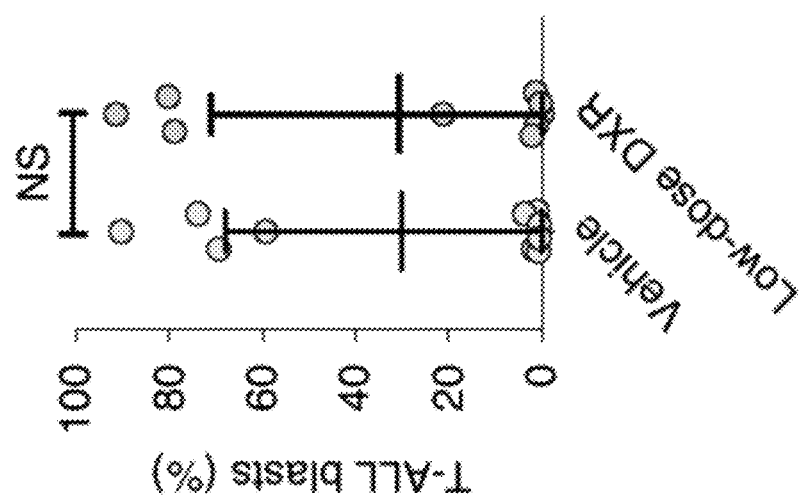

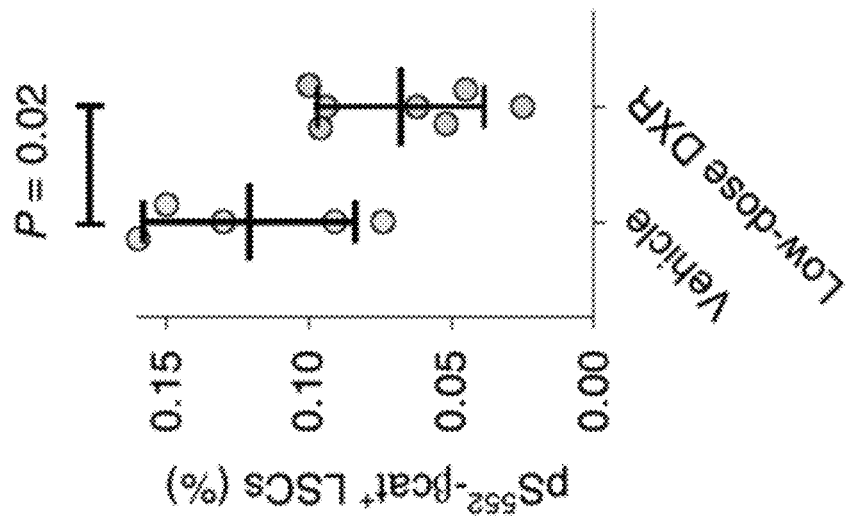
Fig. 6I  Patient 62 PDX
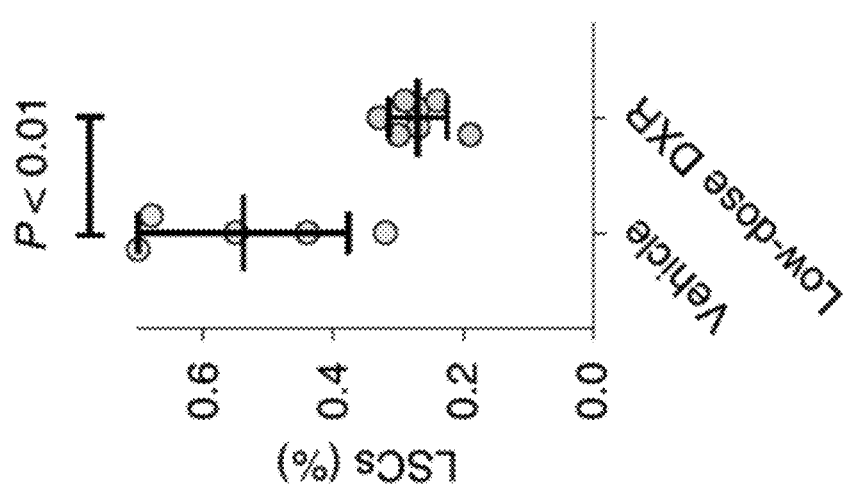
Fig. 6J
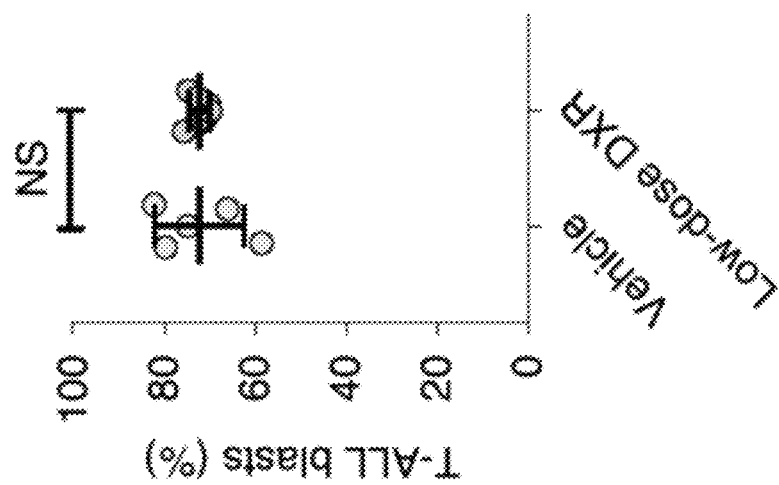
Fig. 6K

Fig. 7B
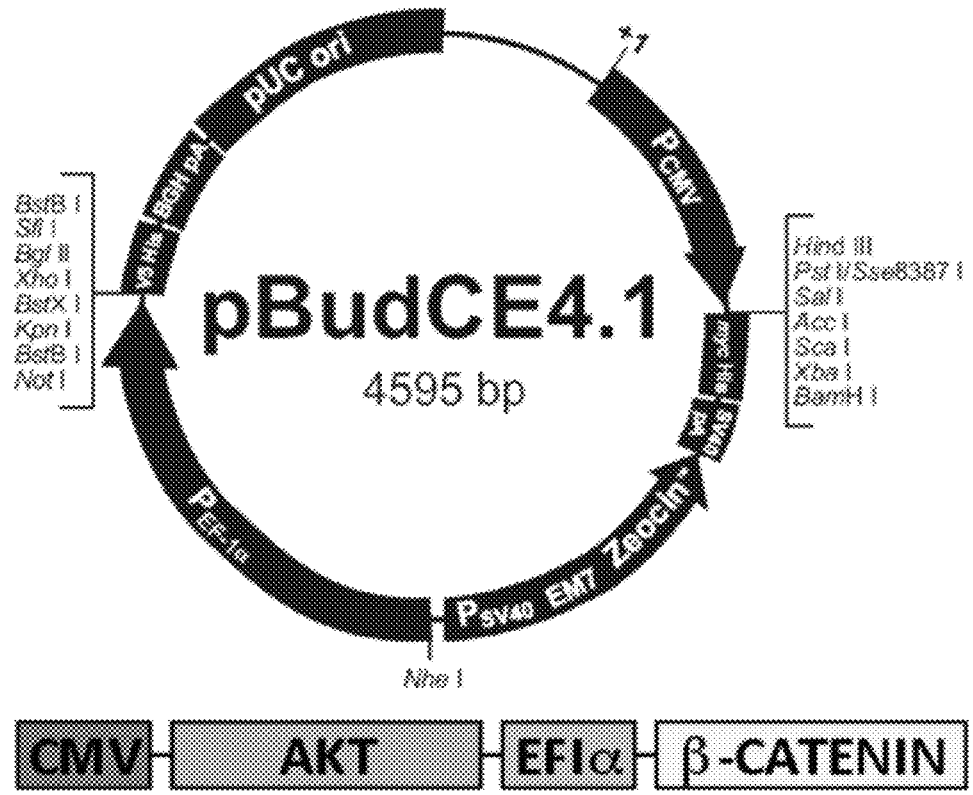
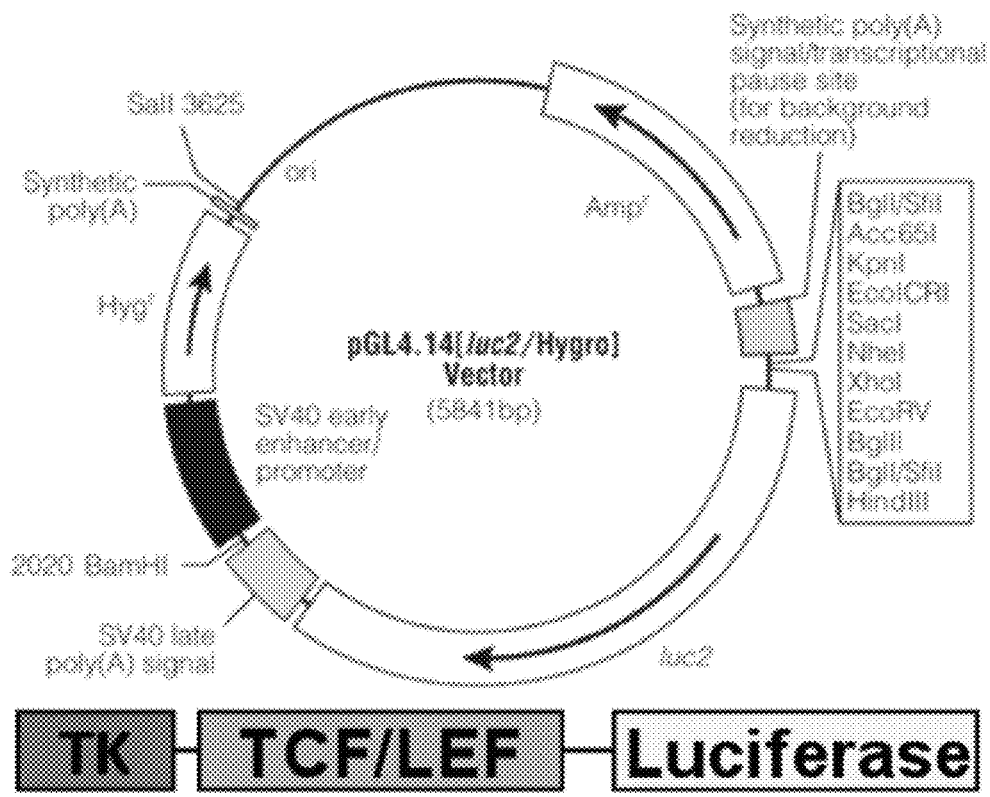

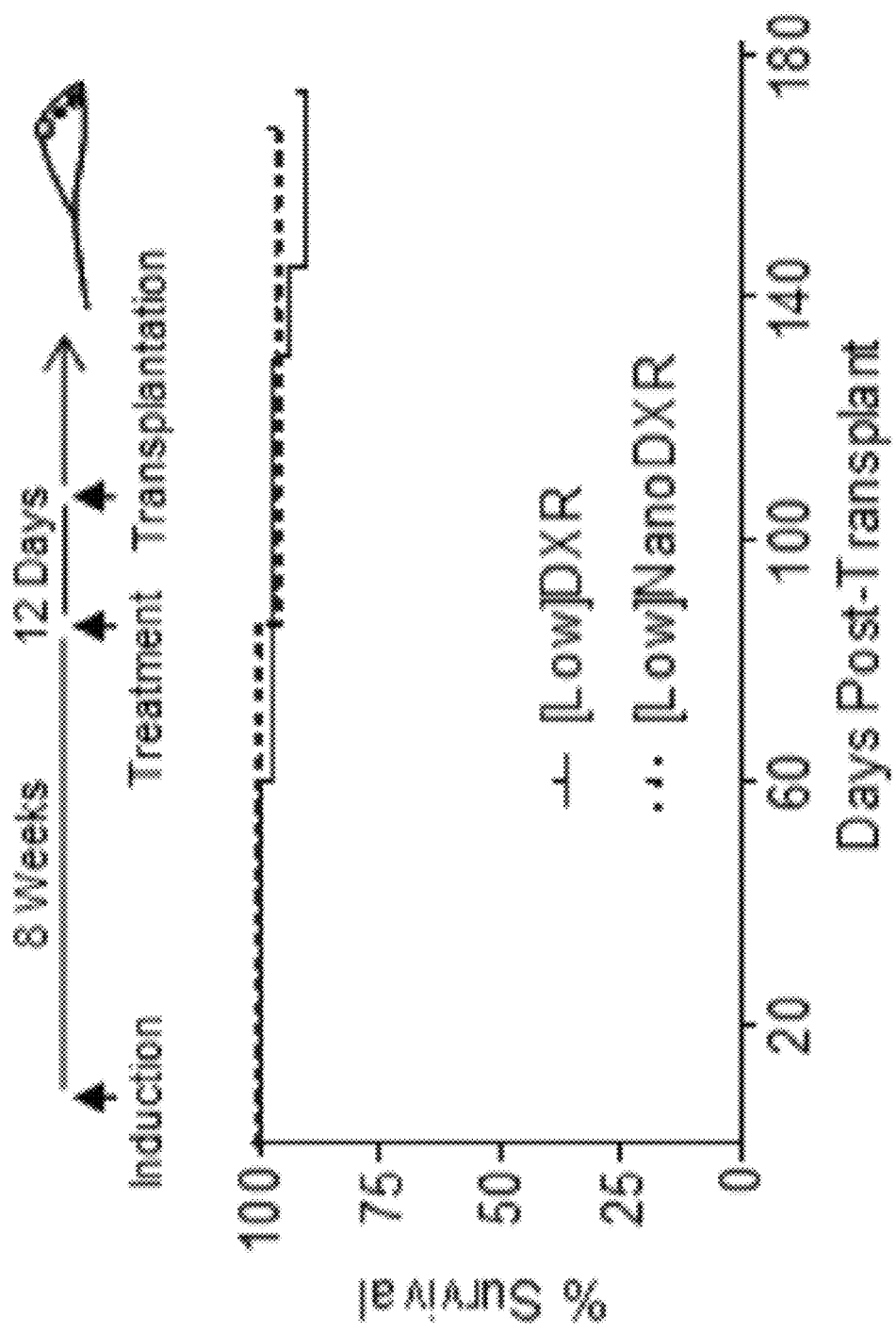

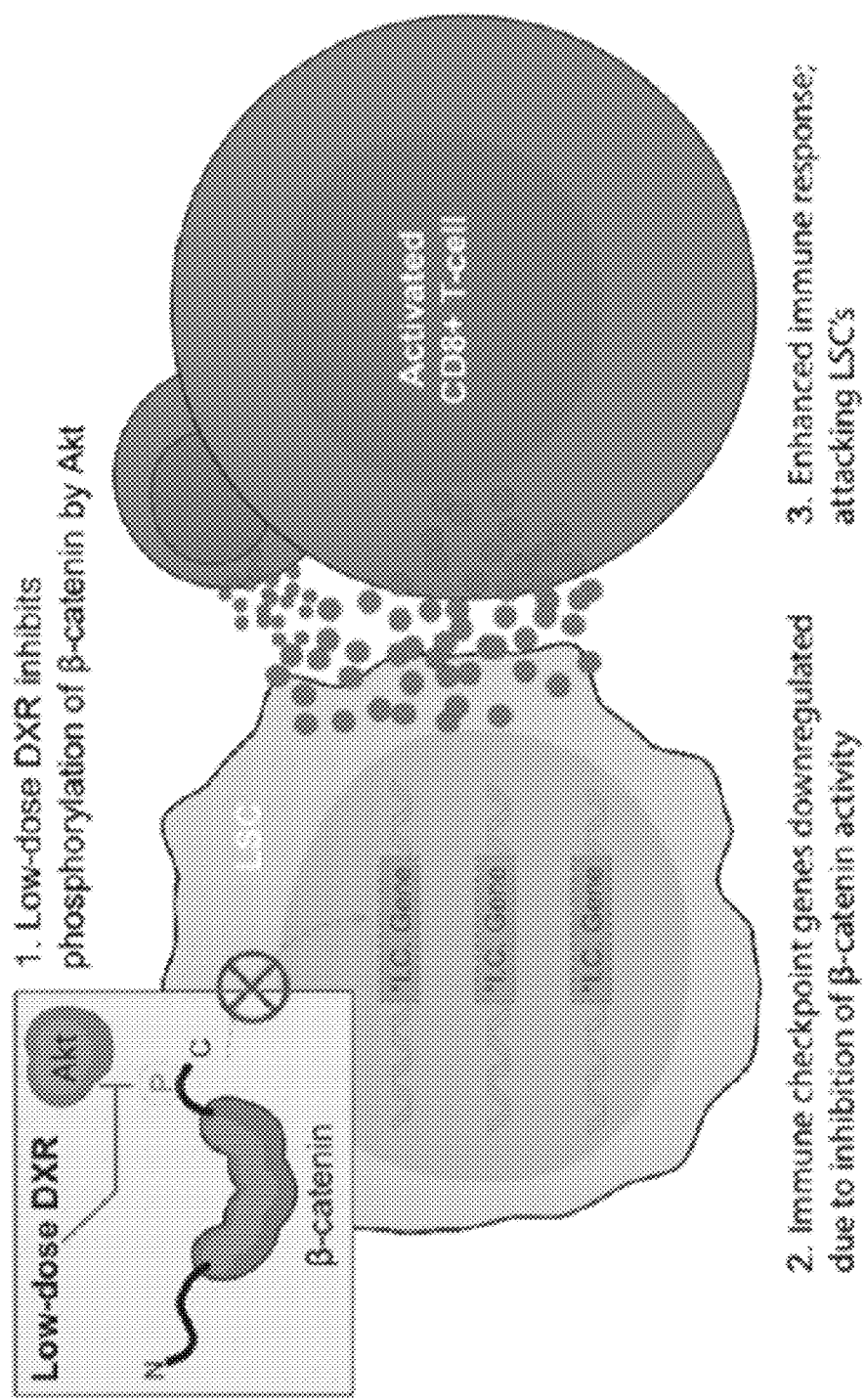

SEQUENCE LISTING

```
<160> NUMBER OF SEQ ID NOS: 5

<210> SEQ ID NO 1
<211> LENGTH: 50
<212> TYPE: DNA
<213> ORGANISM: Artificial Sequence
<220> FEATURE:
<223> OTHER INFORMATION: primer

<400> SEQUENCE: 1
aatgatacgg cgaccaccga gatctacact cgtcggcagc gtcagatgtg            50

<210> SEQ ID NO 2
<211> LENGTH: 61
<212> TYPE: DNA
<213> ORGANISM: Artificial Sequence
<220> FEATURE:
<223> OTHER INFORMATION: primer

<400> SEQUENCE: 2
taaggcgaca agcagaagac ggcatacgag attcgcctta gtctcgtggg ctcggagatg    60
t                                                                    61

<210> SEQ ID NO 3
<211> LENGTH: 61
<212> TYPE: DNA
<213> ORGANISM: Artificial Sequence
<220> FEATURE:
<223> OTHER INFORMATION: primer
```

```
<400> SEQUENCE: 3
cgtactagca agcagaagac ggcatacgag atctagtacg gtctcgtggg ctcggagatg    60
t                                                                    61

<210> SEQ ID NO 4
<211> LENGTH: 61
<212> TYPE: DNA
<213> ORGANISM: Artificial Sequence
<220> FEATURE:
<223> OTHER INFORMATION: primer

<400> SEQUENCE: 4
aggcagaaca agcagaagac ggcatacgag atttctgcct gtctcgtggg ctcggagatg    60
t                                                                    61

<210> SEQ ID NO 5
<211> LENGTH: 61
<212> TYPE: DNA
<213> ORGANISM: Artificial Sequence
<220> FEATURE:
<223> OTHER INFORMATION: primer

<400> SEQUENCE: 5
tcctgagcca agcagaagac ggcatacgag atgctcagga gtctcgtggg ctcggagatg    60
t                                                                    61
```

METHODS FOR OVERCOMING WNT/BETA-CATENIN ANTI-CANCER RESISTANCE IN LEUKEMIA STEM CELLS

CROSS REFERENCE TO RELATED APPLICATIONS

The present application claims benefit of U.S. Provisional Patent Application Ser. No. 62/867,780, filed on Jun. 27, 2019, which application is incorporated by reference herein in its entirety.

FIELD OF THE DISCLOSURE

The present disclosure provides, inter alia, methods for treating cancers including leukemia using low doses of an anthracycline such as doxorubicin.

INCORPORATION BY REFERENCE OF SEQUENCE LISTING

This application contains references to amino acids and/or nucleic acid sequences that have been filed concurrently herewith as sequence listing text file "1065334-000161-seq.txt", file size of 2 KB, created on Jun. 26, 2020. The aforementioned sequence listing is hereby incorporated by reference in its entirety pursuant to 37 C.F.R. § 1.52(e)(5).

BACKGROUND

Resistance to anti-cancer therapies leads to relapse, a critical barrier to successful treatment. Chemotherapy relies on broad cytotoxicity, resulting in adverse side-effects and the evolution of resistant clones (Kuttesch et al. 1996; Greaves et al. 2012; Kreso et al. 2014). Although the initial response to these anti-cancer therapies can be substantial, chemoresistant leukemia stem cells (LSCs), a subpopulation harbored within minimal residual disease (MRD), often lead to therapy-resistant relapse (Kreso et al. 2014; Dick et al. 2008; Eppert et al. 2011; Greaves, 2007 & 2011; Ding et al. 2012; Hanahan et al. 2011; Holohan et al. 2013). LSCs are a rare (ranging from <1% to 0.00001%) (Cleary et al. 2009) but powerful population—for example, here 1,300-fold increase in leukemia-initiating activity.

PTEN/PI3K/AKT mutations are common in many cancers and can drive resistance to anticancer therapies (Peng et al. 2016; Fruman et al. 2017; Ciraolo et al. 2011; Cully et al. 2006; Fruman et al. 2014; Hennessy et al. 2005; Koren et al. 2017; Thorpe et al. 2014; Gutierrez et al. 2009). Recent studies on pediatric acute lymphocytic leukemia (ALL) also showed that additional epigenetic mutations in relapsed vs. diagnostic samples converged on the Wnt pathway (Hogan et al. 2011; Bhatla et al. 2012). Similarly, in acute myelogenous leukemia (AML), genetic inhibitors of the Wnt pathway are frequently silenced, which predicts poor treatment outcomes including increased relapse (Bolouri et al. 2018; Griffiths et al. 2010). Since intensified chemotherapy does not improve the poor prognosis of relapsed patients, finding a better way to target chemoresistant cells is critical (Dandekar et al. 2014).

The Wnt/β-catenin and PI3K/Akt pathways are among the most frequently mutated in cancer (Kandoth et al. 2013), and cooperation between them promotes stem cell survival, proliferation, tumorigenesis, and therapy resistance (Huang et al. 2012; Korkaya et al. 2009; Huang et al. 2009; Conley et al. 2012; He et al. 2007; Perry et al. 2011; Knapp et al. 2017). Since rare, LSCs often underlie therapeutic resistance (Kreso et al. 2014; Shlush et al. 2014), inhibiting these pathways or their interaction might inhibit chemoresistant LSCs (Kreso et al. 2014; Dick et al. 2008; Eppert et al. 2011; Shlush et al. 2014; Reya et al. 2001; Nguyen et al. 2012; Clevers, 2011). Previous studies illustrate the potential but also reveal limitations in targeting the Wnt/β-catenin and PI3K/Akt pathways separately in anti-cancer therapy. Targeting elements of each pathway has shown limited efficacy and often result in the outgrowth of resistant clones (Fruman et al. 2014; Zhou et al. 2017; Kurtova et al. 2014; Heidel et al. 2012; Zhao et al. 2007; Toska et al. 2017; Tenbaum et al. 2012; Kaveri et al. 2013; Guo et al. 2008; Roderick et al. 2014; Schubbert et al. 2014; Dail et al. 2014). We and others have previously demonstrated a critical role for Wnt/β-catenin and PI3K/Akt pathway cooperation in stem cell regulation and tumorigenesis (Huang et al. 2012; Korkaya et al. 2009; Huang et al. 2009; He et al. 2007; Perry et al. 2011; Knapp et al. 2017; Tenbaum et al. 2012; Kaveri et al. 2013; Guo et al. 2008; Huang et al. 2007; Lechman et al. 2012; Xu et al. 2013; Levine et al. 2013; Guezguez et al. 2016; A-Dhfyan et al. 2017). Mechanistically, this cooperation can be driven in part by Akt C-terminal phosphorylation of β-catenin, which, unlike N-terminal phosphorylation, results in enhanced β-catenin activity (He et al. 2007). Akt phosphorylation of β-catenin occurs predominantly at serine 552 and potentially three additional sites (He et al. 2007). Thus, anti-pS552-β-catenin antibody can be used as a readout to indicate the cooperation between the Wnt/β-catenin and PI3K/Akt pathways (Conley et al. 2012; He et al. 2007; Brown et al. 2011; Lee et al. 2010).

While immunotherapy has shown some remarkable success across a wide-range of cancer, it remains effective in only a minority of patients. Resistance to immunotherapy is also driven by a combination of Wnt, PI3K and/or MAPK signaling, and lack of anti-cancer T cell response (Sharma et al. 2017). Indeed, Wnt signaling reduces T cell recruitment to tumors (Spranger et al. 2015; Spranger et al. 2018), but the mechanism responsible is unclear. Similarly, loss of PTEN, resulting in PI3K activation, inhibits T cell-mediated anti-cancer activity (Peng et al. 2016). Furthermore, the efficacy of conventional and targeted therapies often relies on not only direct cytotoxic effects but on the restoration of cancer-targeting immune responses (Galluzzi et al. 2015). In particular, the efficacy of DXR is severely compromised by ablation of CD8+ T cells (Casares et al. 2005). As chemotherapeutic drugs are often given at or near the maximum-tolerated dose (MTD), which causes immunosuppressive side effects, beneficial immunological side effects of these drugs could be compromised at high doses.

Accordingly, there remains a need for more efficacious methods for overcoming cancer therapy resistance and immune escape.

SUMMARY

Given the Wnt/β-catenin and PI3K/Akt pathway's cooperative role in resistance to multiple anti-cancer therapies, here we use a mouse model where a subset of stem cells has oncogenic activation of both pathways to study therapeutic resistance. Unexpectedly, the anthracycline antibiotic DXR, a long-used chemotherapeutic agent having the broadest known spectrum of anti-cancer activity, can selectively inhibit Akt-activated β-catenin at low doses. At high doses typically used in the clinic, DXR acts as a topoisomerase II poison and its use is limited by severe side effects, particularly cardiotoxicity which necessitates a maximum cumulative dosage (Rabbani et al. 2005; Gewirtz, 1999). However, toxicity may be reduced if DXR were repurposed as a targeted Akt:β-catenin interaction inhibitor using a low dosage rather than a chemotherapeutic, which requires a high dosage. We show that, by using low but more sustained, metronomic doses of DXR, leukemia-initiating activity of LSCs is inhibited. Mechanistically, we show that β-catenin binds multiple immune checkpoint gene loci, and while targeted DXR treatment inhibits expression of multiple immune checkpoints and promotes the restoration of anti-cancer immunity, clinical doses induce oncogenic resistance mechanisms and reduce cancer-fighting T cells. Although the relevance of our animal model findings to the clinic will take significant time to fully establish, since leukemia-initiating activity of human leukemia containing chemoresistant $pS^{552}$-β-catenin$^+$ LSCs can be reduced with low-dose anthracycline treatment and can reduce residual post-chemotherapy $pS^{552}$-β-catenin$^+$ LSCs in relapse/refractory AML patients, these findings are expected to have important future clinical applications in reducing chemoresistance and relapse.

One embodiment of the present disclosure is a method for treating or ameliorating the effects of a cancer in a subject comprising administering to the subject a low dose of a first agent, wherein the first agent is an anthracycline or pharmaceutically acceptable salt thereof, and a therapeutically effective amount of a second agent.

Another embodiment of the present disclosure is a method for treating or ameliorating the effects of leukemia in a subject comprising administering to the subject a low dose of doxorubicin or pharmaceutically acceptable salt thereof, and a therapeutically effective amount of pembrolizumab.

These and other aspects of the present disclosure are further disclosed in the detailed description and examples which follow.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1A shows the FACS analysis of BM at 8-9 wpi, indicating that all double mutants, but not single mutants, developed leukemia characterized by 20% CD45$^{Hi}$blast crisis cells.

FIG. 1B shows that these cells predominantly expressed CD3 but lacked both CD4 and CD8 expression, indicative of an early T-ALL.

FIG. 1C shows that prior to T-ALL development, Pten: β-cat$^{Act}$ mice exhibited expansion of HSPCs identified by FACS as Lin-Sca-1+c-Kit$^+$(LSK) cells.

FIG. 1D shows that the HSPC population collapsed as LSCs, identified as Lin-c-Kit$^{Mid}$CD3$^+$ cells, expanded.

FIG. 1E shows that Kaplan-Meier survival curves indicated that all double mutants, but not single mutants, succumbed to leukemia by 12 wpi. Frequencies are based on percent of total nucleated cells±standard deviation (SD).

FIG. 2A shows that the activity of thioguanosine was tested against HEK-293 TOPFlash Akt$^{Act}$ βcat$^{Act}$ (TOP) and control HEK-293 FOPFlash Akt$^{Act}$ βcat$^{Act}$ (FOP) cells at multiple doses for inhibition of luciferase activity. Cytotoxicity profiles (CTG) were also determined. Representative data were shown.

FIG. 2B shows that the activity of 0105375 was tested against HEK-293 TOPFlash Akt$^{Act}$ βcat$^{Act}$ (TOP) and control HEK-293 FOPFlash Akt$^{Act}$ βcat$^{Act}$ (FOP) cells at multiple doses for inhibition of luciferase activity. Cytotoxicity profiles (CTG) were also determined. Representative data were shown.

FIG. 2C shows that the activity of doxorubicin was tested against HEK-293 TOPFlash Akt$^{A}$d cat$^{Act}$ (TOP) and control HEK-293 FOPFlash Akt$^{Act}$ βcat$^{Act}$ (FOP) cells at multiple doses for inhibition of luciferase activity. Cytotoxicity profiles (CTG) were also determined. Representative data were shown.

FIG. 2D shows that dose-response data of thioguanosine were used to calculate the effective concentration of compound resulting in 90%, 50%, and 25% inhibition of luminescence or cytotoxicity ($EC_{90}$, $EC_{50}$, and $EC_{25}$) using nonlinear regression analysis. TOP and FOP cells were treated with thioguanosine at $EC_{90}$, $EC_{50}$ and $EC_{25}$ derived from FIG. 2A for 48 hours, washed and flash frozen for Western analysis. $EC_{50}$ data is shown.

FIG. 2E shows that dose-response data of 0105375 were used to calculate the effective concentration of compound resulting in 90%, 50%, and 25% inhibition of luminescence or cytotoxicity ($EC_{90}$, $EC_{50}$, and $EC_{25}$) using nonlinear regression analysis. TOP and FOP cells were treated with compound 0105375 at $EC_{90}$, $EC_{50}$ and $EC_{25}$ derived from FIG. 2B for 48 hours, washed and flash frozen for Western analysis. $EC_{50}$ data is shown.

FIG. 2F shows that dose-response data of doxorubicin were used to calculate the effective concentration of compound resulting in 90%, 50%, and 25% inhibition of luminescence or cytotoxicity ($EC_{90}$, $EC_{50}$, and $EC_{25}$) using nonlinear regression analysis. TOP and FOP cells were treated with doxorubicin at $EC_{90}$, $EC_{50}$ and $EC_{25}$ derived from FIG. 2C for 48 hours, washed and flash frozen for Western analysis. $EC_{50}$ data is shown.

FIG. 2G is a computational model showing predicted binding of Akt and DXR to β-catenin.

FIG. 2H shows the FRET analysis verifying interaction between AKT and β-catenin. Cells transfected with EGFP-AKT and mCherry-β-catenin were treated with vehicle or Doxorubicin at the indicated concentrations and FRET efficiency was determined.

FIG. 2I shows the FRET efficiency at the indicated time points post-doxorubicin (200 nM) addition.

FIGS. 3A-3K show the differential response of LSCs, HSPCs and blast cells to chemotherapy, clinical-dose DXR and low-dose DXR. Leukemic mice were treated with vehicle, chemotherapy, [Low]DXR (5×0.5 mg/kg), clinical DXR (1×20 mg/kg), or chemotherapy+[Low]DXR as described in FIG. S2.

FIG. 3A is an Illustration of strategy for repurposing DXR as a targeted therapy. Open arrows indicate a single treatment cycle for typical clinical use of DXR and targeted use strategy drawn to relative scales. Triangles represent DXR treatment drawn proportionally to scale. The cumulative targeted dose (distributed over 5 days consecutively) is indicated to relative scale by the inner triangle (white).

FIG. 3B shows that at 5 days post-treatment, BM was analyzed by FACS to determine frequency of blast cells, LSCs, and HSPCs. Average frequency of each population (n≥6 per group) is shown.

FIG. 3C shows that at 5 days post-treatment, BM was analyzed by FACS to determine frequency of blast cells, LSCs, and HSPCs. Absolute number/femur±SD of each population (n≥6 per group) is shown.

FIG. 3D shows that leukemic mice were treated with vehicle, chemotherapy (Nelarabine (Nel.)+dexamethasone (Dexa.)), [Low]DXR with Dexa., or clinical dose DXR (here, 5×4 mg/kg daily) with Dexa. At 10 days post-treatment, BM was analyzed by flow cytometry to determine frequency of blast cells. Average frequency±SD (n 6 per group). Note that this experiment used clinical dose (normal) or [Low] DXR as a substitute for Nelarabine (both DNA damaging agents) but Dexamethasone treatment (a corticosteroid) was retained in all groups due to the inability of single DNA damaging agents to effectively reduce blast cells. These data show that, even in combination with dexamethasone, [Low]DXR does not act as a traditional chemotherapeutic while clinical DXR does.

FIG. 3E shows the representative flow cytometry gates indicating HSPC, LSC and (non-LSC) T-ALL blast cell populations.

FIG. 3F shows the verification of anti-$pS^{552}$-β-catenin specificity. Leukemic mice from vehicle control group were also stained with isotype control for anti-$p^{552}$-β-catenin; gating based on the LSC population is shown.

FIG. 3G shows that conditional knockout 3-catenin mice (3-cat KO) were stained with anti-$pS^{552}$-β-catenin; here, gating based on the HSPC population is shown since these mice do not develop LSCs. Minimal staining could be due to incomplete knock-out.

FIG. 3H shows that populations from FIG. 3E were analyzed from leukemic mice treated as indicated and stained with anti-$pS^{552}$-β-catenin antibody at 4 days post-treatment. Percent of LSC, HSPC or blast cell population expressing $pS^{552}$-β-catenin is indicated for each treatment. Numbers indicate mean±SD; n=3-5 per group.

FIG. 3I shows the protocol of limiting-dilution assays to determine CRU frequency.

FIG. 3J shows the result of limiting-dilution assays performed on blast cells sorted from chemotherapy treated leukemic mice using the indicated cell dose. Engraftment (≥1% blast cells) was determined in recipients at 10-12 weeks post-transplant. Average donor engraftment %±SD is shown in upper right of panels with CRU fraction in lower right.

FIG. 3K shows the result of limiting-dilution assays performed on LSCs sorted from chemotherapy treated leukemic mice using the indicated cell dose. Engraftment (≥1% blast cells) was determined in recipients at 10-12 weeks post-transplant. Average donor engraftment %±SD is shown in upper right of panels with CRU fraction in lower right.

FIGS. 4A-4O show that low-dose DXR treatment restores immune regulation but clinical-dose DXR stimulates therapy-resistance.

FIG. 4A shows the transcriptome analysis of blast cells, LSCs, and HSPCs sorted from treated, leukemic mice. HSPCs, LSCs, and blast cells were sorted by FACS at 5 days post-treatment of leukemic mice; representative sorting gates are shown. Note distinct LSC population (compare to isotype) in vehicle versus low-dose DXR+chemotherapy treatment when LSCs show very low frequency. Other plots are from vehicle control. To obtain sufficient cells from the clinical DXR sample, the 5×4 mg/ml DXR daily dosing schedule was used.

FIG. 4O shows that $CD8^+$T cells were depleted with anti-CD8 prior to [Low]DXR treatment and then analyzed by FACS. n=10 biologically independent mice for each group; data are mean±s.e.m.

FIGS. 5A-5G show that chemotherapy induction combined with maintenance targeted/low-dose DXR treatment increases survival.

FIG. 5A shows that cohorts of leukemic mice were treated with vehicle, chemotherapy, [Low]DXR or chemotherapy+ [Low]DXR as in FIG. S2. Treatment schematic and Kaplan-Meier curves of leukemic mice treated as indicated. Red arrow indicates day 0 in survival curve.

FIG. 5B shows Kaplan-Meier survival curves of leukemic mice treated with a 3-fold increased dosage of [Low]DXR+ chemotherapy or clinical-dose DXR+chemotherapy as indicated and compared to vehicle control.

FIG. 5C shows LSC and HSPC frequency in BM of leukemic mice at 5 days post-treatment with chemotherapy and either free [Low]DXR or [Low]nanoDXR.

FIG. 5D shows the treatment schematic and Kaplan-Meier curves of chemotherapy+weekly [Low]nanoDXR treatment for 10 weeks total. Dashed line indicates day of final [Low]nanoDXR treatment.

FIG. 5E shows that [Low]nanoDXR treated mice were analyzed by FACS at 230 days post-treatment.

FIG. 5F shows the tumorigenic assays for cells from treated, leukemic mice: cohorts of leukemic mice were treated with vehicle, chemotherapy, [Low]DXR or chemotherapy+[Low]DXR as in FIG. S2. At 12 days post-treatment, BM was harvested from treated mice and transplanted into sub-lethally irradiated NSG recipients. Treatment and transplantation schematic and Kaplan-Meier curves of recipient mice were shown. Red arrow indicates day 0 in survival curve.

FIG. 5G shows that recipients of BM from [Low]DXR only treated leukemic mice were analyzed by FACS at 6 months post-transplant. Shown are representative plots of blast cells, LSCs, and HSPCs with average frequency±SD of surviving 27/30 recipients from this group.

FIG. 6A shows the experimental schematic of establishment and treatment of patient-derived xenografts (PDX).

FIG. 6B shows FACs analysis of diagnostic and day 29 post-chemotherapy T-ALL BM samples from MRD$^+$ patient.

FIG. 6C shows that CD45$^+$ c-Kit$^+$ CD3$^+$ cells (LSCs) expressing $pS^{552}$-β-cat$^+$ were 4.4-fold enriched following chemotherapy in Pt 057.

FIG. 6D shows FACs analysis of diagnostic and day 29 post-chemotherapy T-ALL BM samples from MRD$^+$ patient.

FIG. 6E shows that CD45$^+$ c-Kit$^+$ CD3$^+$ cells (LSCs) expressing $pS^{552}$-β-cat$^+$ were 7.3-fold enriched following chemotherapy in Pt 062.

FIG. 6F shows that diagnostic BM samples were transplanted into NSG recipients (4×10$^5$ cells each), treated for 5 days with vehicle or [Low]DXR at 2 weeks post-transplant, and analyzed by FACs for human engraftment. Shown is T-ALL blasts (CD45$^+$ c-Kit$^{-ve}$ CD3$^+$) in Pt 057. Graphs indicate frequency of human CD45$^+$ cells (%)+SD.

FIG. 6G shows the LSCs in Pt 057. Graphs indicate frequency of human CD45$^+$ cells (%)±SD.

FIG. 6H shows the $pS^{552}$-β-cat$^+$ LSCs in Pt 057. Graphs indicate frequency of human CD45$^+$ cells (%)±SD.

FIG. 6I shows the T-ALL blasts (CD45$^+$ c-Kit$^{-ve}$ CD3$^+$) in Pt 062. Graphs indicate frequency of human CD45$^+$ cells (%)±SD.

FIG. 6J shows the LSCs in Pt 062. Graphs indicate frequency of human CD45$^+$ cells (%)±SD.

FIG. 6K shows the $pS^{552}$-β-cat$^+$ LSCs in Pt 062. Graphs indicate frequency of human CD45$^+$ cells (%)±SD.

FIG. 6N shows that $pS^{552}$-β-cat$^+$ LSCs was quantified according to gating represented in FIG. 6L at pre- and post-low dose DNR as indicated.

FIG. 7A-7E provide HTS screening and in vitro analysis showing DXR preferentially inhibits LSC expansion.

FIG. 7A is a Flow chart showing HTS design

FIG. 7B shows the vector designs for cells expressing Akt and β-catenin and TCF reporter activity.

FIG. 7C provides the FRET verification between Akt and β-catenin. While FRET was observed in mCherry-β-catenin+EGFP-AKT transfected cells and could be inhibited by DXR, essentially no discernible FRET occurred when mCherry-β-catenin was transfected with EGFP alone (see also FIGS. 2H-2I).

FIG. 7D shows that BM isolated from leukemic Pten:β-cat$^{Act}$ mice at 8 wpi was cultured in HSC expansion media as previously described (Perry et al, 2011). Doxorubicin, 0105375, and thioguanosine were added to 11, 33 or 100 nM and cultured for 72 hours and analyzed by flow cytometry for LSCs as in FIGS. 1A-1E. Fold change before and after culture for each population is indicated relative to equivalent vehicle control concentrations.

FIG. 7E shows that BM isolated from leukemic Pten:β-cat$^{Act}$ mice at 8 wpi was cultured in HSC expansion media as previously described (Perry et al, 2011). Doxorubicin, 0105375, and thioguanosine were added to 11, 33 or 100 nM and cultured for 72 hours and analyzed by flow cytometry for HSPCs as in FIGS. 1A-1E. Fold change before and after culture for each population is indicated relative to equivalent vehicle control concentrations.

FIG. 9A is the heatmap of Hallmark MYC target genes (V1) up and downregulated in HSPCs and LSCs treated with vehicle and LSCs treated with [Low]DXR. Data from two biological replicates of each, differing by <0.3 standard deviations, are shown.

FIG. 9B shows the upregulated terms in LSCs vs. HSPCs in leukemic mice (treated only with vehicle control). Provided is the Gene ontology enrichment analysis using −log 10 of the uncorrected p value as x axis. The upregulated enriched terms are shown in red. Numbers correspond to the same term upregulated.

FIG. 9C shows the downregulated terms in LSCs from [Low]DXR vs. vehicle control treated leukemic mice. Provided is the Gene ontology enrichment analysis using −log 10 of the uncorrected p value as x axis. The downregulated enriched terms are shown in blue. Numbers correspond to the same term downregulated.

FIG. 9D shows that TCF/Lef:H2B-GFP mice were stained with CD3 and c-Kit and analyzed by FACS. Percent of TCF/Lef:H2B-GFP$^+$ cells for each population are indicated.

FIG. 9E shows that TCF/Lef:H2B-GFP mice were treated with vehicle or [Low]nanoDXR and analyzed by FACS at 3 hours post-injection for TCF/Lef:H2B-GFP$^+$ cells.

FIG. 9F shows the representative FACS plots for data quantified in FIG. 9E and including untreated, TCF/Lef: H2B-GFP negative littermate control analysis.

FIG. 10A shows that CHIP-seq was performed on 2×10$^7$ cells from the β-catenin-3×Flag mouse ES cell line (provided by Andrew McMahon). Genome browser view of β-catenin binding density at the Pdcd1 (Pd-1), Havcr2 (Tim-3), Cd24a, and Ctla4 gene loci promoter regions and/or intergenic regions.

FIG. 10B shows that ATAC-seq was used to show chromatin accessibility profiles of Wnt target genes observed in blast cells (~30 k cells per replicate) and leukemic stem cells (~15 k cells per replicate).

FIG. 10C shows the accessibility profiles of immunocheckpoint genes observed by ATAC-seq in blast cells (~30 k cells per replicate) and LSCs (~15 k cells per replicate). Cells were sorted from BM pooled from 20 leukemia mice treated with [Low]DXR and 8 leukemia mice treated with vehicle control. Experiment was repeated 1 time with similar results.

FIGS. 11A-11D show that single-dose DXR-loaded nanoparticles substitute for multiple doses of free DXR in reducing LSCs. [Low] NanoDXR treatment reduces functional LSCs in vivo.

FIG. 11A shows that leukemic mice established as described in FIG. 8 were treated with 5 daily injections of free DXR at 0.5 or 0.15 μg/g with and without chemotherapy. Alternatively, a single injection on day 1 of 0.8 or 2.5 μg/g of DXR-loaded nanoparticles (NanoDXR) was given with and without chemotherapy. At 10 days post-treatment, BM was analyzed by flow cytometry to determine frequency of LSCs. Shown is average frequency±SD (n 6 per group).

FIG. 11B shows that leukemic mice established as described in FIG. 8 were treated with 5 daily injections of free DXR at 0.5 or 0.15 μg/g with and without chemotherapy. Alternatively, a single injection on day 1 of 0.8 or 2.5 μg/g of DXR-loaded nanoparticles (NanoDXR) was given with and without chemotherapy. At 10 days post-treatment, BM was analyzed by flow cytometry to determine frequency of HSPCs. Shown is average frequency±SD (n 6 per group). Note that 5 doses of 0.15 μg/g DXR is ineffective; however, a single NanoDXR injection with a similar cumulative dose (0.8 μg/g) is most effective at reducing LSCs while allowing for HSPC recovery.

FIG. 11C shows that cohorts of leukemic mice were prepared and treated as in FIG. 8 but with [Low] NanoDXR. At 12 days post-treatment, BM was harvested from treated mice and transplanted into sub-lethally irradiated NSG recipients. Treatment schematic and Kaplan-Meier curves of recipient mice are shown. The free [Low]DXR treatment group (solid line) from FIG. 5F is shown for comparison (n=30 per group).

FIG. 11D shows that recipients of BM from [Low]DXR and [Low] NanoDXR treated leukemic mice were analyzed by flow cytometry at 6 months post-transplant for Blast cells, HSPCs and LSCs (n=27-29 per group).

FIG. 12A is the summary of pediatric leukemia patients analyzed by FACS for LSCs and pS$^{552}$-β-cat$^+$ LSCs. B-lymphoid LSCs were identified as enriched in CD45$^+$ CD34$^+$ CD19$^+$ and CD45$^+$ c-Kit$^+$CD3$^+$ cells, respectively (Rabbani et al. 2005; Gewirtz, 1999; Gothert et al. 2005; Barker et al. 2018; Hsu et al. 2018). Bone marrow samples at diagnosis (untreated) are shown in grey; same-patient samples at day 29 post-chemotherapy treatment are red. Patient (Pt) samples 019 and 034, B-lymphoid leukemias exhibiting chemoresistant pS$^{552}$-β-cat$^+$ LSCs, were subjected to further in vivo treatment and analysis. Pt 024 and 031, B-lymphoid acute leukemias lacking chemoresistant pS$^{552}$-β-cat$^+$ LSCs, were also tested.

FIG. 12O shows that FACs analysis was performed on 2 PDX recipient BM from FIG. 12E. Human CD45$^+$ and human LSC engraftment was determined after succumbing to leukemia or at experimental endpoint. Graphs indicate frequency (%)+Std. Dev. (N.S.=not significant).

FIG. 13A shows the daunorubicin (DNR) dose-response (see also FIG. 2C for comparison with DXR).

FIG. 13B shows the FACs analysis of LSC, HSPC and Blast Cell frequency in leukemic mice treated with chemotherapy with either low-dose DXR or low-dose DNR.

FIGS. 14A-14B show targeting Akt-activated β-catenin dependent immune escape in LSCs. The cooperative role of the Wnt/β-catenin and PI3K/Akt pathway in resistance to anti-cancer therapies, including immune escape, confirmed the Pten:β-cat$^{Act}$ double mutant mice served as an ideal model to study cancer therapy resistance. It was found that cooperative Akt:β-catenin signaling is particularly critical for therapy-resistant LSCs.

FIG. 14A shows, unexpectedly, that Akt-activated β-catenin binds to multiple IC genes, which are expressed on LSCs.

FIG. 14B shows that in identifying DXR as an inhibitor of Akt:β-catenin interaction at low doses, it was found that DXR could be repurposed as a targeted therapy for resistant LSCs, in part by inhibiting multiple ICs, particularly PD-1/PD-L1. Notably, LSCs but not blast cells exhibit unique properties of immune resistance, which can be reduced with low-dose DXR.

DETAILED DESCRIPTION OF THE DISCLOSURE

Figure 1A:
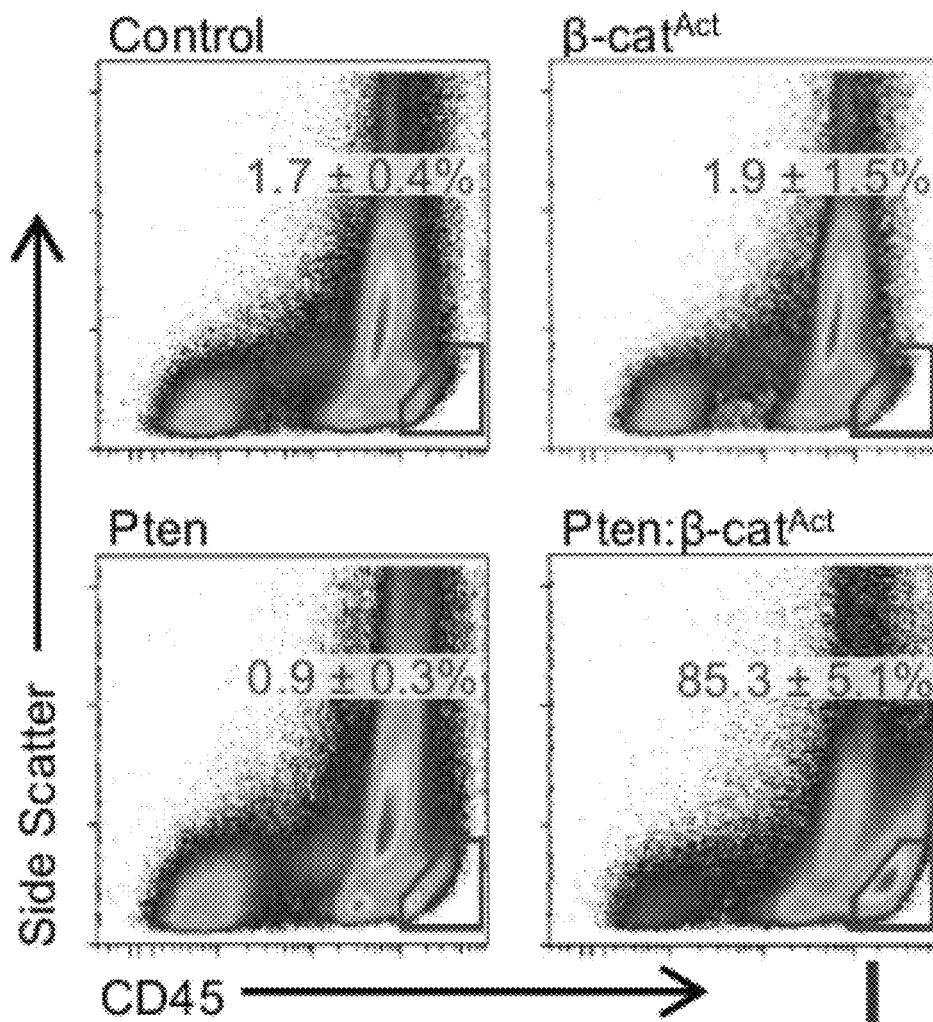
FIGS. 1A-1E show that cooperative activation of the Wnt/β-catenin and PI3K/Akt pathways successively expands HSPCs, LSCs and T-ALL blast cells. Pten:3-cat$^{Act}$ mice were induced by tamoxifen as previously described (Perry et al. 2011).

Cancer therapeutic resistance remains a critical, unsolved problem. Residual leukemia stem cells (LSCs) underlie resistance but targeting them remains elusive. The Wnt/β-catenin and PI3K/Akt pathways cooperatively promote tumorigenesis, stem cell survival and proliferation, and resistance to anti-cancer therapies. Here, we used a mouse model with activation of both pathways to study therapeutic resistance. Unlike bulk leukemic blast cells, LSCs driven by activation of both pathways are not only chemoresistant but expand in response to chemotherapy. Since Akt can activate β-catenin by C-terminal phosphorylation (pS$^2$-β-catenin), inhibiting this interaction might target therapy-resistant LSCs. Unexpectedly, high-throughput screening (HTS) identified doxorubicin (DXR) as an inhibitor of Akt:β-catenin interaction at low doses. We repurposed DXR as a targeted inhibitor rather than a traditional, broadly cytotoxic chemotherapy. Targeted use of DXR reduced Akt-activated β-catenin levels in chemoresistant LSCs, prevented LSC expansion in response to chemotherapy, reduced LSC tumorigenic activity, and substantially increased survival. Mechanistically, β-catenin binds multiple immune checkpoint (IC) gene loci, and targeted DXR treatment inhibited expression of multiple ICs specifically on LSCs, including PD-L1, TIM3, and CD24. However, clinical doses induced oncogenic resistance mechanisms, reversing this inhibition of ICs. Overall, LSCs, unlike their blast cell progeny, exhibit unique properties of immune resistance that are reduced with low-dose DXR. Using patient samples, low-dose DXR treatment also inhibits leukemia-initiating activity of samples exhibiting chemoresistant pS$^{552}$-β-cat$^+$ LSCs, and similar treatment of relapsed or refractory patients reduced pS$^{552}$-β-cat$^+$ LSCs. The present disclosure provides a more efficacious remedy for overcoming cancer therapy resistance and immune escape.

Accordingly, one embodiment of the present disclosure is a method for treating or ameliorating the effects of a cancer in a subject comprising administering to the subject a low dose of a first agent, wherein the first agent is an anthracycline or pharmaceutically acceptable salt thereof, and a therapeutically effective amount of a second agent.

In some embodiments, the low dose of the first agent comprises a dosage per course that is less than ½ of the standard dose of the first agent. In some embodiments, the low dose of the first agent comprises a dosage per course that is less than ¼ of the standard dose of the first agent. In some embodiments, the low dose of the first agent comprises a dosage per course that is less than ⅛ of the standard dose of the first agent. In some embodiments, the low dose of the first agent comprises a dosage per course that is less than 1/20 of the standard dose of the first agent. In some embodiments, the low dose of the first agent comprises a dosage per course that is less than 1/40 of the standard dose of the first agent.

In some embodiments, the anthracycline is selected from the group consisting of doxorubicin, daunorubicin, epirubicin, idarubicin, mitoxantrone, valrubicin, and combinations thereof. In some embodiments, the anthracycline is doxorubicin.

The standard dose of doxorubicin is 40-75 mg/m$^2$ per course. In some embodiments, the low dose of doxorubicin comprises a dosage per course of approximately 7.5 mg/m$^2$. In some embodiments, doxorubicin is administered daily at 1/40 of its clinical dose for 5 consecutive days.

In some embodiments, the second agent is a chemotherapeutic. In some embodiments, the chemotherapeutic is selected from nelarabine, dexamethasone, and combinations thereof.

In some embodiments, the second agent is an immune checkpoint inhibitor. In some embodiments, the immune checkpoint inhibitor is selected from a group consisting of an anti-PD-1 antibody, an anti PD-L1 antibody, an anti-CTLA-4 antibody, and combinations thereof. In some embodiments, the immune checkpoint inhibitor is selected from a group consisting of nivolumab (Bristol-Myers Squibb), pembrolizumab (Merck), pidilizumab (Curetech), AMP-224 (GlaxoSmithKline/Amplimmune), MPDL3280A (Roche), MDX-1105 (Medarex, Inc./Bristol Myer Squibb), MEDI-4736 (Medimmune/AstraZeneca), arelumab (Merck Serono), ipilimumab (YERVOY, (Bristol-Myers Squibb), tremelimumab (Pfizer), pidilizumab (CureTech, Ltd.), IMP321 (Immutep S.A.), MGA271 (Macrogenics), BMS-986016 (Bristol-Meyers Squibb), lirilumab (Bristol-Myers Squibb), urelumab (Bristol-Meyers Squibb), PF-05082566 (Pfizer), IPH2101 (Innate Pharma/Bristol-Myers Squibb), MEDI-6469 (Medimmune/AZ), CP-870,893 (Genentech), Mogamulizumab (Kyowa Hakko Kirin), Varlilumab (CellDex Therapeutics), Avelumab (EMD Serono), Galiximab (Biogen Idec), AMP-514 (Amplimmune/AZ), AUNP 12 (Aurigene and Pierre Fabre), Indoximod (NewLink Genetics), NLG-919 (NewLink Genetics), INCB024360 (Incyte) and combinations thereof. In some embodiments, the immune checkpoint inhibitor is pembrolizumab.

In some embodiments, the first and second agents are co-administered. In some embodiments, the first agent is administered prior to the second agent. In some embodiments, the second agent is administered prior to the first agent.

In some embodiments, the administration of the first and second agents to the subject provides a synergistic effect in the treatment of the cancer.

In some embodiments, the cancer is selected from the group consisting of bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, multiple myeloma, neuroblastoma, neuroendocrine cancer, ovarian cancer, pancreatic cancer, prostate cancer, rectal cancer, renal cell carcinoma, rhabdoid cancer, sarcomas, and urinary track cancer. In some embodiments, the cancer is selected from the group consisting of acute myeloid leukemia (AML), chronic myeloid leukemia (CML), acute lymphocytic leukemia (ALL), and chronic lymphocytic leukemia (CLL).

As used herein, a "subject" is a mammal, preferably, a human. In addition to humans, categories of mammals within the scope of the present disclosure include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include primates, rats, mice, rabbits, guinea pigs, etc. In some embodiments, the subject is a human.

In some embodiments, the cancer in the subject is relapsed or refractory. In some embodiments, the cancer in the subject is chemoresistant.

Another embodiment of the present disclosure is a method for treating or ameliorating the effects of leukemia in a subject comprising administering to the subject a low dose of doxorubicin or pharmaceutically acceptable salt thereof, and a therapeutically effective amount of pembrolizumab.

In some embodiments, the leukemia in the subject is chemoresistant.

In some embodiments, the low dose of doxorubicin or pharmaceutically acceptable salt thereof is administered prior to pembrolizumab.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present disclosure may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population, may fail to respond or respond inadequately to treatment.

As used herein, the terms "ameliorate", "ameliorating" and grammatical variations thereof mean to decrease the severity of the symptoms of a disease in a subject.

As used herein, a "therapeutically effective amount" is an amount sufficient to effect beneficial or desired results. A therapeutically effective amount can be administered in one or more doses. The therapeutically effective amount is generally determined by a physician on a case-by-case basis and is within the skill of one in the art. Several factors are typically taken into account when determining an appropriate dosage. These factors include age, sex and weight of the subject, the condition being treated, the severity of the condition and the form of the drug being administered.

Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of animal, and like factors well known in the arts of medicine and veterinary medicine. In general, a suitable dose of an agent according to the disclosure will be that amount of the agent, which is the lowest dose effective to produce the desired effect. The effective dose of a agent may be administered as two, three, four, five, six or more sub-doses, administered separately at appropriate intervals throughout the day.

The following examples are provided to further illustrate the methods of the present disclosure. These examples are illustrative only and are not intended to limit the scope of the disclosure in any way.

EXAMPLES

The following experimental protocols were used in the Examples below.

Animals

Mice were housed in the animal facility at Stowers Institute for Medical Research (SIMR) and handled according to Institute and NIH guidelines. All procedures were approved by the IACUC of SIMR. The HSC-SCL-Cre-ER$^T$Pten$^{loxP/loxP}$βcat(Ctnnb1)$^{loxP(Exon3)/+}$ (hereafter, Pten:β-cat$^{Act}$) mouse model combines conditional deletion of LoxP flanked Pten, resulting in activation of the PI3K/Akt pathway, and exon 3 of β-catenin (β-cat$^{Act}$), resulting in constitutive activation of β-catenin (Lesche et al. 2002; Harada et al. 1999). The hematopoietic stem/progenitor cells (HSPCs)-specific Cre recombinase, HSC-SCL-Cre-ER$^T$, was used to study of the combined effects of both pathways starting with HSPCs and without the HSC activating effects of induction by interferon (Gothert et al. 2005). Primary HSC-SCL-Cre mice were induced by intra-peritoneal injection of tamoxifen daily for 5 days using 5 mg on day 1 and 2 mg on days 2-5 each dissolved in 0.1 ml of corn oil. A Bioruptor® sonicator was used to fully solubilize the tamoxifen. HSC-SCL-Cre was induced in transplant recipients by placing transplant recipients on tamoxifen feed (1 mg/g) for 2 weeks. HSC-SCL-Cre, Pten, and β-cat$^{Act}$, were obtained from Joachim Goethert (University of Duisburg-Essen, Germany), Hong Wu (UCLA, Los Angeles, CA), and Makoto Taketo (Kyoto University, Japan), respectively. TCF/Lef: H2B-GFP reporter mice were obtained from Anna-Katerina Hadjantonakis (Sloan-Kettering, NY, USA). This study is compliant with all relevant ethical regulations regarding animal research.

Transplantation Assays

Whole bone marrow was isolated from uninduced HSC-SCL-Cre$^+$ Pten$^{fx/fx}$ βcat$^{fx(Exon3)/+}$ (Pn:β-cat$^{Act}$) mice and combined with an equal portion of Cre negative bone marrow from a littermate and transplanted into irradiated (10 Grays) B6.SJL-Ptprc$^a$ Pepc$^b$/BoyJ (Ptprc) recipients. Recipients were placed on Tamoxifen feed 4-6 weeks post-transplant to induce recombination. resulting in leukemia development by 7-8 weeks post-induction in all recipient mice.

Limiting-dilution and tumorigenic assays were performed by establishing leukemic mice as described above and treating as indicated at 8 weeks post-induction. For limiting-dilution transplants, mice were treated with chemotherapy or [Low]DXR and, at 10 days post-treatment (based on first treatment), CD45$^{Hi}$CD3$^+$c-Kit-blast cells or Lin$^-$CD3$^+$c-Kit$^{Mid}$LSCs were sorted from chemotherapy treated mice and Lin-Sca-1$^+$c-Kit$^+$HSPCs were sorted from [Low]DXR treated mice. The indicated numbers of these populations were transplanted into 3.25 Gy irradiated NOD.Cg-Prkdc$^{scid}$Il2rg$^{tm1Wjl}$/SzJ (NSG) recipient mice. Recipient bone marrow was analyzed by flow cytometry at 10-12 weeks post-transplant and those with ≥1% CD45$^{Hi}$blast cells in bone marrow were considered engrafted. CRU frequency was determined using ELDA analysis (Hu et al. 2009).

Tumorigenic assays were performed by transplanting 0.5, 1.5, or $4.5 \times 10^4$ bone marrow cells from treated mice at 12 days post-treatment into 3.25 Gy irradiated NSG recipient mice. 10 recipients were used for each dose from each group. One male and one female donor was used for each group. Leukemia was assessed in mice euthanized due to poor health by analyzing CD45$^{Hi}$CD3$^+$ cell frequency. Mice having >20% Blasts in the bone marrow were considered leukemic. NSG and Ptprc mice were originally obtained from The Jackson Laboratory.

In Vitro Treatment

Bone marrow cells from leukemic mice at 8 weeks post-induction were cultured overnight at $5-20 \times 10^4$ cells per well in 96-well U-bottom tissue culture plates (Becton, Dickinson and Company; Cat. No. 353077) in HSC expansion media in low $O_2$ conditions as previously described (Perry et al. 2011). Doxorubicin (Sigma; D1515), 0105375 (University of Kansas CMLD compound), or Thioguanosine was mixed with HSC expansion media and added to the cultures to obtain final concentrations of 11, 33, 100 nM. Equivalent amounts of DMSO alone (vehicle control) were added to parallel cultures for comparison. Half-media changes were performed approximately every 24 hours. Cultures were analyzed after 72 hours exposure to the indicated drug.

In Vivo Treatment

Chemotherapy for the animal model consisted of Nelarabine (Selleck) and Dexamethasone (BioVision) administered daily for 5 days consecutively. 43.4 mg/ml Nelarabine was administered intravenously via the tail vain according to the formula: Body Weight (g)×5=volume to inject (µl), which yielded 217 mg/kg. 2.5 mg/ml Dexamethasone was injected intraperitoneally according to the formula: Body Weight (g)×4=volume to inject (µl), yielding 10 mg/kg. Targeted ([Low]DXR) treatment consisted of 5 consecutive daily doses at 0.5 mg/kg using Doxorubicin hydrochloride (Sigma; D1515) at 0.1 mg/ml injected intravenously via the tail vain according to the formula: Body Weight (g)×5=volume to inject (µl), which yielded 0.5 mg/kg (clinical DXR used 4.0 mg/kg). [Low] NanoDXR treatment used doxorubicin nanoparticles (Tran et al. 2014) administered as a single IV injection once per week on day 1 relative to above treatments using 0.8 mg/kg. Maintenance [Low] NanoDXR consisted of once per week injections of 0.4 mg/kg. Groups combining Nelarabine with Doxorubicin used a single injection containing both drugs. All drugs were solubilized in 45% (2-Hydroxypropyl)-p-cyclodextrin (HBC) or 0.9% NaCl.

For immune-checkpoint blocker treatment, 250 µg anti-PD-1 or isotype control (BioXcell) was injected intravenously every other day for a total of 3 injections. For CD8$^+$ T cell depletion, $2 \times 100$ µg and $1 \times 250$ µg of anti-CD8a or isotype control (BioXcell) was injected intravenously every other day.

Rationale for doxorubicin dosage: for clinical ALL therapy, doxorubicin is typically administered at a single dose every 21-28 days at 40-75 mg/m$^2$. Using 60 mg/m as the clinical equivalent dose, this is equivalent to 1.6 mg/kg for adult humans (60 mg/m$^2 \times 1$ m$^2$/37 kg=1.6 mg/kg). Converting to mouse, this is equivalent to ~20 mg/kg (1.6 mg/kg×12.3 ($k_{m(Human)}/k_{m(Mouse)}$)=19.7 mg/kg) ($k_m$ is Michaelis constant) (Freireich et al. 1966). Cumulatively, 2.5 mg/kg doxorubicin was administered and thus ⅛ the equivalent clinical dose spread over 5 days.

Clinical Trial

This was registered at clinicaltrials.gov (identifier NCT02914977). All patients provided informed consent according to institutional guidelines. At least two prior induction attempts were required for fit patients with primary refractory leukemia; unfit or relapsed patients were allowed entry with one prior therapy. There was no limit on number of prior therapies. Patients had an ECOG performance score of 0-3, adequate hepatic and renal function and cardiac ejection fraction ≥45%. Exclusion criteria included presence of acute promyelocytic leukemia, CNS leukemia or total lifetime anthracycline exposure exceeding the equivalent of 900 mg/m$^2$ of DNR. Treatment consisted of bone marrow aspiration for correlative studies followed by one cycle of low dose DNR (6.75 mg/m$^2 \times 5$ consecutive days, days 1-5) and second bone marrow aspiration on day 8. Effects on LSC population were measured by flow cytometry. Adverse events (AEs) and laboratory values were monitored for safety. This study is compliant with all relevant ethical regulations regarding research involving human participants and was approved by the Human Subjects Committee at the University of Kansas.

Preparation of Doxorubicin Nanoparticles (nanoDXR)

Self-assembled nanoparticles were prepared from new amphiphilic cholesterol-based brush-like block copolymers composed of polynorbonene bearing a cholesterol block and a poly(ethylene glycol) (PEG) block. DXR containing self-assembled nanoparticles were prepared from DXR and the newly developed amphiphilic cholesterol-based brush-like block copolymers using the reported methods (Tran et al. 2014). The mean particle size was 135.5±3.5 nm and the drug loading in the nanoparticles was 22%.

Flow Cytometry

Cells were collected from bone marrow (femur and tibia), spleen, peripheral blood, and thymus. For cell surface phenotyping, a lineage cocktail (Lin) was used including CD3 (for HSPC but not LSC analysis), CD4, CD8, Mac-1, Gr, B220, IgM, and Ter119 (eBioscience, San Diego, CA). Monoclonal antibodies against CD3 (separate fluorophore for LSC analysis), Sca-1, c-Kit, CD45.1, and CD45.2 were also used where indicated. Cell sorting and analysis were performed using an inFlux (BD), MoFlo (Dako, Ft. Collins, CO) and/or CyAn ADP (Dako, Ft. Collins, CO). Data analysis was performed using FlowJo software (Ashland, OR).

For FACS analysis using PE-conjugated monoclonal anti-pS552-β-catenin antibody, cells were washed twice after cell surface staining, resuspended in 250ul of BD Fixation/Permeabilization® solution, incubated for 20 minutes at 4°, washed 2× with 1 ml of 1×BD Perm/Wash Buffer®, resuspended with 100 ul 1×BD Perm/Wash Buffer®, added 1.0 ug/ul anti-pS552-β-catenin antibody per 100 ul solution containing up to 3 million cells, incubated 2 hours on ice with rocking (resuspended every 15 minutes), washed 2 times and resuspended in PBS+2% FBS for analysis. BM from β-cat knockout mouse was harvested at 2-3 weeks post-knockout induction and stained alongside other test samples.

Immunostaining

For monoclonal anti-pS552-β-catenin antibody IHC was done using standard techniques according to the following details: tissues were fixed in zinc formalin, antigen retrieval used citrate buffer for 15 min. at 90° C., cooled to room temp., washed in PBS, peroxidase activity was quenched with 0.3% $H_2O_2$ (peroxide) for 10 min., washed in PBS, non-specific blocking by 1× Universal Block© for 10 min. at room temp., washed in PBS, stained with 1:1000 dilution primary Ab., 1 hour at room temp., washed 3 times in PBS+0.05% Tween, 1:1000 anti-rat HRP secondary Ab. (note: HRP antibody diluent is PBS+1% BSA+0.1% gelatin+0.05% Tween), 30 min. at room temp., Wash 3 times in PBS, DAB reagent for 5 min., wash in ddH$_2$O, counterstained using light (20%) haematoxylin and eosin.

Computational Modeling

Comparative modeling was applied to predict the 3-D structures of β-catenin and Akt using MUFOLD and Modeller. Modeling accuracy was further improved by sampling multiple conformations and conducting comprehensive structure quality assessment. Docking between β-catenin and Akt was conducted using ZDock. We analyzed the distributions of docking scores and 3-D conformations, and compared the hydrogen bonds formed in individual docking conformation to select the best candidate out of top 100 predictions from ZDock. Similar methods were applied to dock β-catenin and doxorubicin. Several structure candidates from PDB for doxorubicin were possible. Considering the structural similarity and docking stability, PDB 151D was selected and used for FIG. 2G. Protein visualization was produced using PyMol.

FRET Assay

FRET measurement was performed by using the acceptor photobleaching method. Briefly, 293T cells were transfected with EGFP-AKT and mCherry-β-catenin (Addgene, #39531, #55001). A Perkin-Elmer Ultraview spinning disc system with a CSU-X1 Yokogawa disc was used for imaging. A 40×1.2 NA Plan-apochromatic objective was used, and emission was collected onto a C9100 Hamamatsu Photonics EM-CCD. EGFP was excited with a 488 nm laser, and emission was collected through a 500-555 nm band pass filter. mCherry was illuminated, and photobleached, with a 561 nm laser. Emission of mCherry was collected with a 580-650 nm band pass filter. 6 images of EGFP were acquired before and 8 images after bleaching of the mCherry with intense 561 nm light. After subtraction of camera background, the average intensity of EGFP in a region of interest spanning the bleached cell was determined in the 4 images before acceptor bleach (I1), or the 4 images after acceptor bleach (I2). FRET efficiency is reported as 1−(I1/I2). Calculations were based on >500 cell images.

High-Throughput Screening 243 compounds were selected from primary screening of the validation library (5040 compounds) drawn from CMLD (1920), Prestwick (1120) and MicroSource Spectrum (2000) and reconfirmed in a 10 concentration dose-response. Activity of compounds was tested against HEK-TOP cells vs. HEK FOP cells for inhibition of luciferase activity. The cytotoxicity profiles of the compounds were also tested using Cell Titer Glo assay (Promega) on HEK-TOP cell lines. The dose-response data was used to calculate the EC50 (Effective concentration of compounds resulting in 50% inhibition of luminescence or cytotoxicity) using non-linear regression analysis. Approximately 90 compounds showed from 2.2 to 3 fold differences in EC50 between the TOP and FOP cells. Of these 36 compounds showed a window between luminescence inhibition and cytotoxicity. The structures of compounds were analyzed by cheminformatics analysis and medicinal chemists identified 25 compounds for repurchasing as fresh powders. The repurchased compounds were used to treat the cells at compound concentrations that resulted in 90%, 50% and 25% inhibition of luminescence(EC50, EC50 and EC25), derived from the dose-response curves for luminescence inhibition in HEK Top cell line. The HEK cells and HEK Top cells were plated at 300,000 cells/well in 6 well plates and were treated in duplicate with EC90, EC50 and EC25 concentrations of the 25 repurchased compounds as well as three controls. After 48h of exposure, the cells were washed with PBS and flash frozen. The frozen cells were lysed directly in plates for Western analysis.

RNA-Seq

Figure 8:
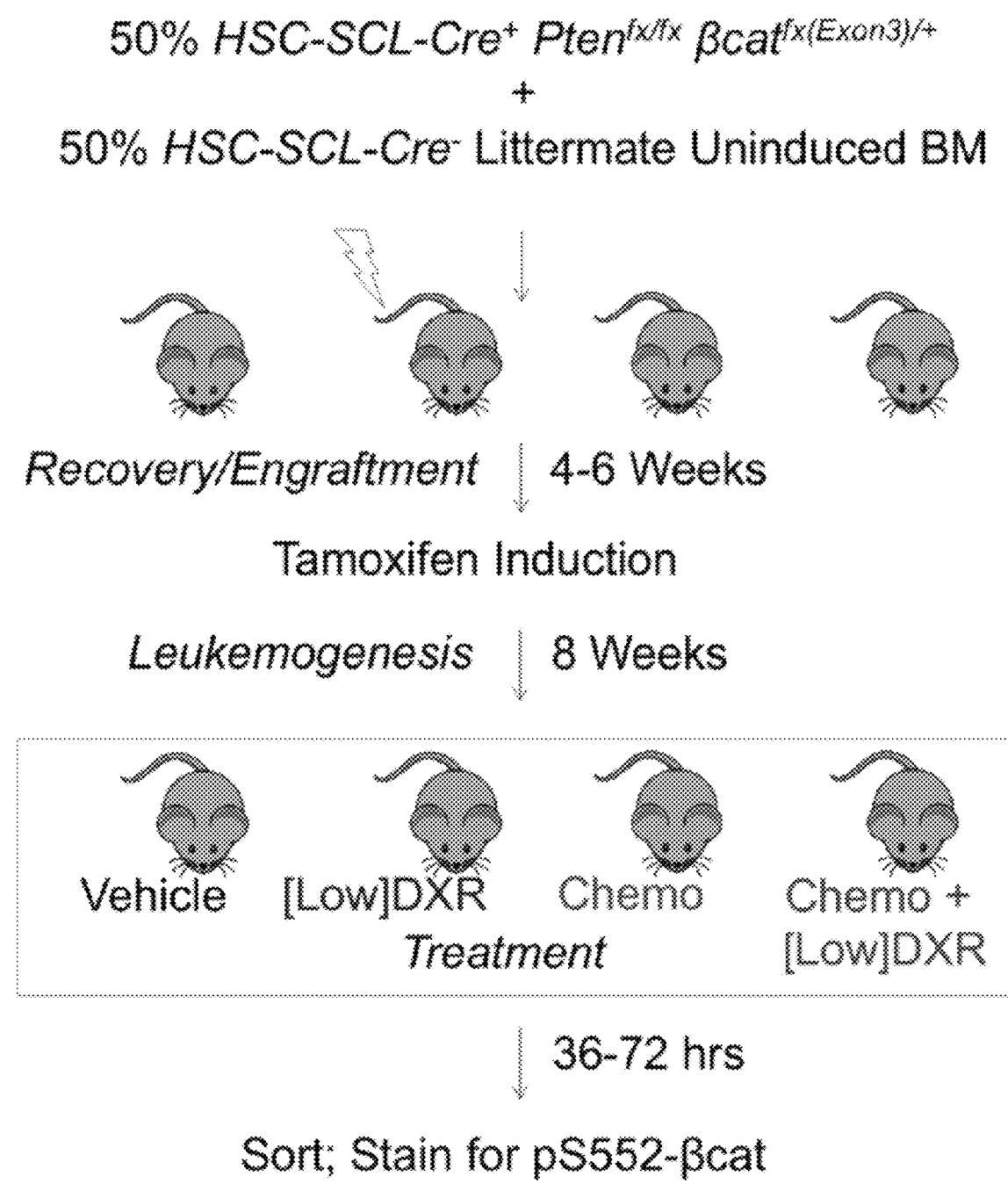
FIG. 8 provides the schematic representation of experimental setup and treatment scheme for leukemic mice.

Cohorts of leukemic mice were treated with vehicle, chemotherapy, [Low]DXR, clinical-dose DXR or chemotherapy+[Low]DXR as in FIG. 8. At 10 days post-treatment (day 1=start of treatment), blast cells, LSCs, and HSPCs were sorted using stringent gates (see FIG. 4A) for these populations. For each population, two biological replicates were made with 1-3 technical replicates each. Each biological replicate was a pool of sorted cells from 4-5 male and 4-5 female mice. Technical replicates were samples of sorted cells from each biological replicate. 1,000 cells per sample were sorted into 96-well plates with 7 µl lysis buffer containing RNase inhibitor (2 U/µl) from BM. First-strand cDNA synthesis and cDNA libraries were constructed using the SMARTer ultra low input RNA kit for sequencing—v3 (Clontech) following the manufacturer's instructions. cDNA quality was determined by Agilent high sensitivity DNA kit on Agilent 2100 BioAnalyzer (Agilent Technologies). Libraries were sequenced at 50 bp on the Illumina HiSeq 2500. Reads were aligned to UCSC mm10 with Tophat 2.1.1 (Kim et al. 2013), using gene models from Ensembl 80. Read counts per gene were obtained with HTSeq-count 0.6.0 (Anders et al. 2015). Analysis was done in R with the EdgeR package (Robinson et al. 2010) using default methods. Significantly changed genes were determined at FDR<1e-3 and fold change exceeding ±1.5. GO analysis was generated using significantly changed genes by Metascape (www.metascape.org). erated using significantly changed genes by Metascape (www.metascape.org). Data can be accessed at https://www.ncbi.nlm.nih.qov/geo/query/acc.cqi?acc=GSE105049.

Chromatin Immunoprecipitation and ChIP-qPCR

The Ctnnb1-3×Flag mouse ES cell line was provided by Andrew McMahon (University of Southern California) and routinely passaged and maintained on irradiated MEF feeder in conventional ES cell medium supplemented with 200 mg/ml G418 and 200 mg/ml Hygromycin B. Cells were adapted and expanded to serum free 2i culture for experiments. For serum-free 2i culture, ES cells were cultured without serum in the N2B27 medium: neurobasal medium (Invitrogen 21103-049), DMEM/F12 (Invitrogen 10565-018), 0.5×N2 (Invitrogen 17502-048), 0.5×B27 (Invitrogen 17504044), 1×b-mercaptoethanol(Millipore ES-007-E), 2 mM Lglutamine(Invitrogen 25030081), 100 mM non-essential amino acid(NEAA)(SCT 07600), 0.033% BSA(Invitrogen 15260037), 3 mM CHIRON(Tocris 4423), 1 mM PD03 (SCT72184).

A total of 2×10$^7$ ES cells were used per ChIP assay. Cells were washed with 1×PBS and crosslinked with 1% paraformaldehyde for 10 min at RT and quenched with 1 ml 2.5M glycine. Cells were washed with cold PBS three times and resuspended in 300 ml lysis buffer (15 mM HEPES at pH 7.5, 140 mM NaCl, 1 mM EDTA, 0.5 mM EGTA, 1% Triton X100, 0.1% sodium deoxycholate, 1% SDS, 0.5% N-lauroylsarcosine). The cell suspension was sonicated in Bioruptor Pico sonication device with the setting of 30 seconds on and 30 seconds off for 16 cycles followed with centrifugation at maximum speed for 10 min. The supernatant was saved and mixed with antibody coated protein G dynabeads (Invitrogen 10003D) at a ratio of 5 ml per 1 mg antibody for immunoprecipitation overnight at 4° C. The next day the protein G dynabeads were washed with 800 ml RIPA buffer three times (50 mM HEPES at pH7.5, 1 mM EDTA, 0.7% sodium deoxycholate, 1% IGEPAL CA-630, 0.5M LiCl). Each wash was 30 sec. 150 ml elution buffer and 150 ml 1×TE buffer were mixed with the dynabeads for 30 min at 65° C. After the elution, 4 ml RNase A(10 mg/ml) was then added with the beads being incubated at 37° C. for 2 hours, after which 2 ml Protease K(Invitrogen 20 mg/ml) was added and the beads were incubated at 55° C. for 2 hours. After the RNase A and Protease K treatment, the beads were incubated at 55° C. overnight for decrosslinking. The next day the DNA on beads was extracted by 300 ml phenol chloroform isoamyl alcohol (25:24:1) with centrifugation at 12,000 rpm for 5 min at RT. The supernatant was transferred to a new 1.5 ml tube with 12 ml of 5M NaCl and 2 ml glycogen (20 mg/ml). The DNA was precipitated by 750 ml cold 100% ethanol with at least 30 min incubation at −80° C. The sample was centrifuged for 30 min in 4° C. at maximum speed and the ethanol was decanted. The pellet was washed with 800 ml cold 70% ethanol, centrifuged and air dried. The DNA was resuspended in 55 ml nuclease-free water. ChIP-qPCR was performed with Fast SYBR™ Green Master Mix (Thermo Fisher Scientific 4385612) and analyzed with the Student's t-test.

ATAC-Seq

ATAC-seq was performed in LSCs and blast cells following the protocol described in Buenrostro et al., ATAC-seq: A Method for Assaying Chromatin Accessibility Genome-Wide. *Curr Protoc Mol Biol.* 2015 Jan. 5,109:21.29.1-9, the entirety of which is incorporated herein by reference. Cells were sorted from BM pooled from 20 leukemia mice treated with [Low]DXR and 8 leukemia mice treated with vehicle control at 15-30 k/replicate.

Collected cells were subject to transposition reaction and purification. In brief, 30,000 FACS-sorted blast cells were washed using 50 µl cold 1×PBS and centrifuged at 500 g for 5 min in a pre-chilled (4° C.) fixed-angle centrifuge. Cells were lysed using cold lysis buffer (10 mM Tris-HCl, pH 7.4, 10 mM NaCl, 3 mM MgCl$_2$ and 0.1% IGEPAL CA-630). Following the lysis, the pellet was resuspended in the transposase reaction mix. The transposition reaction mix contains 25 µl TD (2× reaction buffer), 2.5 µl TDE1 (Nextera Tn5 Transposase) and 22.5 µl Nuclease Free H$_2$O. Resuspended nuclei in the transposition reaction mix. Incubated the transposition reaction at 37° C. for 30 min. Immediately following transposition, purification was performed by using a Qiagen MinElute PCR Purification Kit. Eluted transposed DNA in 10 µl Elution Buffer (10 mM Tris buffer, pH 8). Transposed DNA fragments were amplified by PCR. The PCR mixture contains 10 µl transposed DNA, 10 µl Nuclease Free H$_2$O, 2.5 µl 25 µM Custom Nextera PCR Primer 1, 2.5 µl 25 µM Custom Nextera PCR Primer 2 (Contains Barcode) and 25 µl NEBNext High-Fidelity 2×PCR Master Mix. The thermal cycle is as follows: 1 cycle of 72° C. for 5 min, 98° C. for 30 sec, 5 cycles of 98° C. for 10 sec, 63° C. for 30 sec, 72° C. for 1 min. To reduce GC and size bias in PCR, the appropriate number of PCR cycles is determined using qPCR. To run a qPCR side reaction, combine the following in qPCR compatible consumables: 5 µl of previously PCR amplified DNA, 4.41 µl Nuclease Free H$_2$O, 0.25 µl 25 µM Customized Nextera PCR Primer 1, 0.25 µl 25 µM Customized Nextera PCR Primer 2, 0.09 µl 100×SYBR Green I, 5 µl NEBNext High-Fidelity 2×PCR Master Mix. Using a qPCR instrument, cycle as follows: 1 cycle of 98° C. for 30 sec, 20 cycles of 98° C. for 10 sec, 63° C. for 30 sec, 72° C. for 1 min. To calculate the additional number of cycles needed, plot linear Rn versus cycle and determine the cycle number that corresponds to ¼ of maximum fluorescent intensity. Run the remaining 45 µl PCR reaction to the cycle number determined by qPCR. Cycle as follows: 1 cycle of 98° C. for 30 sec, N cycles (determined using qPCR) of 98° C. for 10 sec, 63° C. for 30 sec, 72° C. for 1 min.

Primers used were:
Ad1_noMX,
(SEQ ID NO: 1)
AATGATACGGCGACCACCGAGATCT
ACACTCGTCGGCAGCGTCAGATGTG;

Ad2.1,
(SEQ ID NO: 2)
TAAGGCGACAAGC
AGAAGACGGCATACGAGATTCGCCTTAGTCTCGTGGGCTCGGAGATGT;

Ad2.2,
(SEQ ID NO: 3)
CGTACTAGCAAGCAGAAGACGGCATACGAGATCTAGTACGGTCT
CGTGGGCTCGGAGATGT;

Ad2.3,
(SEQ ID NO: 4)
AGGCAGAACAAGCAGAAGACGGCATACGAGATTTCTGCCTG
TCTCGTGGGCTCGGAGATGT;
and Ad2.4,
(SEQ ID NO: 5)
TCCTGAGCCAAGCAGAAGACGGCATACGAGATGCTCAGGAGTCTCGT
GGGCTCGGAGATGT.

Amplified library was purified using Qiagen MinElute PCR Purification Kit. Eluted the purified library in 20 µl Elution Buffer (10 mM Tris Buffer, pH 8). Be sure to dry the column before adding elution buffer. Optionally, prior to purification, amplified libraries can be visualized using gel electrophoresis. Adding 0.6×SYBR Green I to libraries provides excellent signal-to-noise without the need for post-staining. Routinely loaded 15 ng of 100 bp NEB ladder with 0.6×SYBR Green I as a DNA marker. Any instrument containing a blue-light source or imaging systems equipped with a laser that emits at 488 nm can be used to visualize DNA stained with SYBR Green I dye. Images are best obtained by digitizing at 100 microns pixel size resolution with a 520 nm band-pass emission filter to screen out reflected and excitation light and background fluorescence. The library was size-selected with BluePippin DNA Size Selection kit with 1.5% Agarose Gel Cassette.

Patient-Derived Xenografts

All patient samples were obtained under research ethics board approval with informed consent. Pediatric patient BM was transplanted into NSG mice. When 1° transplant mice succumbed to leukemia, bone marrow was harvested, frozen for later use, and transplanted into a larger set of 2° NSG recipients. At 2 weeks post-transplant, 2° recipients were treated once per week with vehicle or [Low]nanoDXR (week 1) and maintenance [Low]nanoDXR (weeks 2-10). NSG mice were irradiated with 3.25 Gy on the day of transplantation. Recipients were placed on Baytril® water 3 days prior to irradiation, which was maintained thereafter. Health was monitored independently by technicians blinded to any hypothetical outcome. Cells were frozen in liquid N2 using 10% DMSO, 50% FBS, and 40% PBS.

Statistical Analyses

Data expressed as mean±standard deviation. Pair-wise comparisons performed using Student's t-test. Log rank (Mantel-Cox) test was used for Kaplan-Meier survival. Statistical significance was defined as $p<0.05$.

Example 1

Figure 1B:
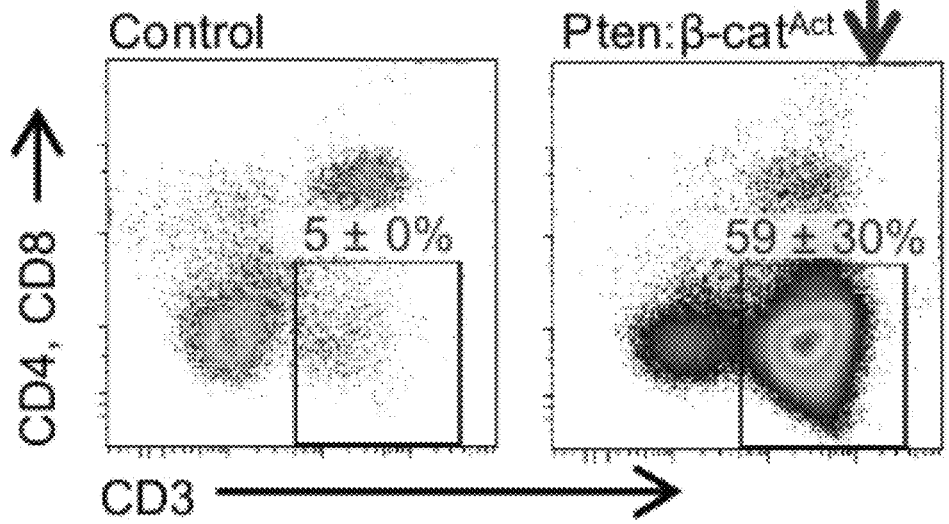
Figure 1C:
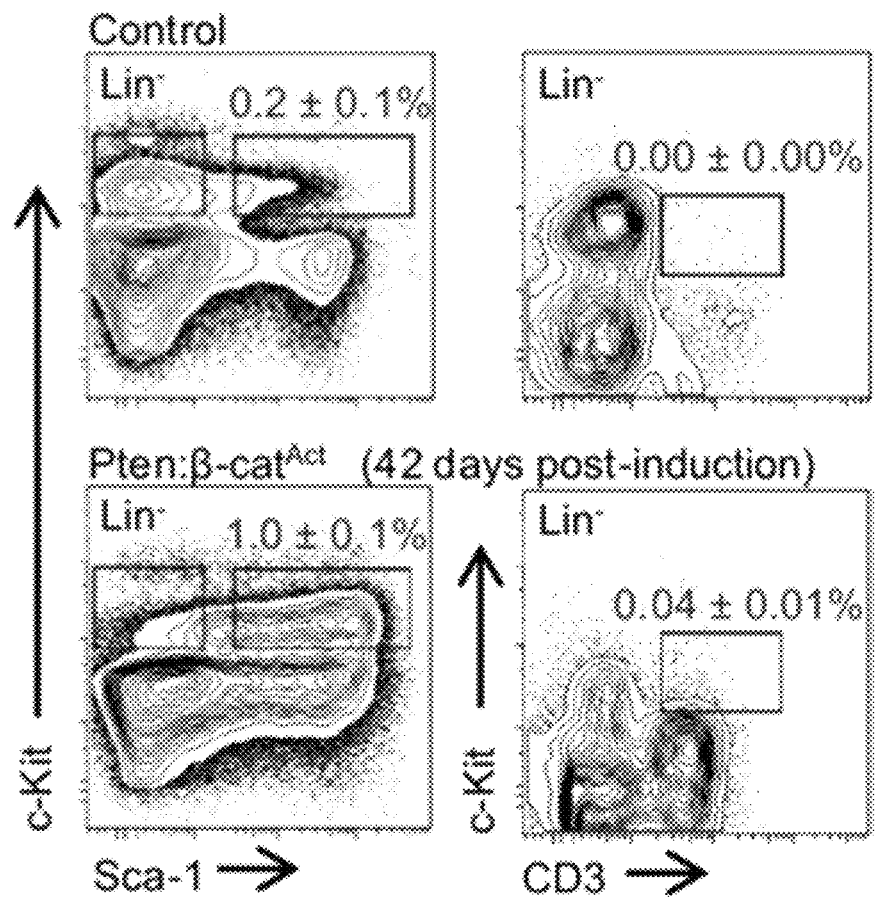
Figure 1D:
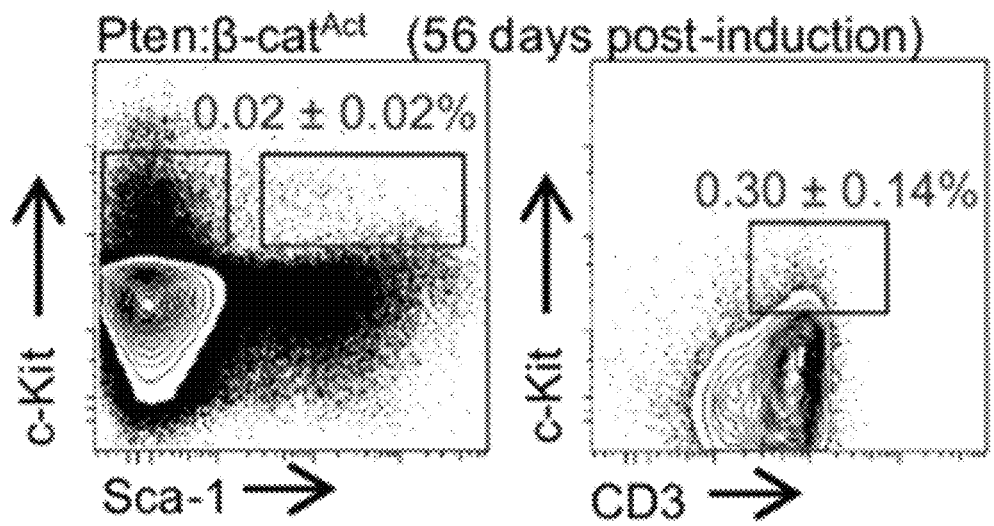
Figure 1E:
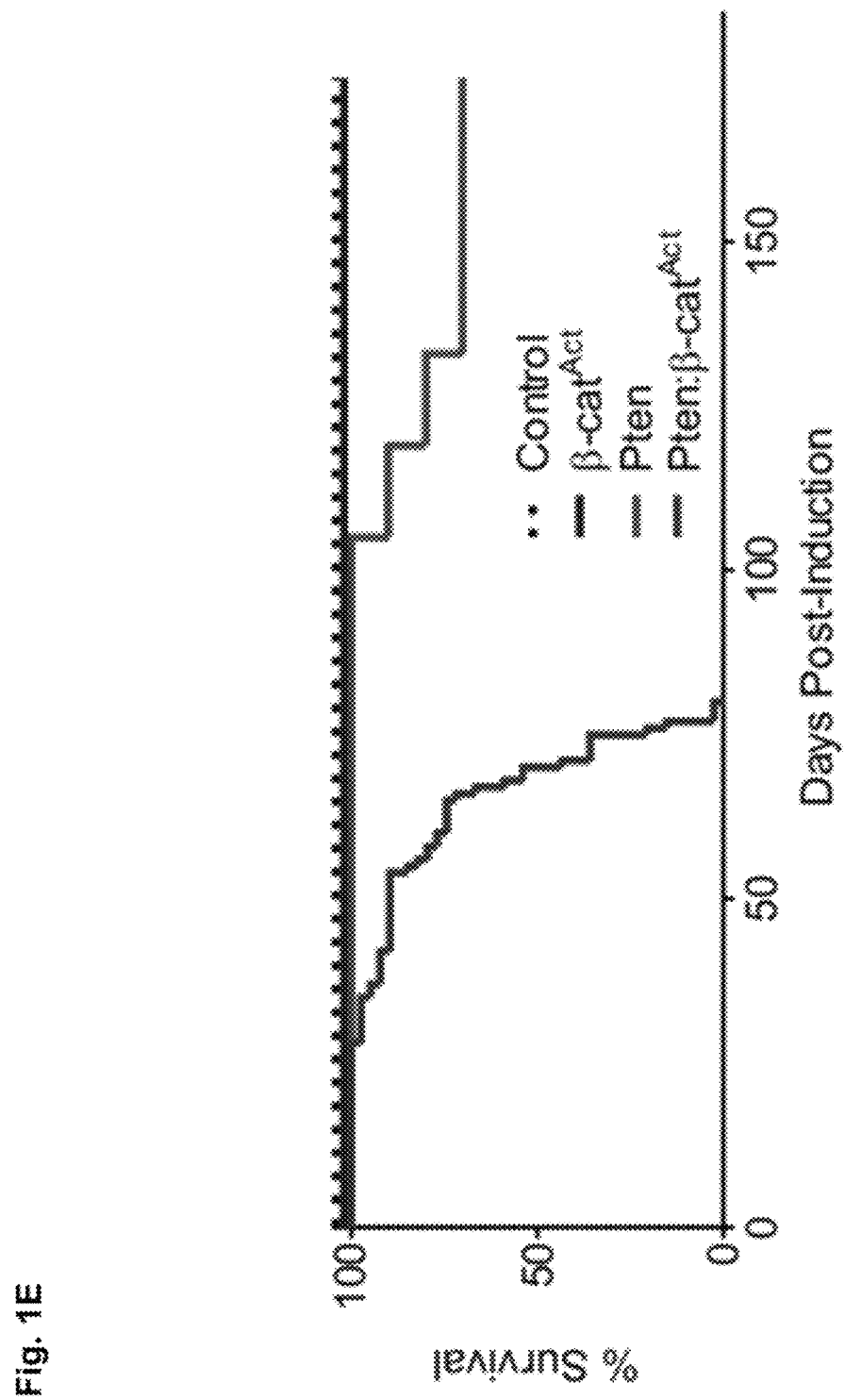

Simultaneous Activation of Wnt/β-Catenin and PI3K/Akt Pathways Results in Successive Expansion of HSPCs, LSCs and Blast Cells Previous work showed that cooperative activation of the Wnt/β-catenin and PI3K/Akt pathways drove self-renewal but resulted in leukemic transformation (Perry et al. 2011; Guo et al. 2008). Here, we explored the ontogeny and nature of leukemogenesis in Pten:β-cat$^{Act}$ mice that activate both pathways specifically in HSPCs by using HSC-SCL-Cre-ER(T) (Perry et al. 2011; Gothert et al. 2005). As with comparable studies using similar systems (Kaveri et al. 2013; Guo et al. 2008), Pten:β-cat$^{Act}$ double mutants developed T cell acute lymphoblastic leukemia (T-ALL), indicated by >20% CD45$^{hi}$ leukemic blasts, which expressed CD3 (FIG. 1A and FIG. 1B). To trace the ontogeny, we analyzed BM at earlier time points for HSPCs (lineage$^-$ Sca-1+c-Kit$^+$) and LSCs. T-ALL LSCs driven by overactivation of β-catenin have been well-characterized as Lin$^-$ CD3+c-Kit$^{Mid}$ cells (Guo et al. 2008; Schubbert et al. 2014), which we also confirm below. We found a striking accumulation of HSPCs in double mutants at 6 weeks post-induction (wpi) with commensurate reduction in more mature (Lin$^-$ c-Kit$^+$ Sca-1-) progenitor cells consistent with broad differentiation blockage (FIG. 1C; see Perry et al. 2011 for further details). At the same time rare LSCs at 6 wpi became more frequent by 8 wpi as the HSPC population collapsed (FIG. 1D). By 12 wpi, all double mutant mice succumbed to leukemia (FIG. 1E). This rapid and consistent leukemia development was unique to double mutants. Collectively, these data demonstrate that cooperative activation of the Wnt/β-catenin and PI3K/Akt pathways drive the progressive expansion of phenotypic HSPCs with transformation to LSCs resulting in leukemogenesis.

Example 2

DXR Targets Akt:β-Catenin Interaction

Figure 2A:
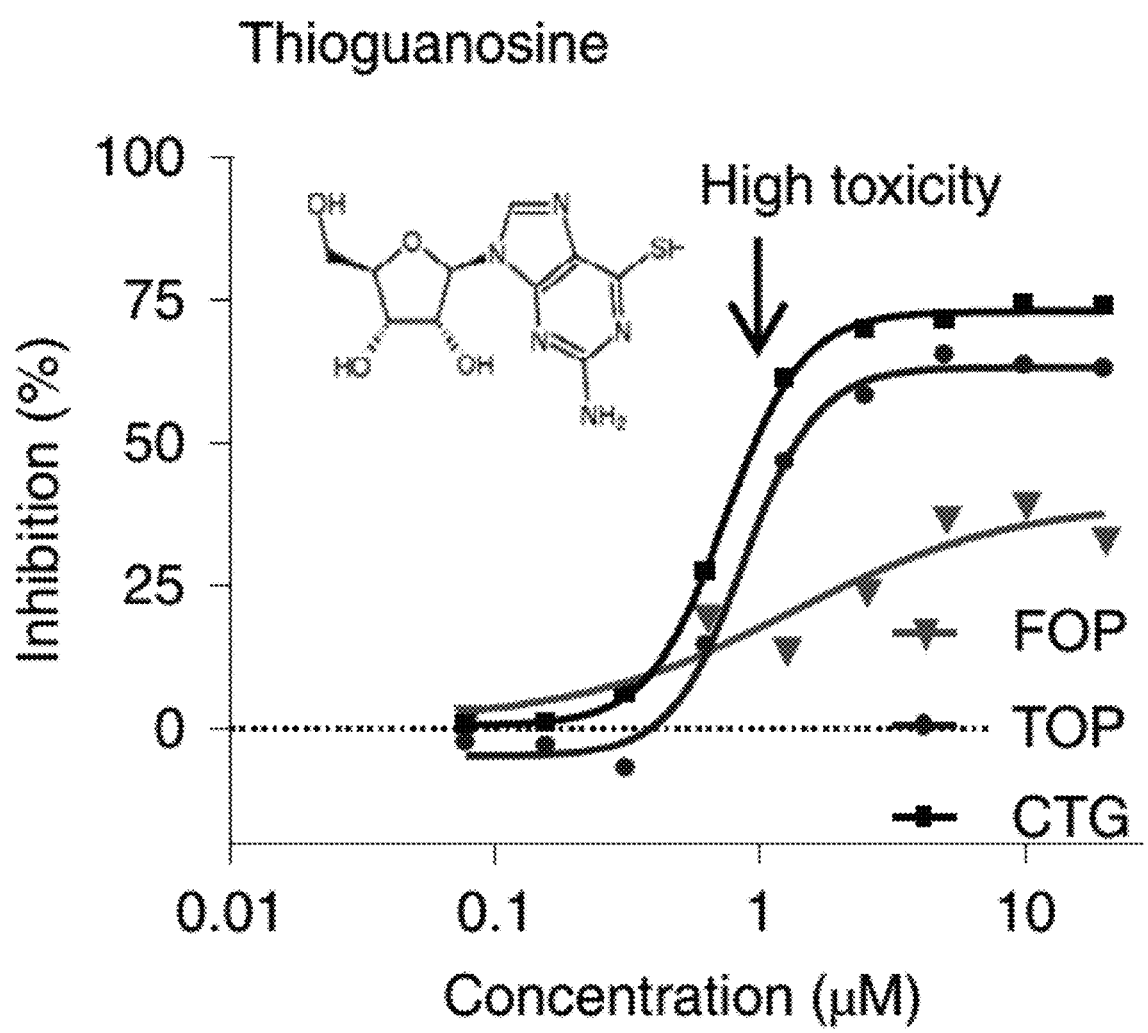
FIGS. 2A-2I show that DXR inhibits β-catenin activated by Akt.
Figure 2B:
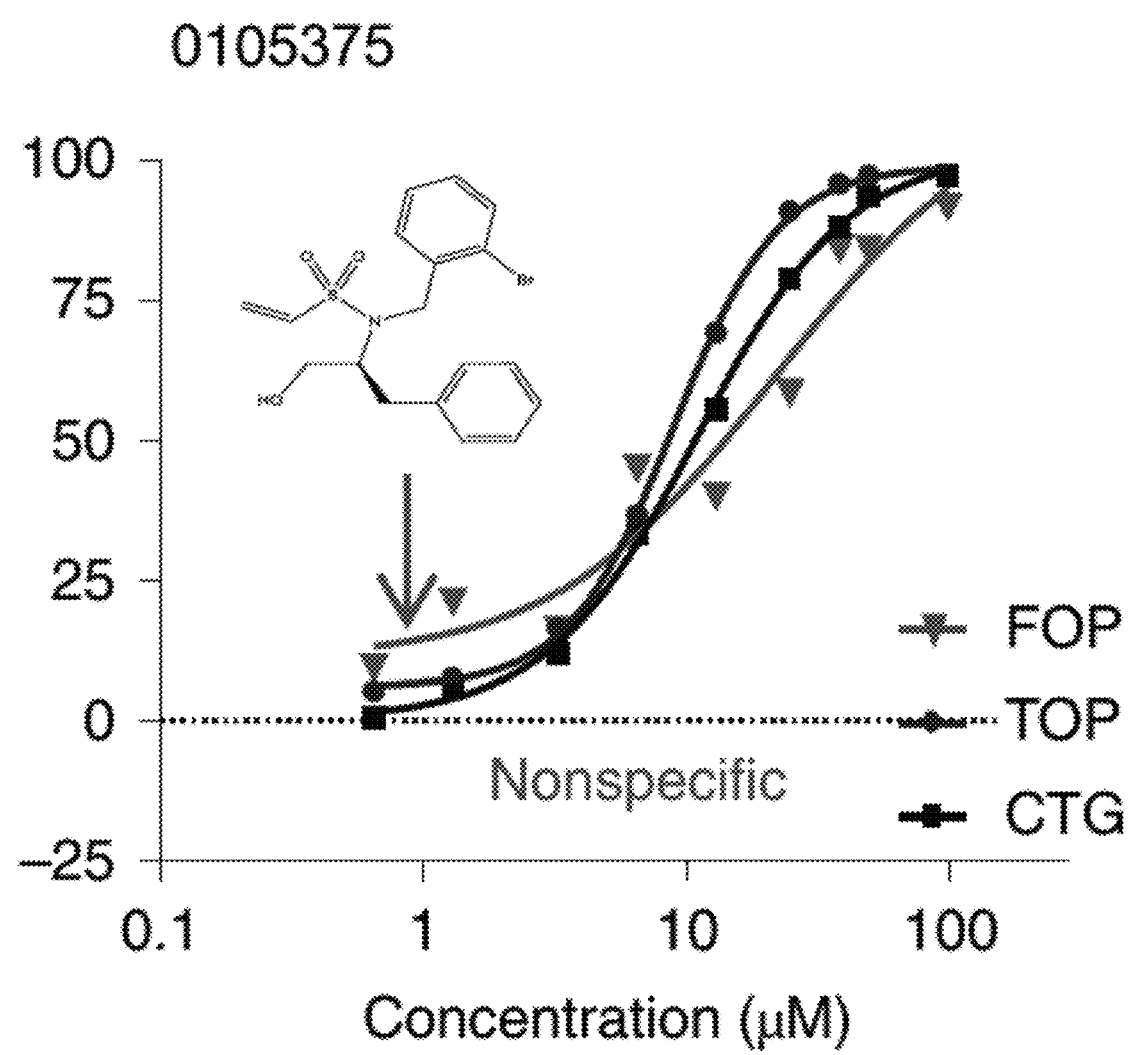
Figure 2C:
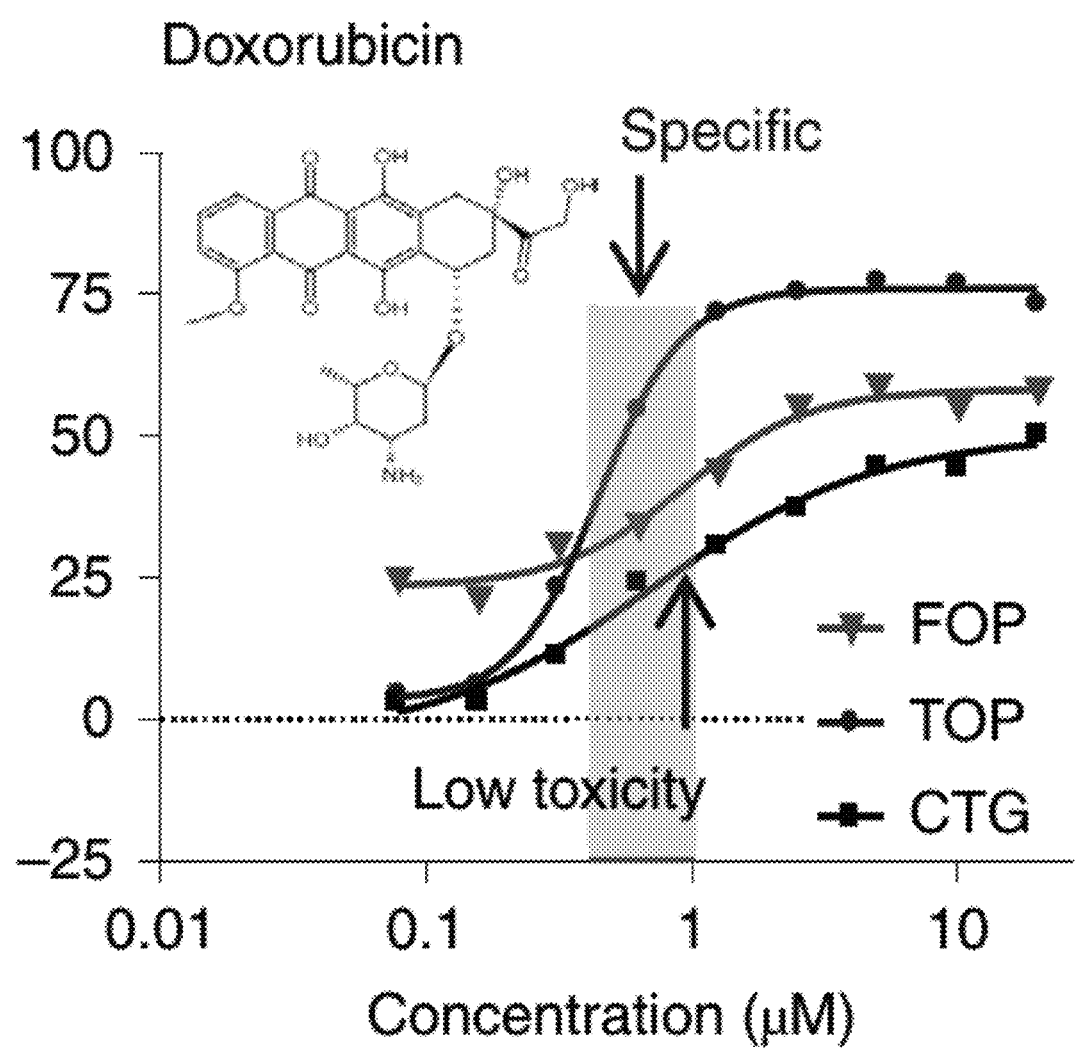
Figure 2D:
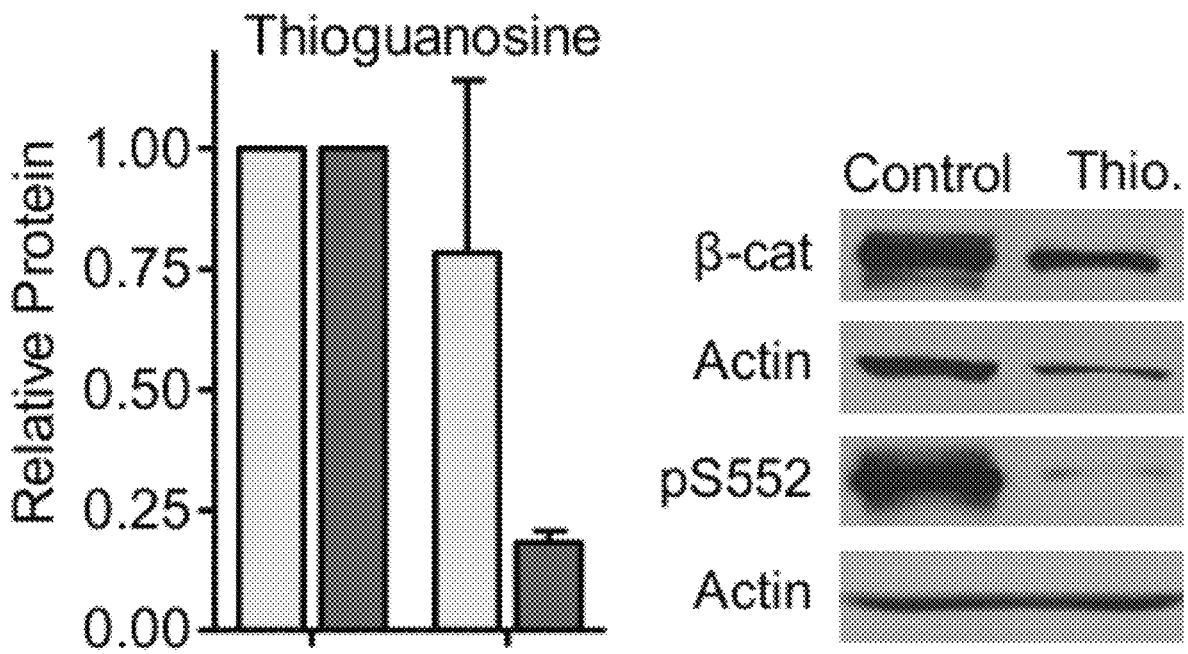
Figure 2E:
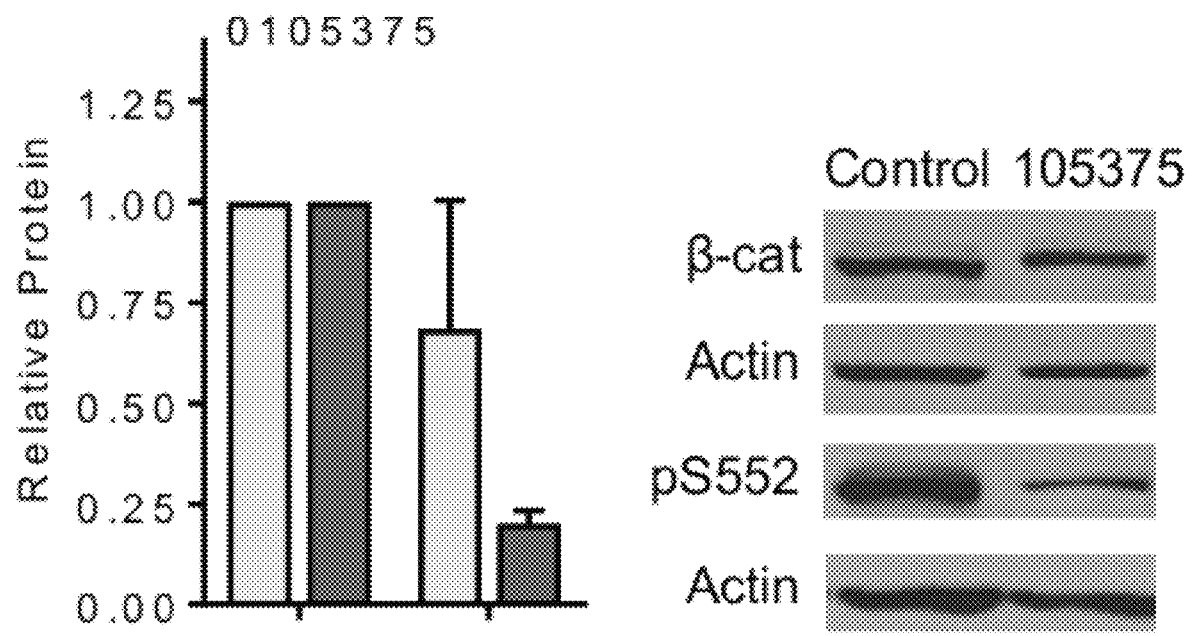
Figure 2F:
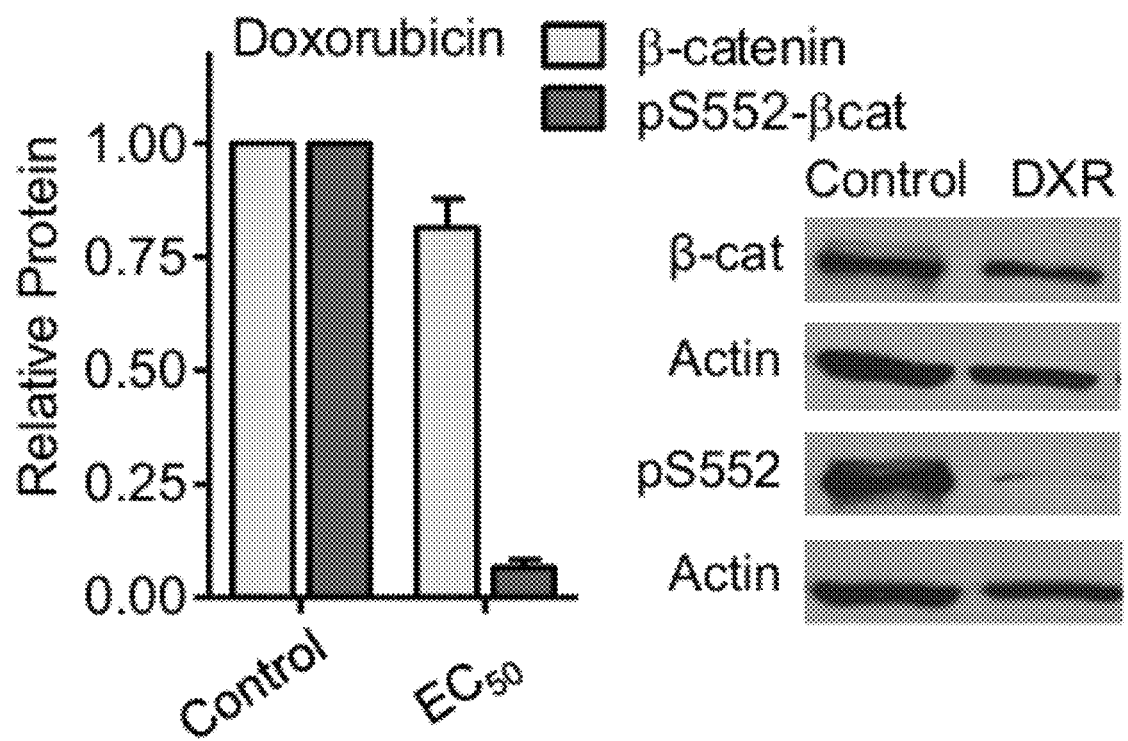
Figure 2G:
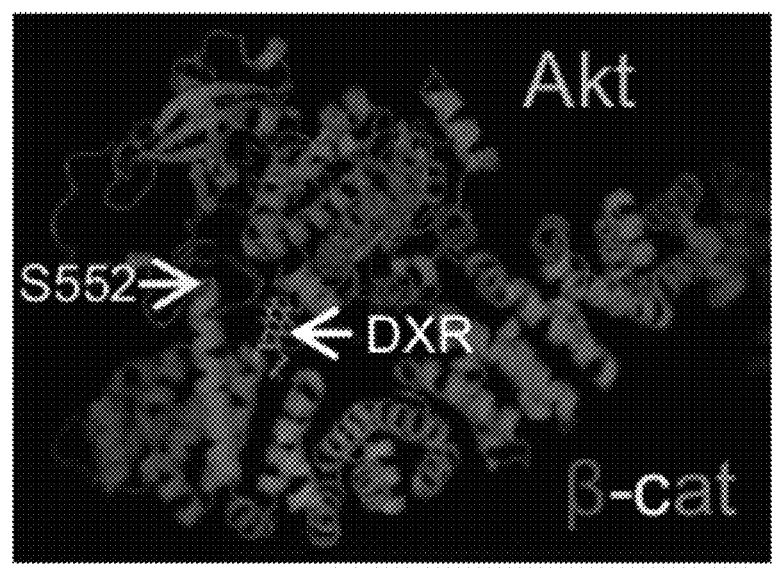
Figure 7A:
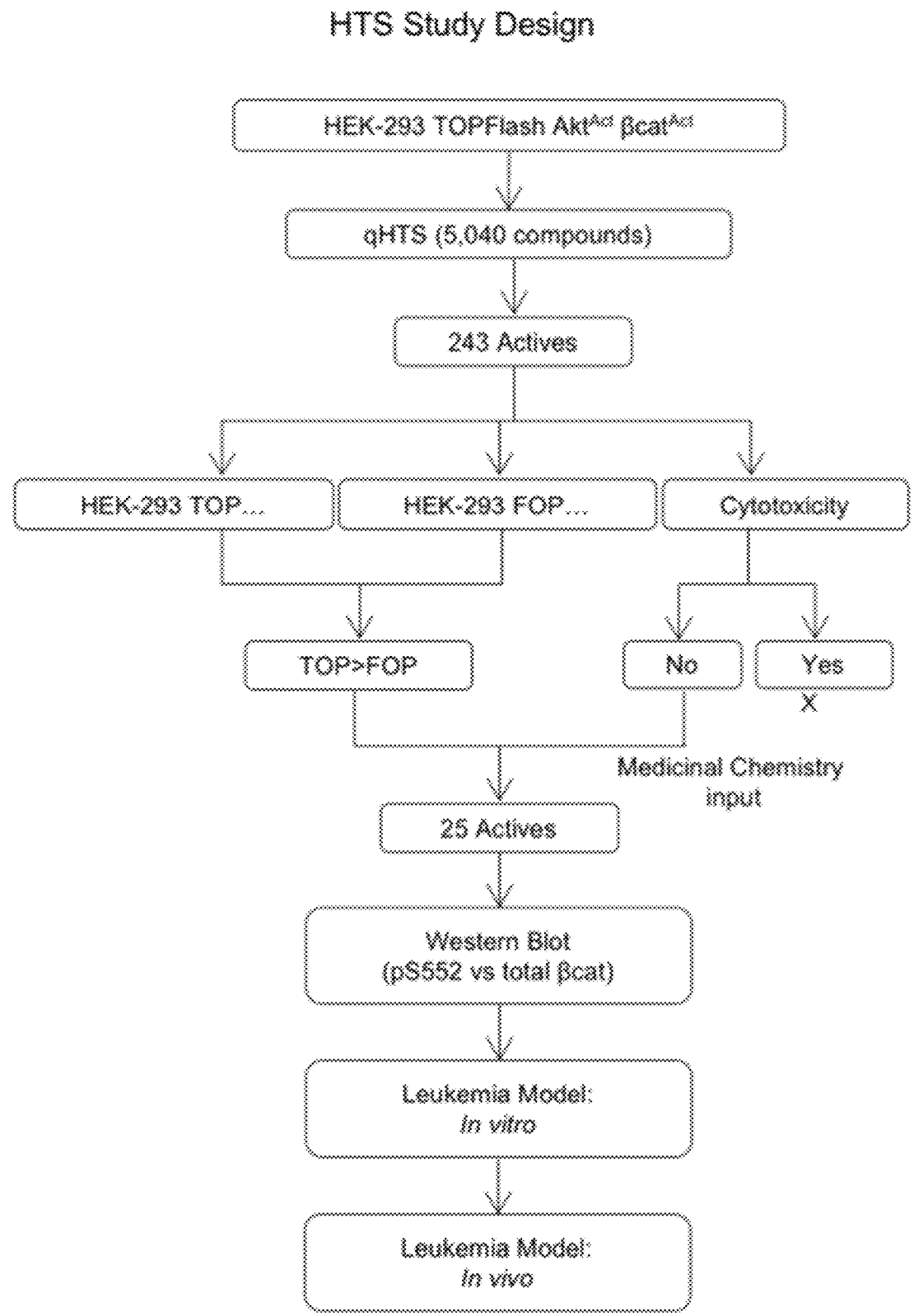

Since pharmacological activation of the Wnt/β-catenin and PI3K/Akt pathways in normal HSCs synergistically expands functional HSCs (Perry et al. 2011), we tested whether inhibition of this cooperation could reduce LSCs. Given the development of resistance to PI3K and Wnt pathway inhibitors shown by previous studies (Ciraolo et al. 2011; Cully et al. 2006; Fruman et al. 2014; Tenbaum et al. 2012), we focused on inhibiting the pS$^{552}$ active form of β-catenin to target the cooperative activity of the pathways more specifically. HTS of an FDA approved small molecule library identified candidates (FIG. 7A and FIG. 7B), which were narrowed to 3 compounds that could inhibit pS$^{552}$-β-catenin with less effect on pan β-catenin: thioguanosine, 0105375, and DXR (FIGS. 2A-2C). Although thioguanosine inhibited Akt-enhanced β-catenin activity (TOP-Luc) specifically (compare to FOP-Luc control) at concentrations:1 µM, it had high levels of toxicity (CTG) even at low concentrations (FIG. 2A). The specific inhibitory effect on Akt-enhanced β-catenin activity by the novel compound 0105375 occurred only at high concentrations where high toxicity was also observed (FIG. 2B). Most promising was DXR, which specifically inhibited Akt-enhanced β-catenin activity at lower than 1 µM concentration; however, higher concentrations showed reduced specificity (increasing FOP-Luc) and increased toxicity (FIG. 2C). Furthermore, pS$^{552}$-β-catenin was inhibited while having only minimal effect on P-catenin generally, particularly by low concentrations of DXR (FIGS. 2D-2F). Computational docking indicated that DXR binds to Akt and interferes with Akt's ability to phosphorylate β-catenin at the C-terminal S$^{552}$ site (FIG. 2G).

Figure 2H:
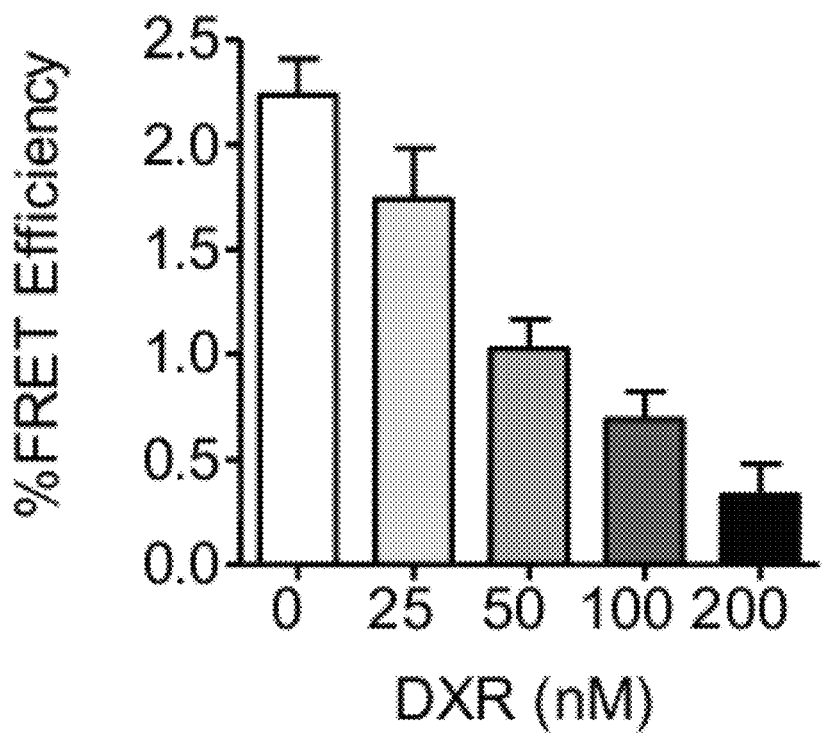
Figure 2I:
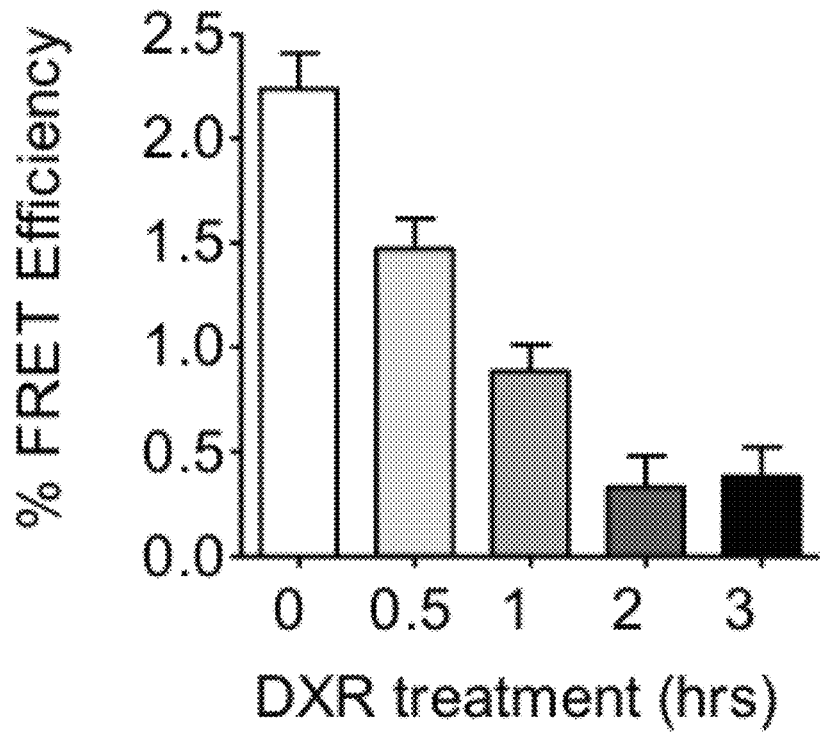
Figure 7C:
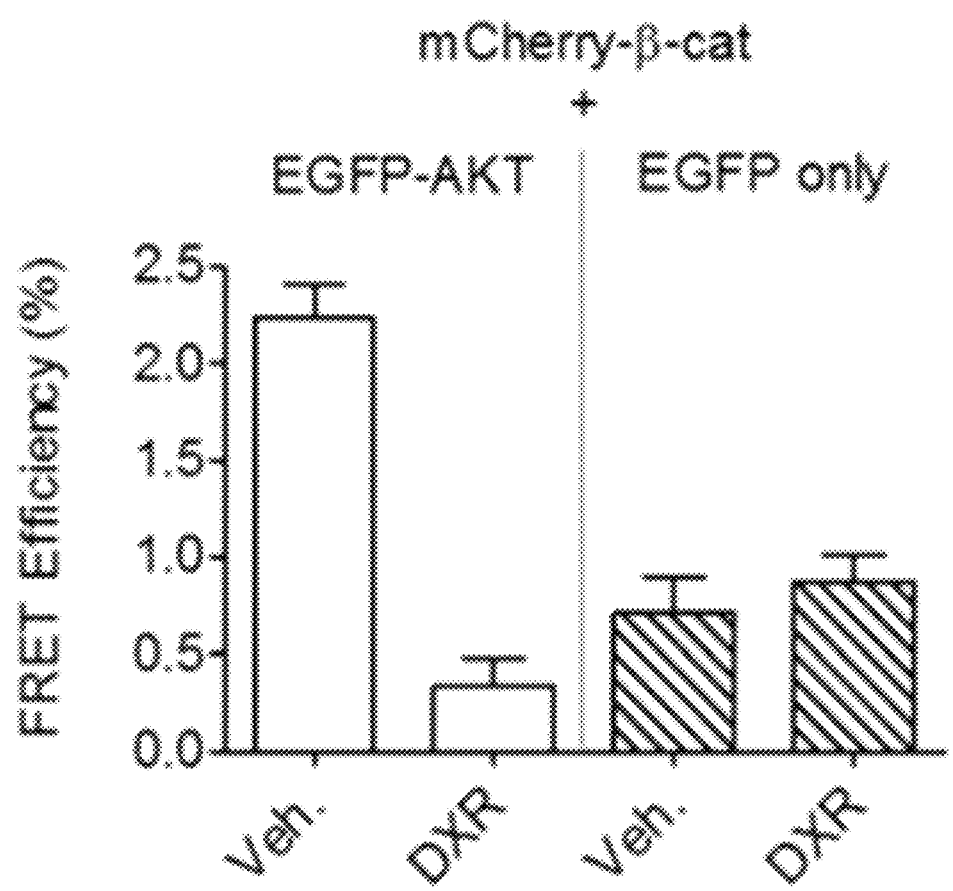

To further test whether DxR blocked interaction between Akt and P-catenin, we performed Fluorescence Resonance Energy Transfer (FRET) analysis using EGFP-AKT and mCherry-β-catenin transfected cells. FRET occurred in vehicle treated cells, which demonstrated Akt:β-catenin interaction, but decreased with increasing concentrations and exposure time to DXR (FIG. 2H and FIG. 2I). However, cells transfected with EGFP only and mCherry-β-catenin showed no discernible FRET and no difference in vehicle vs. DXR treatment (FIG. 7C). These data further indicate that Akt interacts with β-catenin and that DXR inhibits this interaction at <1 µM concentrations.

Figure 7D:
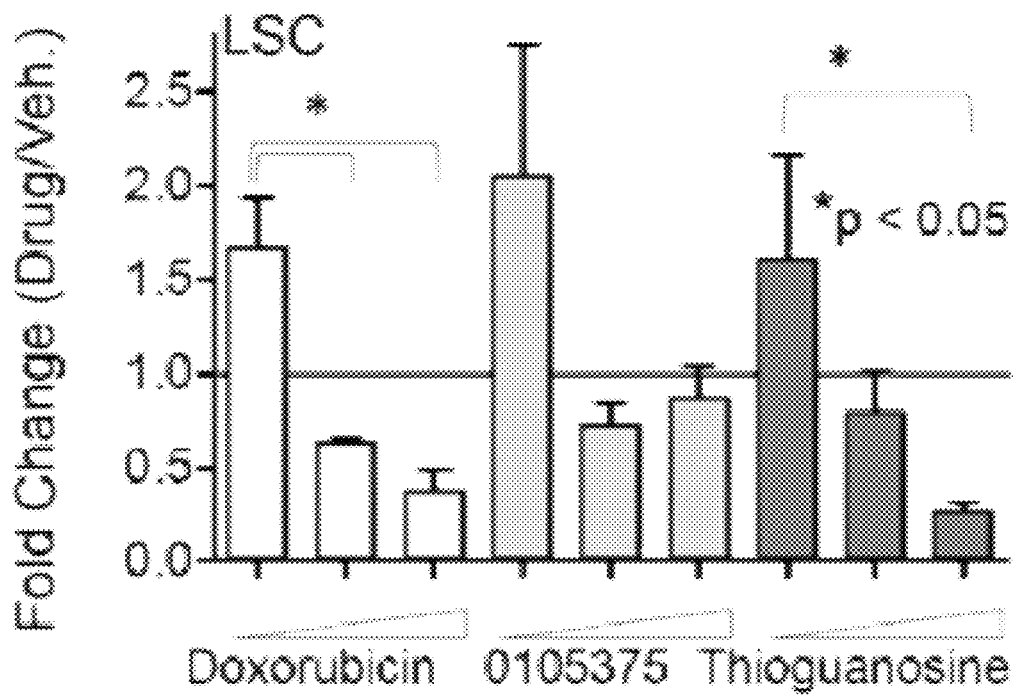
Figure 7E:
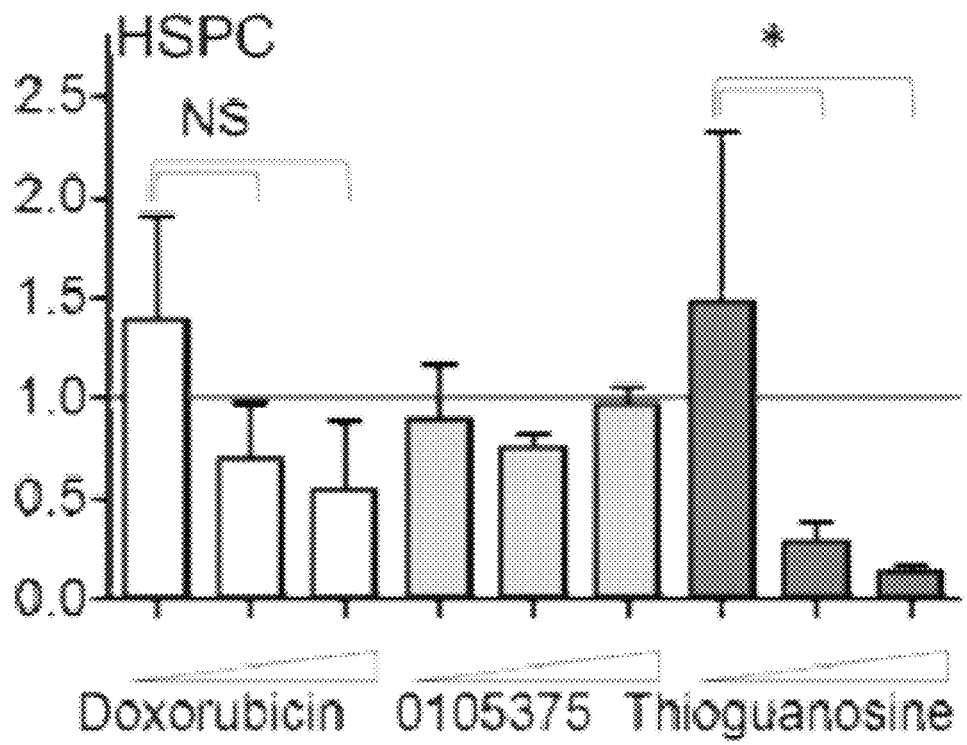

We then tested the effects of these candidate drugs on BM cells isolated from leukemic double mutants in vitro. Relative to vehicle, DXR significantly reduced LSCs but had a lower effect on HSPCs (FIG. 7D and FIG. 7E). Thioguanosine significantly reduced not only LSCs but also HSPCs and 0105375 had less potency than DXR, so we focused our in vivo studies on DXR. Together, these data show that DXR can inhibit Akt:β-catenin interaction at relatively low doses with minimal effects on total β-catenin; however, at higher doses, DXR is associated with increased non-specificity and cytotoxicity.

Example 3

Figure 3A:
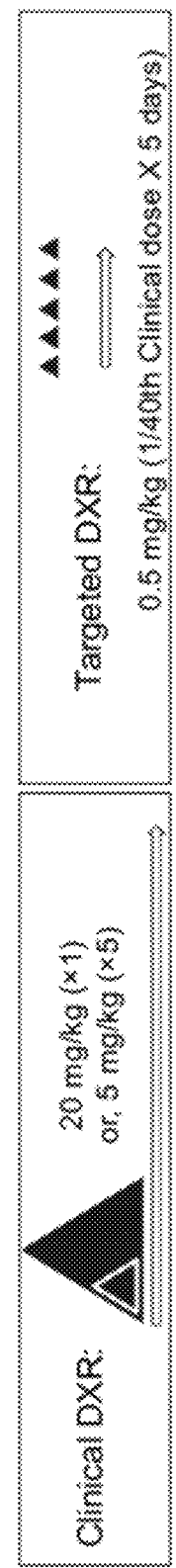

Low-Dose DXR Treatment Selectively Targets LSCs Expressing Akt-Activated p-Catenin, which Expand in Response to Chemotherapy We next determined whether DXR could be repurposed as a targeted treatment rather than a broadly cytotoxic chemotherapeutic agent in vivo using cohorts of leukemic mice (FIG. 8). To target Akt:β-catenin interaction, after testing different doses, we used doses well below the typical clinical dose, termed targeted or [Low]DXR (FIG. 3A). We next determined the differential effects of chemotherapy and targeted/[Low]DXR on blast cells, LSCs, and HSPCs. As expected, chemotherapy (see Supplemental Methods) substantially reduced blast cells; however, it also induced expansion in LSCs compared to control. Importantly, [Low]DXR significantly reduced LSCs, although it alone had no significant effect on blast cells (FIG. 3B). These results are consistent with a more specific, less broadly cytotoxic role for [Low]DXR treatment. Overall, chemotherapy and [Low]DXR displayed dichotomous effects on these populations, with chemotherapy targeting blast cells but inducing LSC expansion, whereas [Low]DXR specifically reduced LSCs. In combination, this treatment reduced blasts, prevented LSC expansion, and reduced LSCs while allowing for HSPC recovery (FIG. 3B).

Figure 3D:
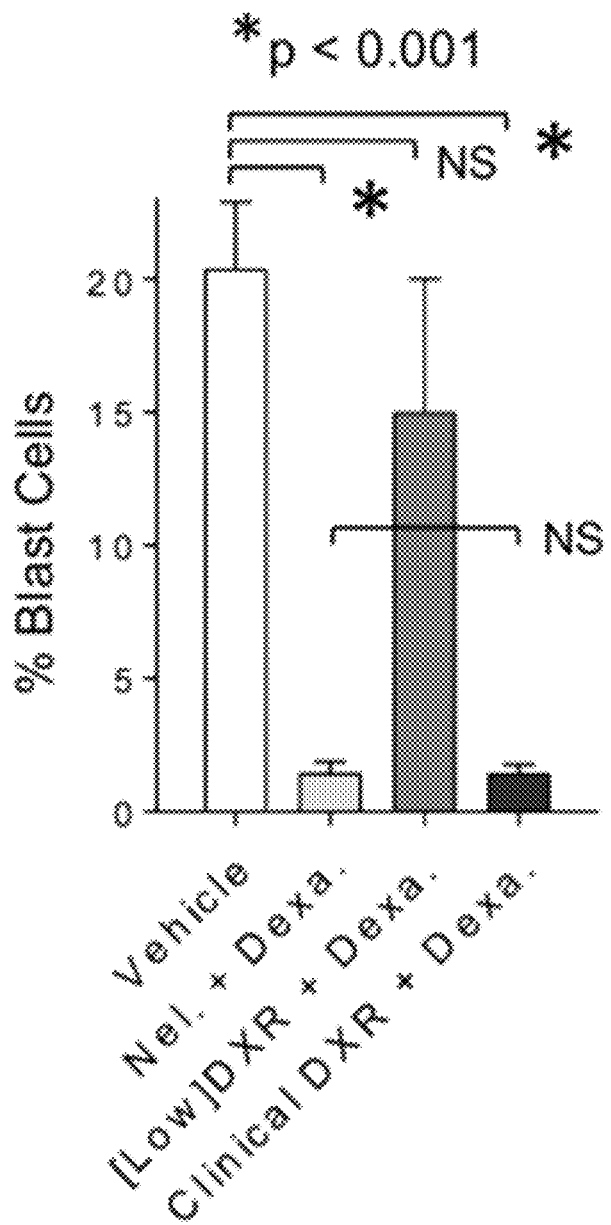

In contrast, clinical dose DXR (20 mg/kg) alone was broadly toxic to all cells in terms of absolute number, especially HSPCs. However, among the surviving cells, the frequency of blast cells was increased <2-fold while LSC frequency increased 5-fold but HSPC frequency was not significantly different from vehicle alone. As chemotherapy agents are given in combination, we tested whether DXR could substitute for the DNA damaging agent in our chemotherapy regimen. While [Low]DXR did not significantly reduce blast cells, the clinical equivalent dose of DXR could substitute for a DNA-damaging agent in their reduction (FIG. 3D). These data indicate that low-dose and clinical-dose DXR treatment have substantially different effects, with broad overall toxicity of clinical DXR but more LSC-targeting specificity of [Low]DXR, including the chemoresistant LSCs which expanded under chemotherapeutic stress.

Figure 3E:
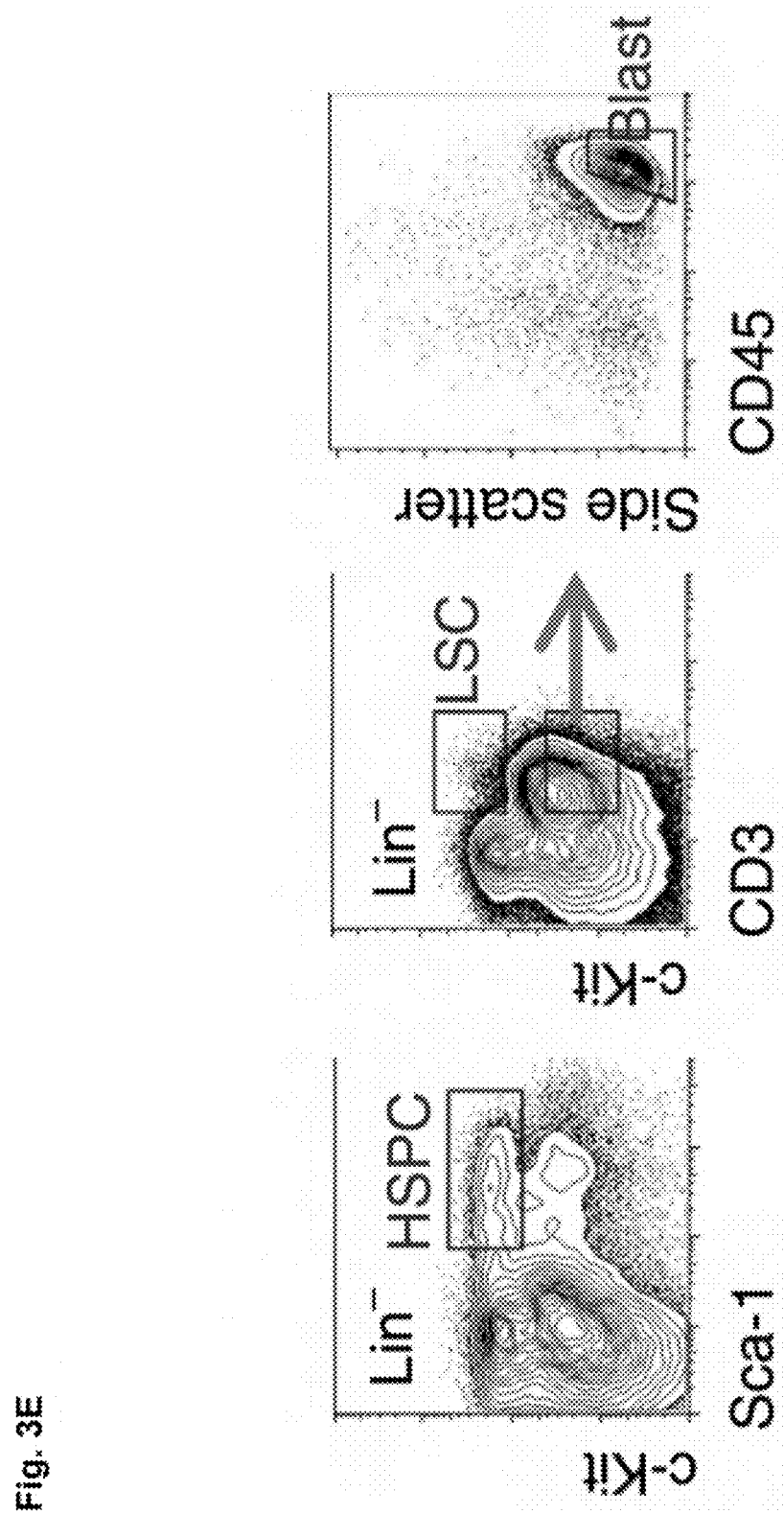
Figure 3F:
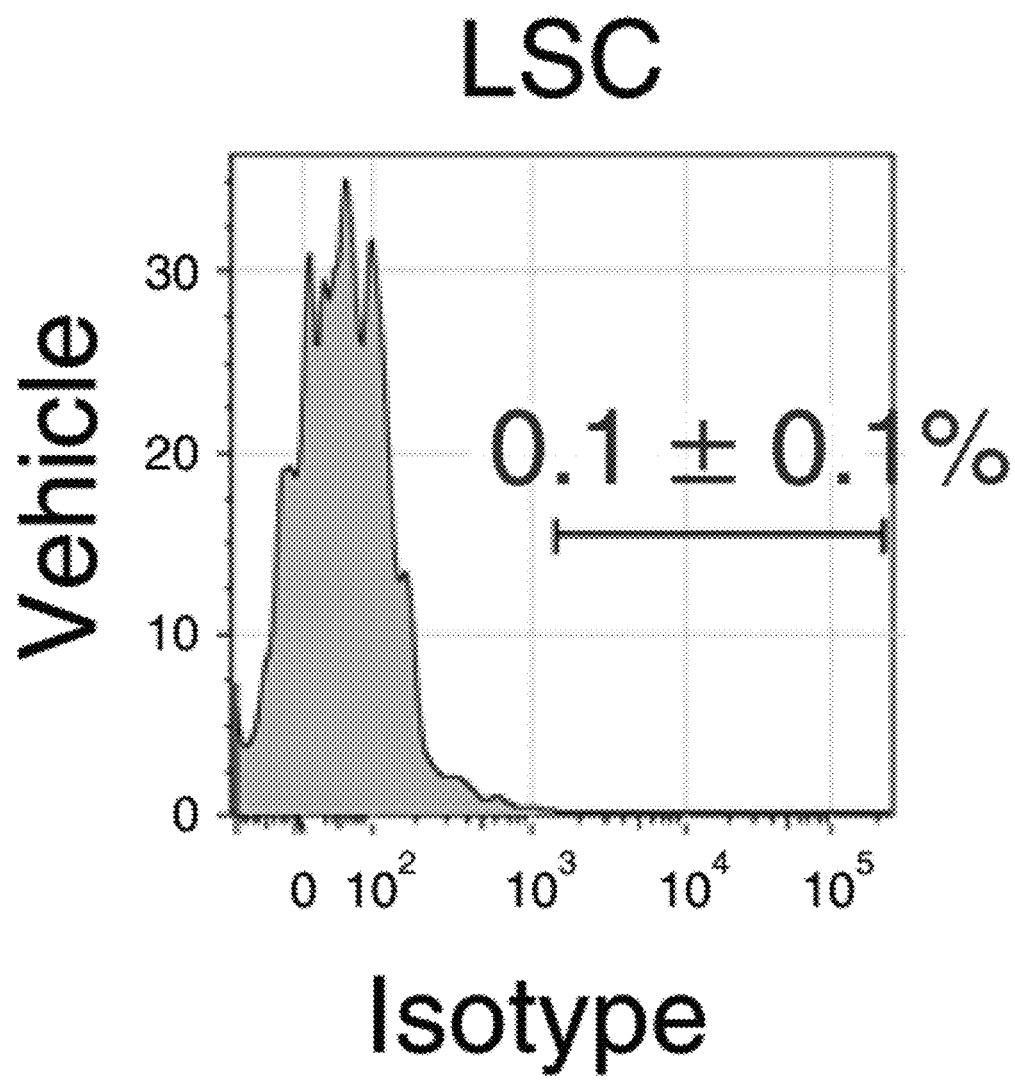
Figure 3G:
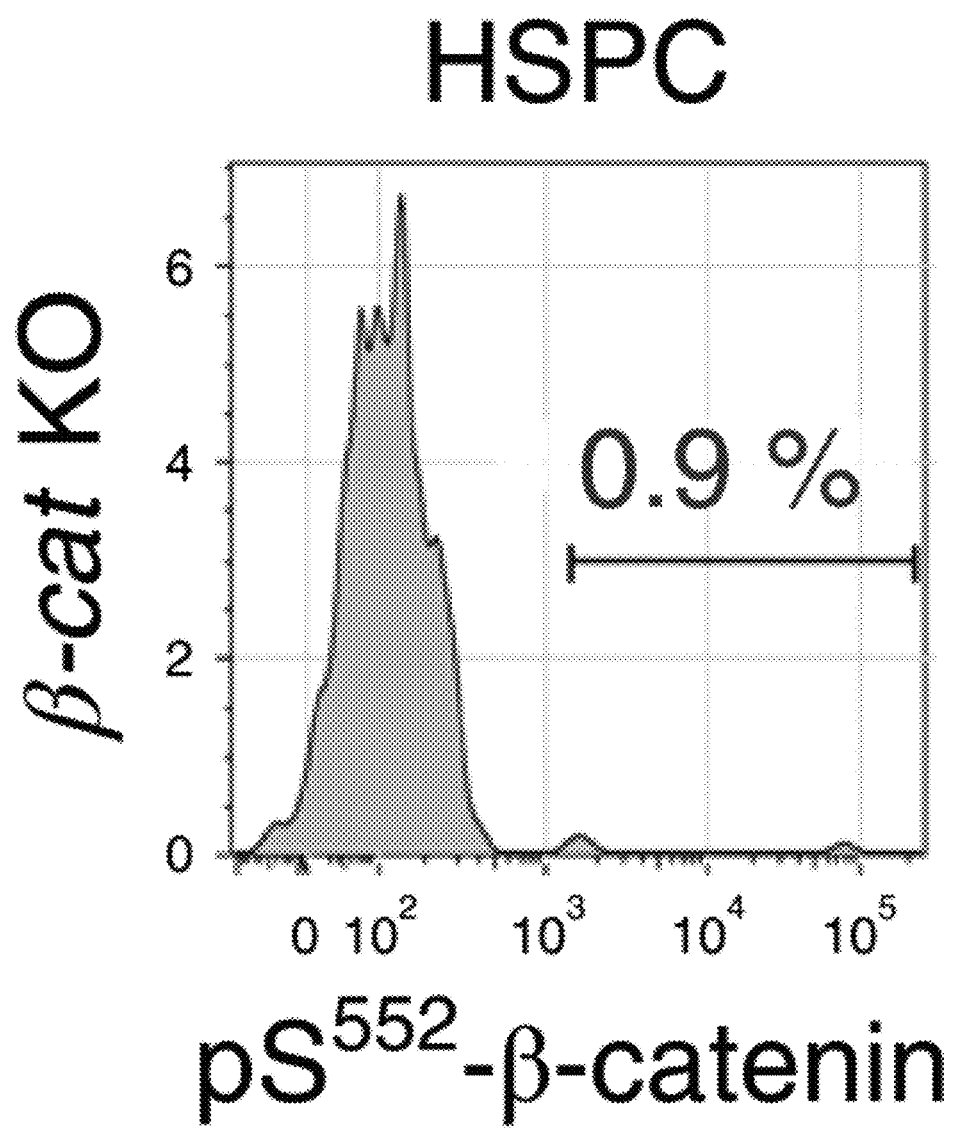
Figure 3H:
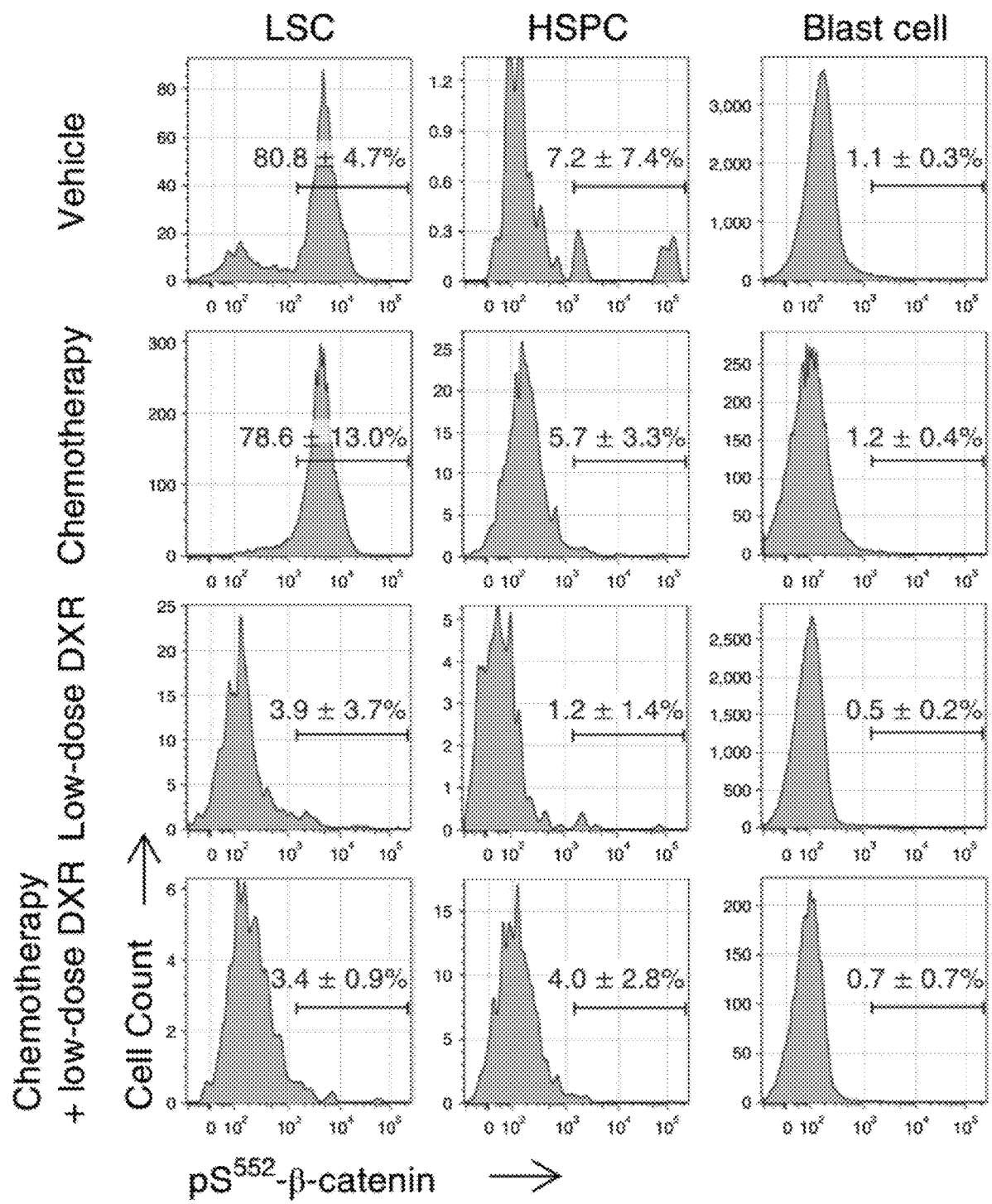

Since pS$^{552}$-β-catenin expression indicates Akt:β-catenin interaction, we next tested which cells expressed this marker and whether targeted/low-dose DXR could inhibit it. HSPCs, LSCs, and non-LSC blast cells were analyzed for pS$^{552}$-β-catenin expression (FIG. 3E). Isotype control and conditional β-catenin knock-out mice show only trace to no staining (FIG. 3F and FIG. 3G). While pS$^{552}$-β-catenin was expressed rarely in HSPCs and nearly absent from blast cells, most LSCs, including chemoresistant ones, were pS$^{552}$-β-catenin$^+$. However, [Low]DXR treatment substantially reduced pS$^{552}$-β-catenin expression (FIG. 3H). These data demonstrate that, unlike HSPCs and blast cells, most LSCs express Akt-activated β-catenin, and DXR inhibits Akt:β-catenin interaction in LSCs.

Figure 3I:
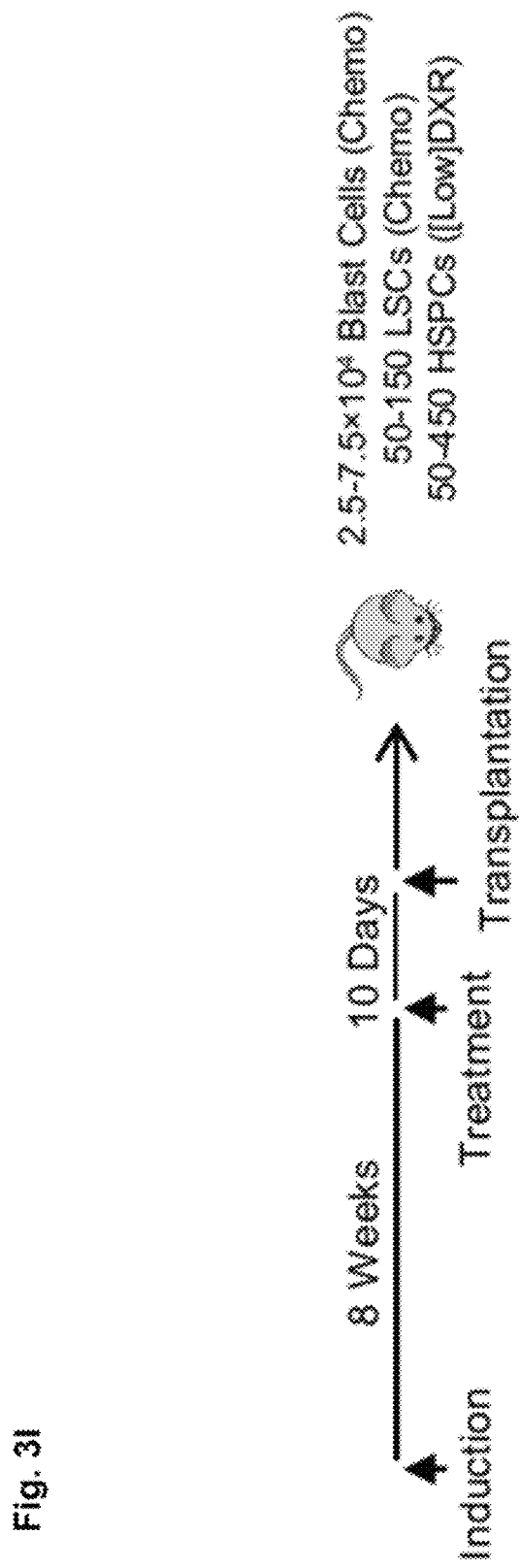
Figure 3K:
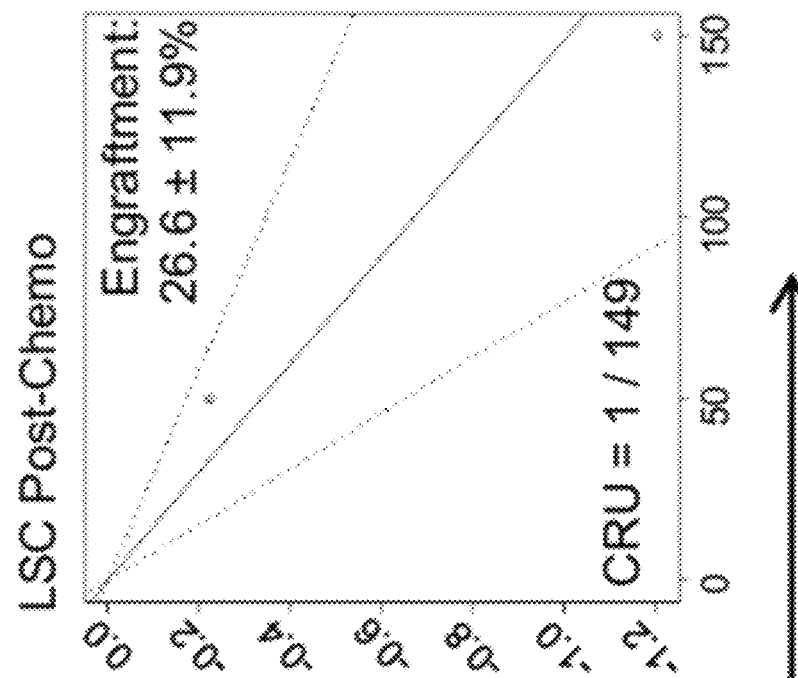
Figure 3J:
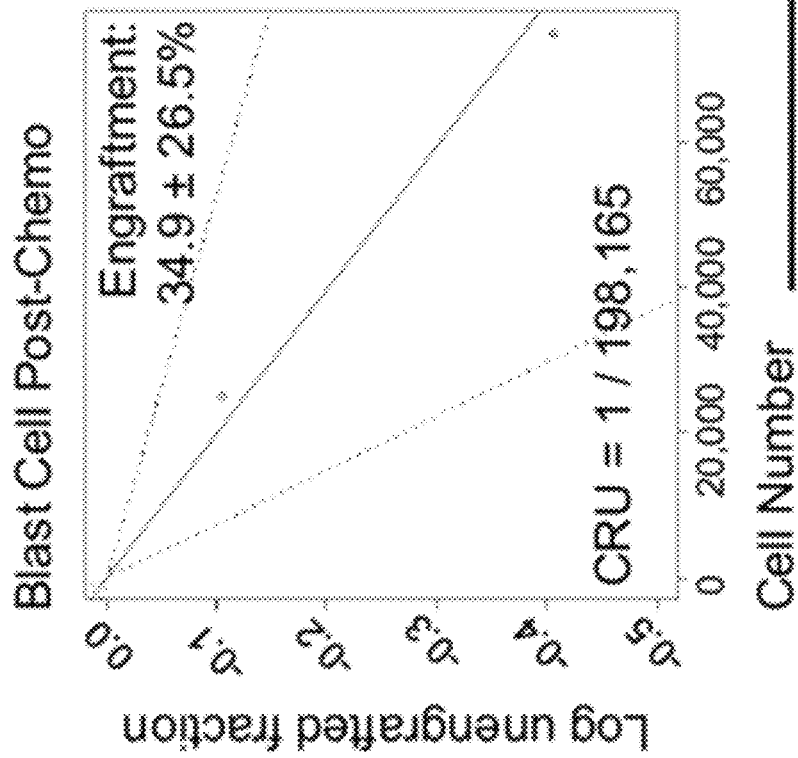

To quantify the tumorigenic activity of LSCs that expand after chemotherapy relative to blast cells, we performed limiting-dilution analysis involving transplantation of each for these populations at different doses. Chemoresistant LSCs or blast cells following chemotherapy were sorted and transplanted into recipient mice at 3 doses. LDA analysis showed a >1,300-fold increase in competitive-repopulating unit (CRU) activity of chemoresistant LSCs compared to blast cells surviving chemotherapy (FIG. 3I; Table 1). These data show that chemoresistant Lin⁻ c-Kit$^{Mid}$ CD3⁺ LSCs are markedly enriched in functional tumorigenic activity, consistent with previous reports that these cell surface markers identify highly enriched leukemia-initiating cells (Guo et al. 2008; Schubbert et al. 2014).

TABLE 1

Competitive Repopulating Unit freqency from chemotherapy treated leukemia mice.

| Treatment of Donors | Transplant Population | Dose | Tested | Engrafted | Estimate | Lower | Upper |
|---|---|---|---|---|---|---|---|
| Chemo. | Blast Cells | 25,000 | 10 | 1 | 1/198,165 | 1/528,906 | 1/74,247 |
|  |  | 75,000 | 9 | 3 |  |  |  |
| Chemo. | LSCs | 50 | 10 | 2 | 1/149 | 1/289 | 1/77 |
|  |  | 150 | 10 | 7 |  |  |  |

Recipients of sorted blast cells, LSCs or HSPCs (see FIGS. 3A-3K) from chemotherapy or [Low]DXR treated mice were analyzed at 10-12 weeks post-transplant. Recipient mice exhibiting 1% CD45$^{Hi}$ blast cells in bone marrow were considered engrafted. Upper and lower confidence intervals for the estimated CRU frequency were obtained using ELDA software (http://bioinf.wehi.edu.au/software/elda/index.html).

Example 4

Figure 4A:
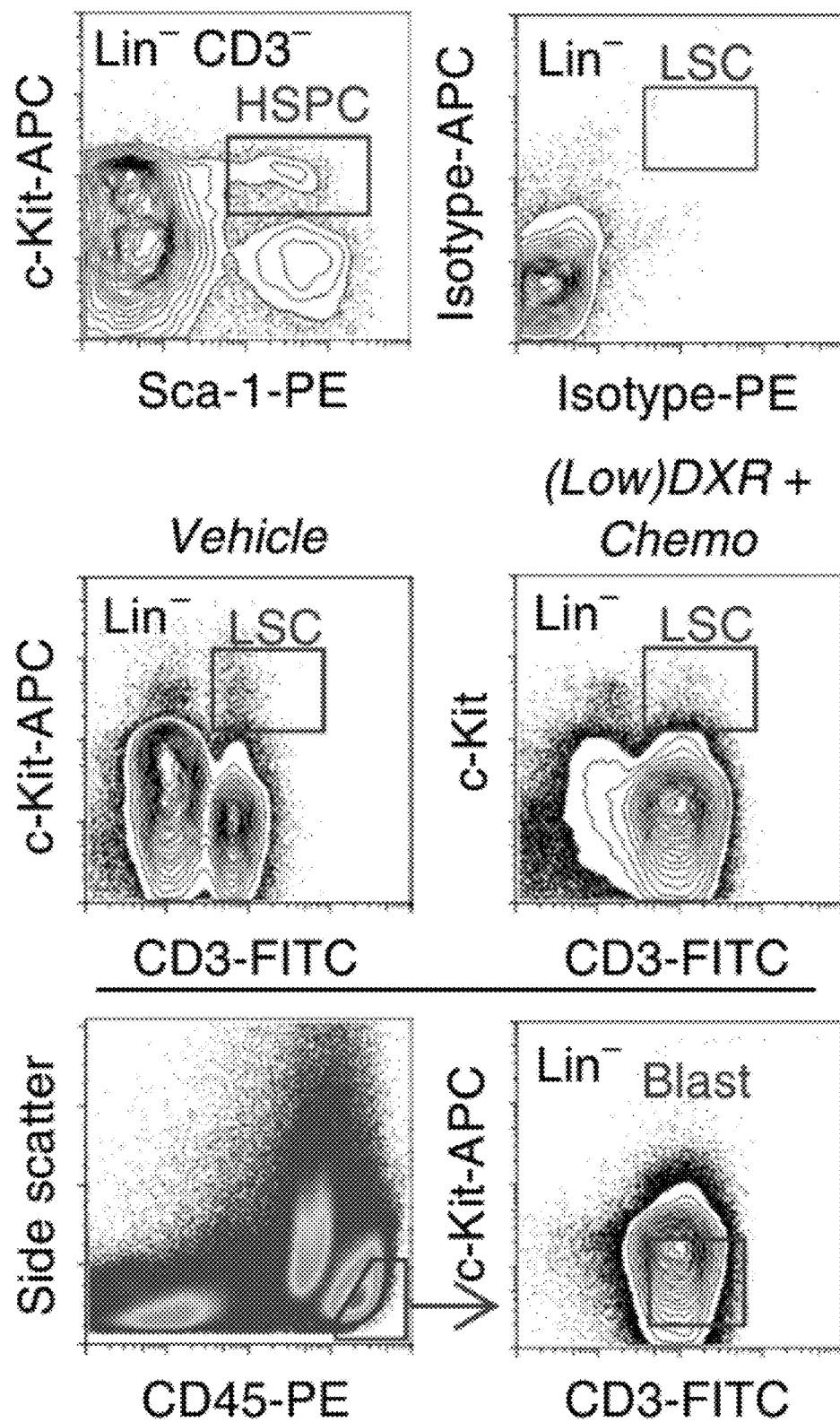
Figure 4B:
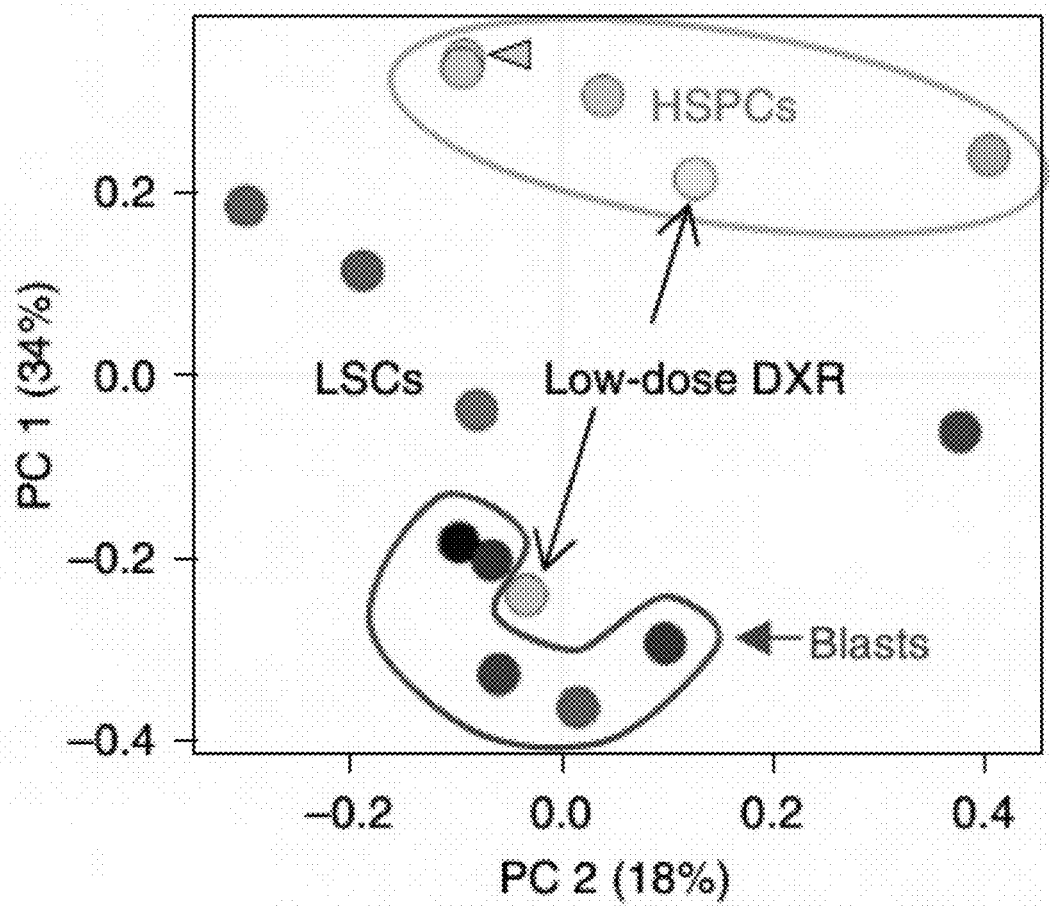
FIG. 4B shows the PCA of each population sorted from mice treated with the indicated drugs. Two biological replicates (using 4-5 male and female mice and performing 2-3 technical replicates) were averaged for each dot. Light green oval indicates all HSPC populations; dark green indicates all blast populations. Remaining populations are LSCs. Arrows indicate LSCs and HSPCs sorted from [Low]DXR only treated mice. (Note that HSPCs from vehicle or chemotherapy treated mice largely overlap, indicated by light gray arrowhead.)
Figure 9A:
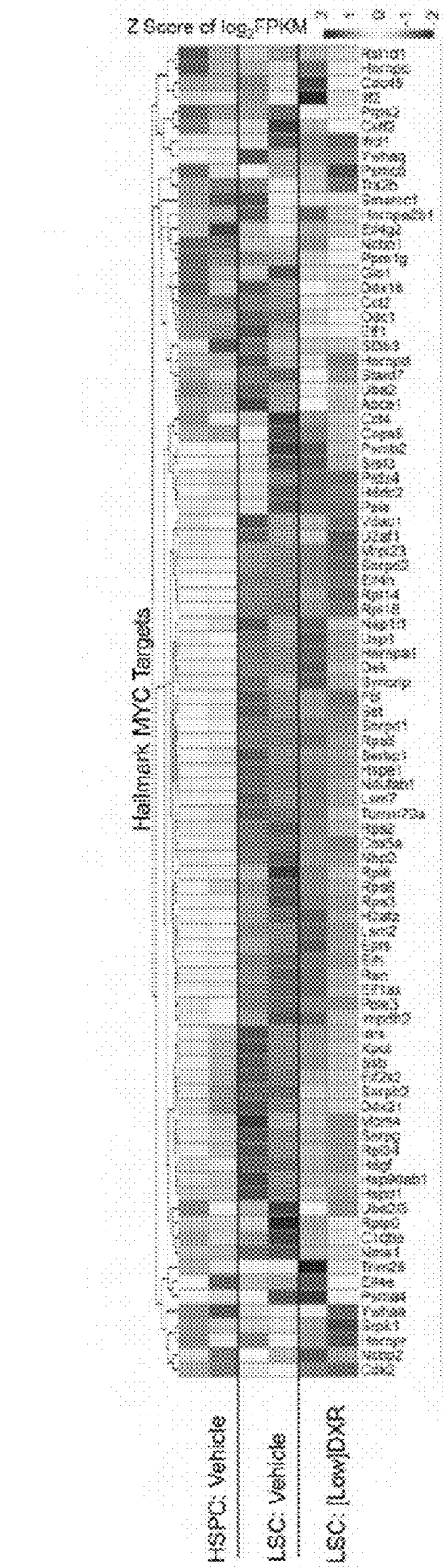
FIGS. 9A-9F show that Low-dose DXR inhibits downstream Wnt signaling.
Figure 9B:
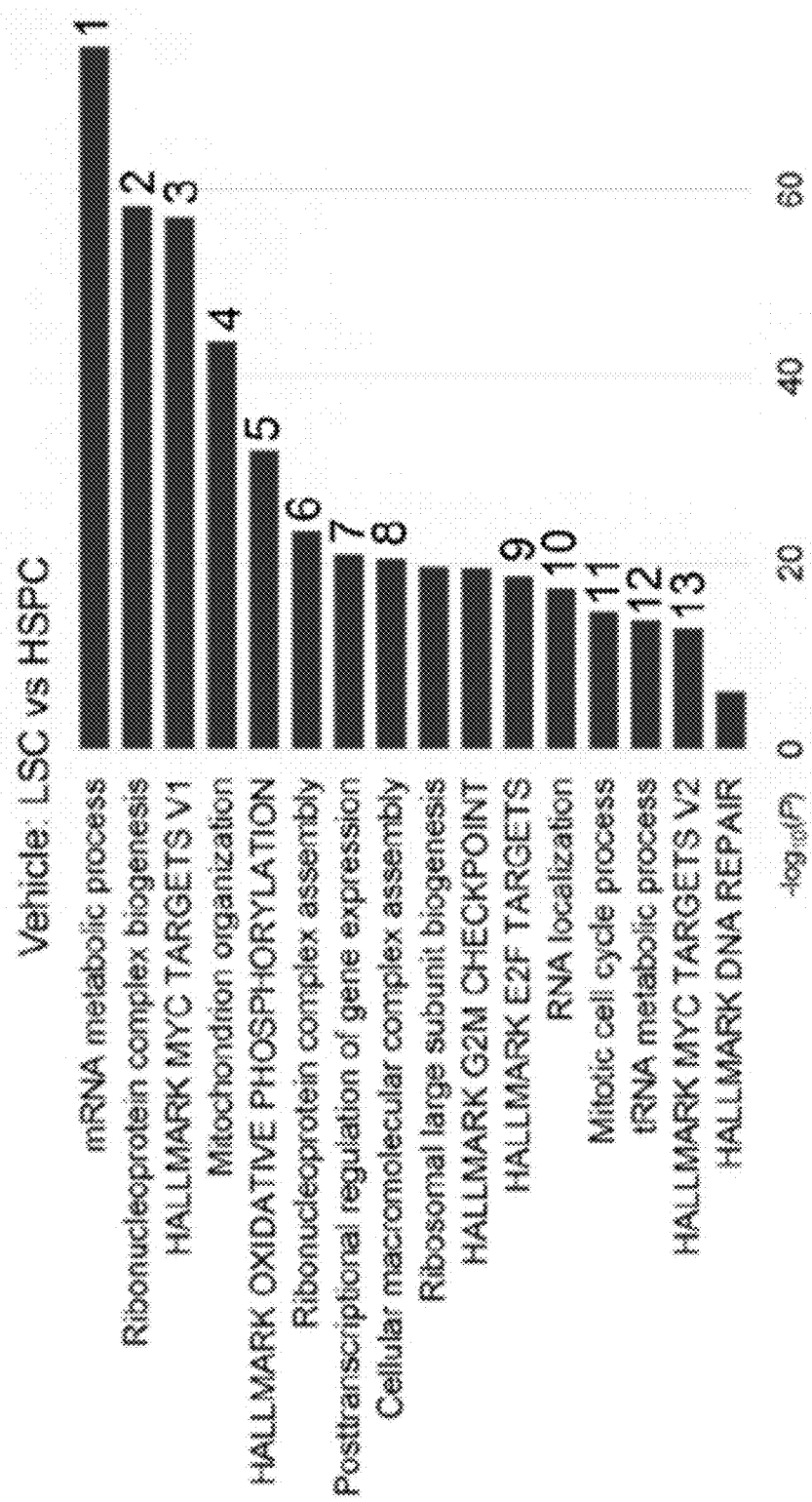
Figure 9C:
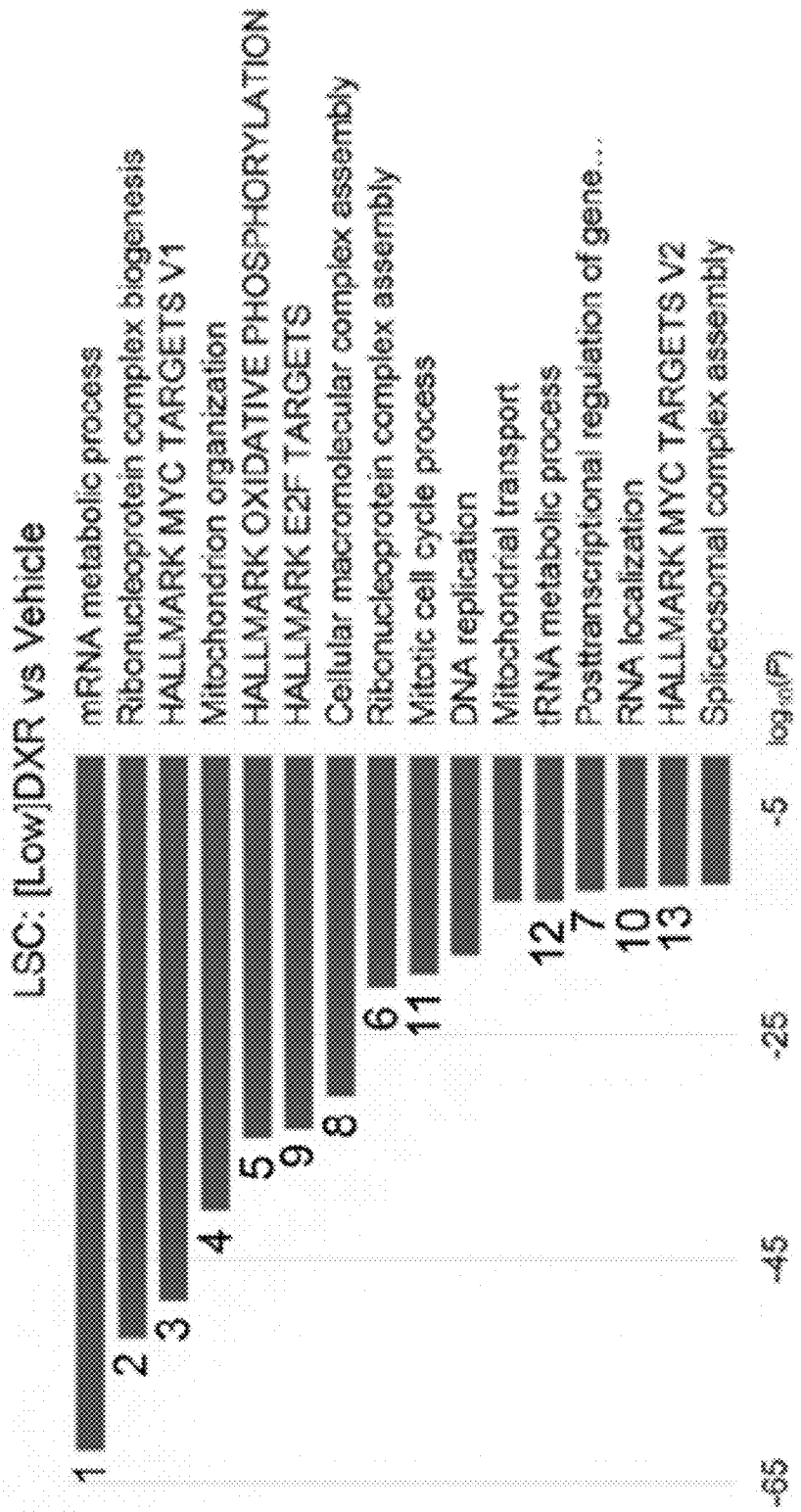
Figure 9D:
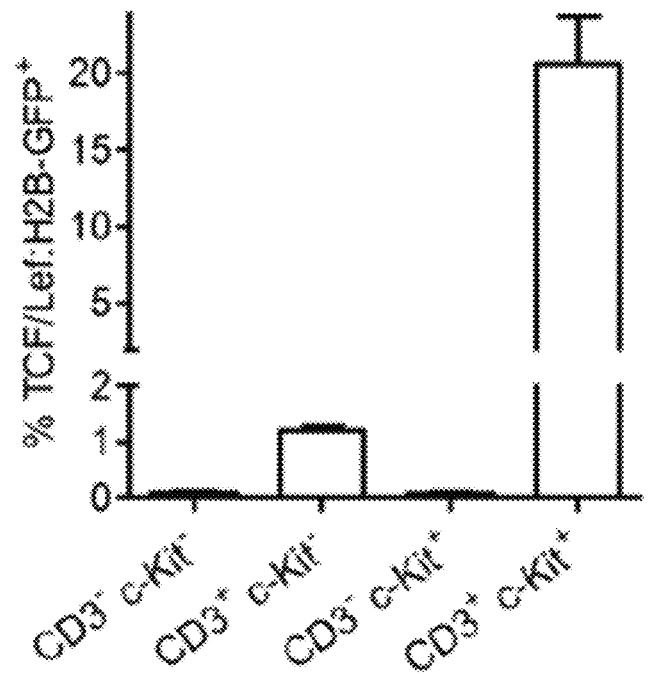
Figure 9E:
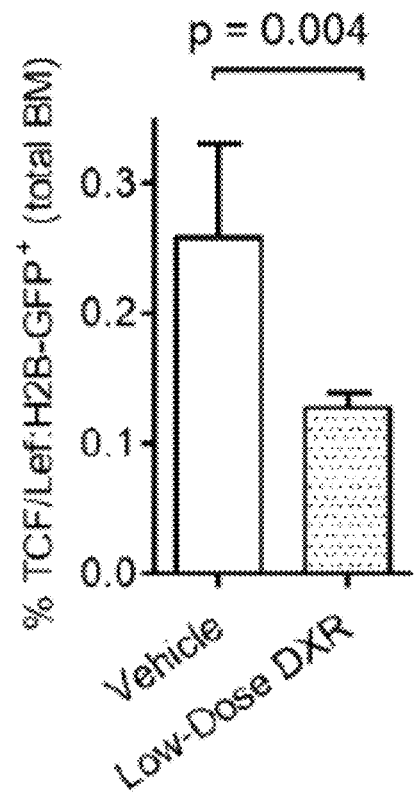
Figure 9F:
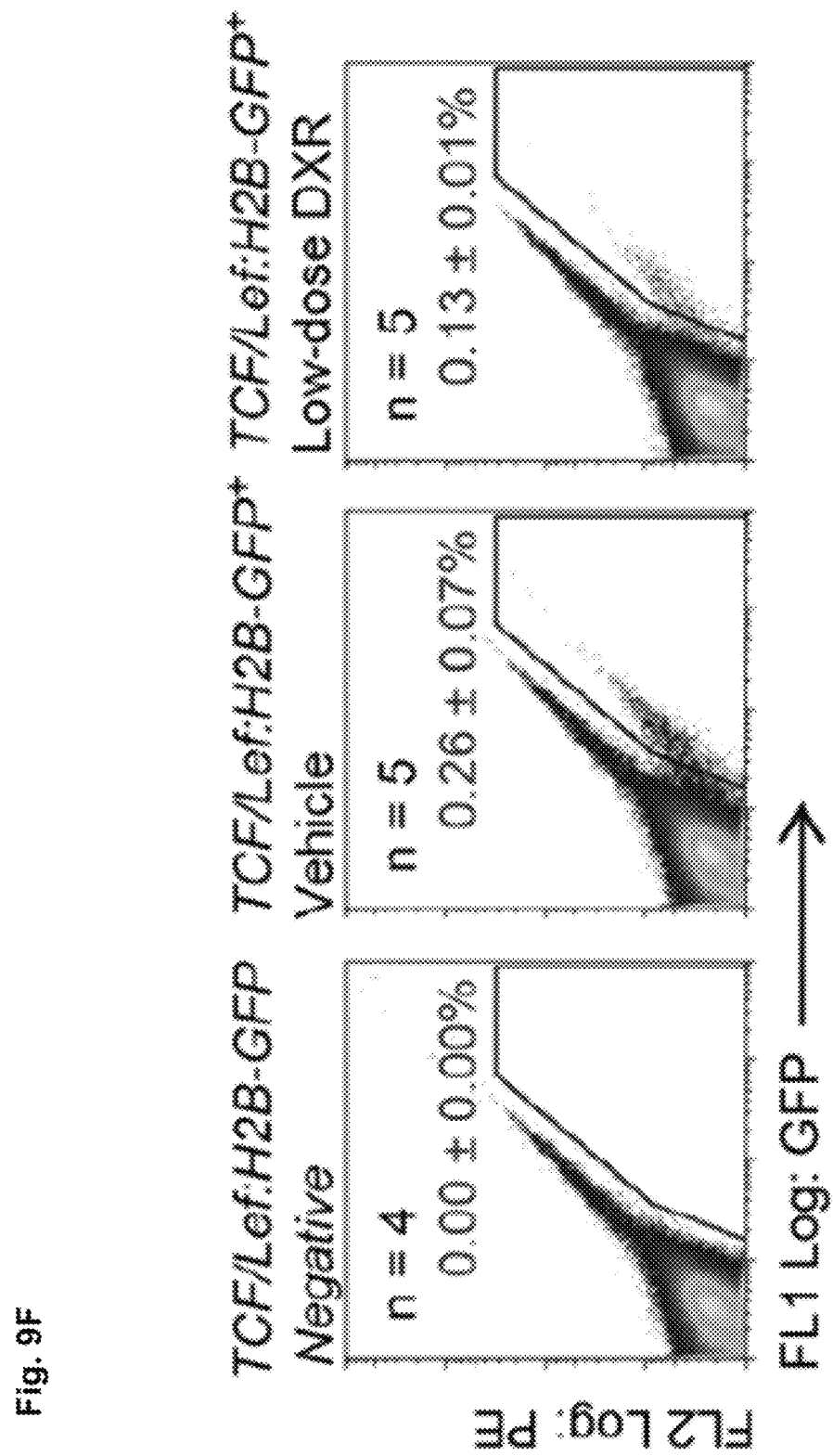

Low-Dose DXR Treatment Reduces Expression of Multiple Immune Checkpoints on LSCs but Clinical-Dose DXR Stimulates Therapy-Resistance To further investigate the underlying mechanism of [Low] DXR treatment's effects, we performed RNA-seq on blast cells, LSCs and HSPCs sorted from treated mice (FIG. 4A). Population-distance analysis revealed that, while LSCs and HSPCs from vehicle control or chemotherapy treated mice cluster relatively close together, LSCs from [Low]DXR treated mice, unlike the clinical dose, cluster amongst a blast cell cluster that is relatively homogenous, regardless of treatment (FIG. 4B). To further investigate the molecular signature behind this relationship, we compared transcriptomes for enriched gene ontology and pathway terms. Terms upregulated in LSCs relative to HSPCs included hallmark MYC target genes. c-Myc is regulated by β-catenin and plays a critical role in tumorigenesis[65]. However, Hallmark MYC targets were reduced in LSCs from mice treated with [Low]DXR (FIG. 9A), further demonstrating DXR's ability to target the Wnt pathway. Overall, enriched terms upregulated in LSCs vs. HSPCs but downregulated in LSCs after treatment with [Low]DXR were strikingly symmetrical (FIG. 9B and FIG. 9C). To further test whether targeted/low-dose DXR inhibits downstream 3-catenin targets, we used TCF/Lef:H2B-GFP reporter mice and found that GFP expression in these mice was essentially restricted to T-cells, particularly their c-Kit⁺ progenitors, and low-dose DXR treatment significantly inhibits Wnt-signaling reporter activity (FIGS. 9D-9F). Together, these data indicate that [Low] DXR treatment targets the downstream canonical Wnt pathway.

Figure 4C:
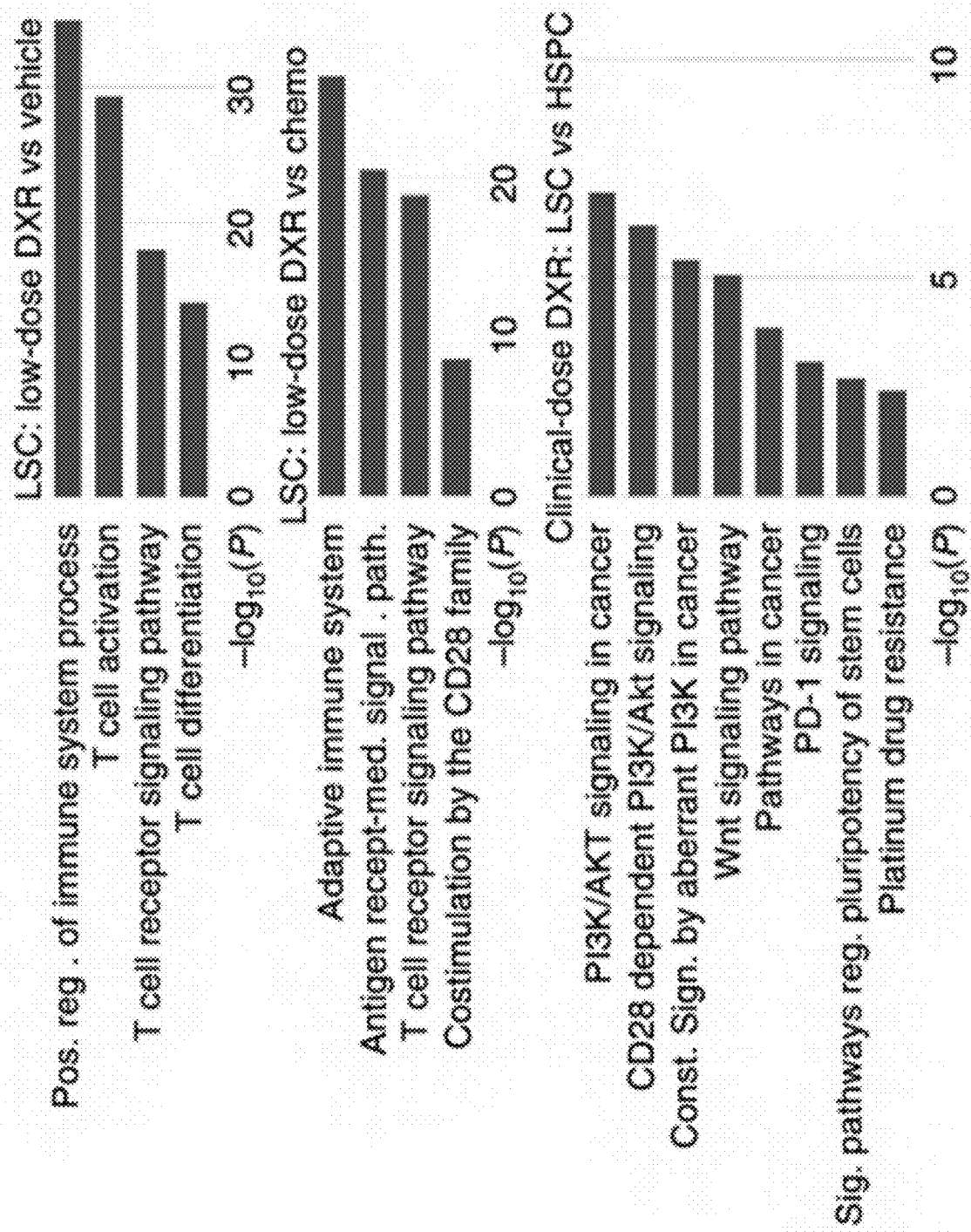
FIG. 4C shows gene ontology enrichment analysis using −log 10 of the uncorrected p value as x axis. Upregulated enriched terms are shown for the indicated population/treatment comparisons.
Figure 4D:
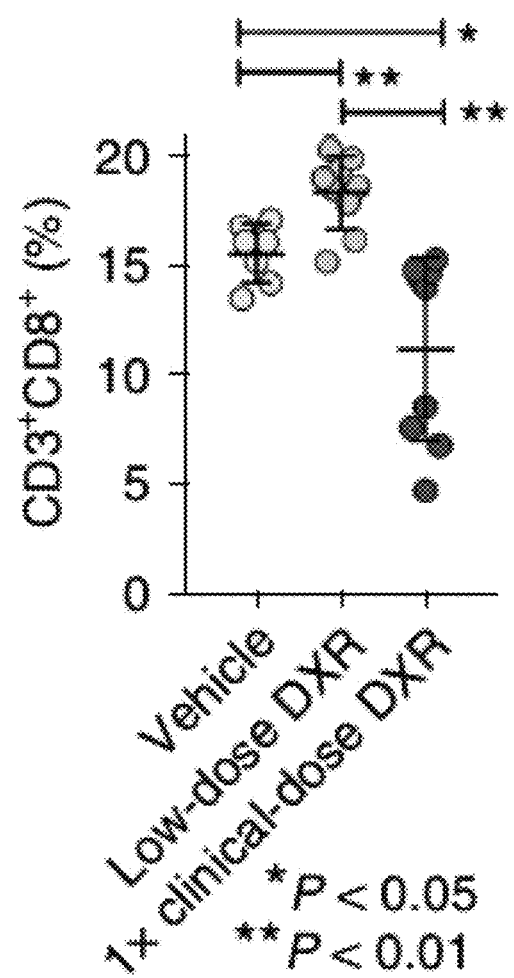
FIG. 4D shows that peripheral blood from leukemic mice was analyzed by FACS for $CD8^+$T-cells at 48 hrs post-treatment with vehicle, [Low]DXR or clinical DXR (1×20 mg/ml).
Figure 4E:
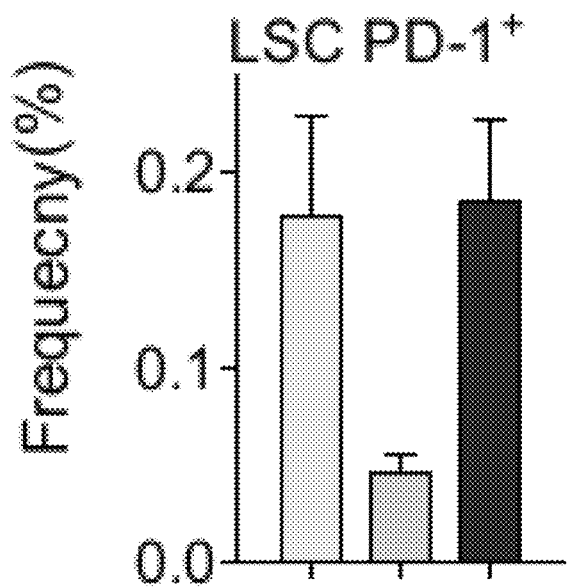
FIGS. 4E-4F show that LSCs were analyzed at 3 days post-treatment for PD-L1. Frequency in BM (top) and frequency of the indicated immune checkpoint within the LSC population (bottom) are shown.
Figure 4F:
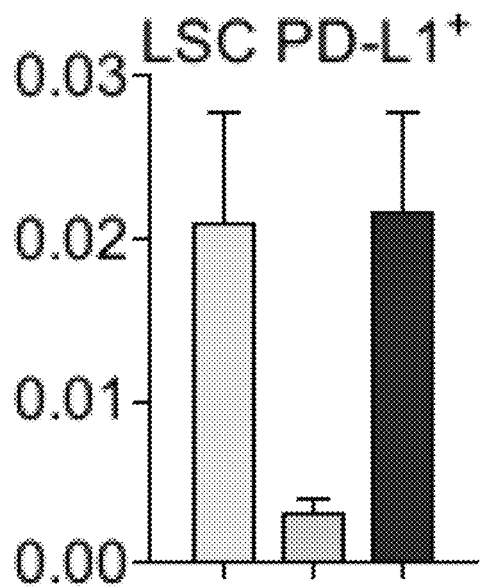
Figure 4G:
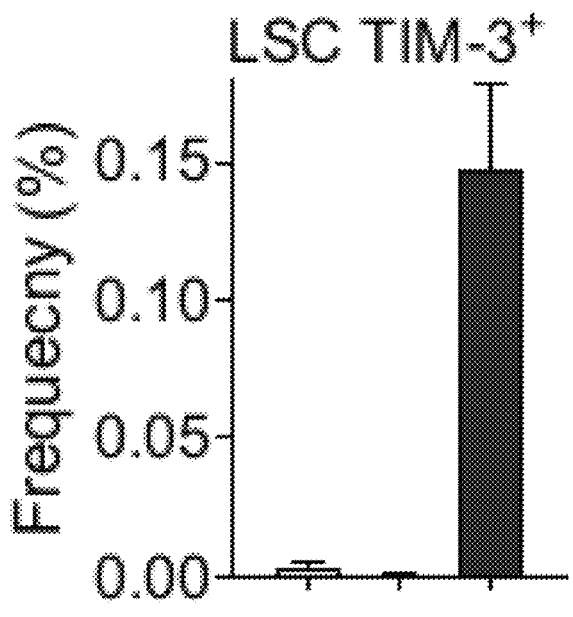
FIG. 4G shows that LSCs were analyzed at 3 days post-treatment for TIM-3. Frequency in BM (top) and frequency of the indicated immune checkpoint within the LSC population (bottom) are shown.
Figure 4H:
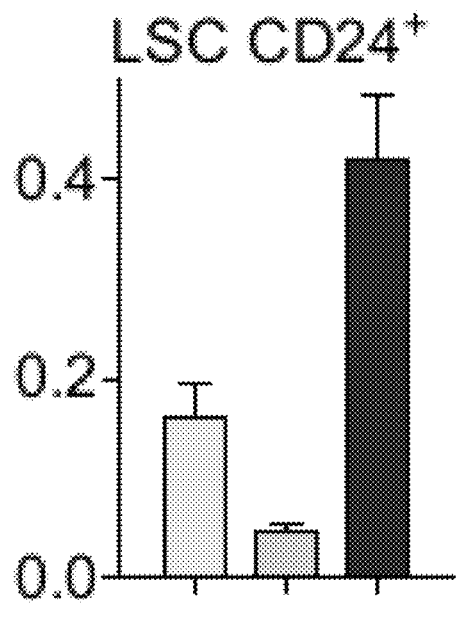
FIG. 4H shows that LSCs were analyzed at 3 days post-treatment for CD24. Frequency in BM (top) and frequency of the indicated immune checkpoint within the LSC population (bottom) are shown.
Figure 4J:
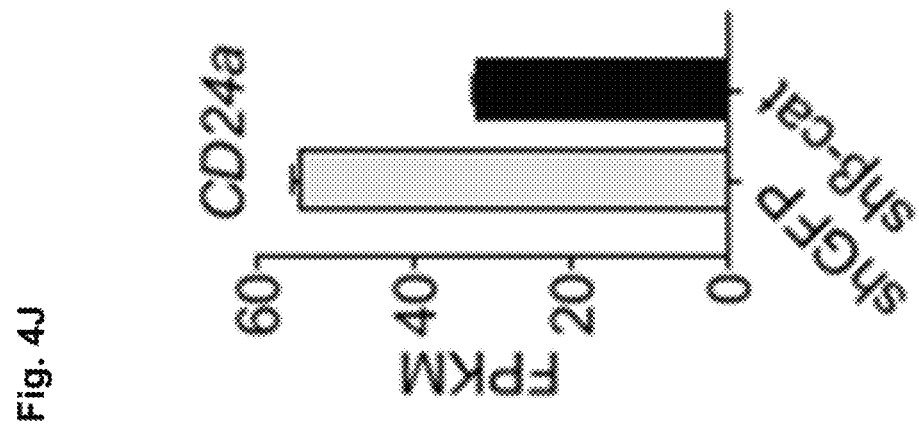
FIG. 4J shows the CD24a expression in mouse ES cells with β-catenin knock-down for 48 hours compared with the control (shGFP).
Figure 4I:
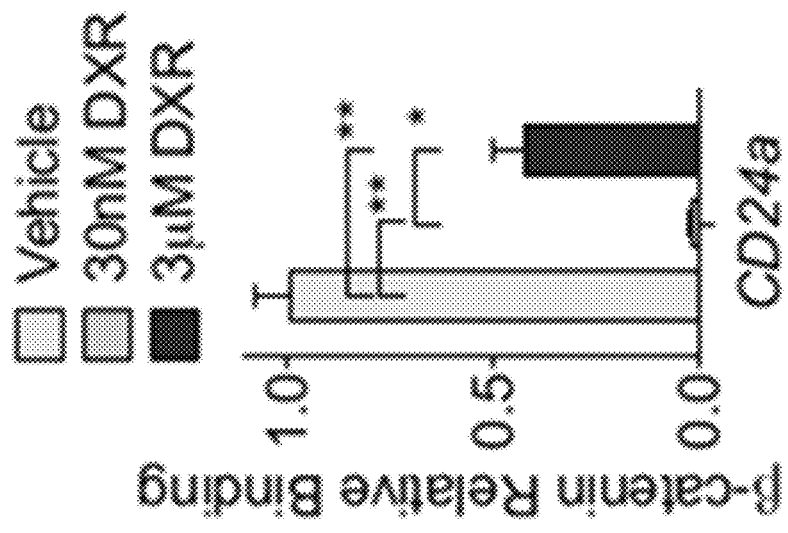
FIG. 4I shows the relative binding of 3-catenin the Cd24a gene locus (fold enrichment by ChIP-qPCR, normalized to the vehicle samples) 4 hours after low (30 nM) and high (3 μM) DXR treatment.
Figure 10A:
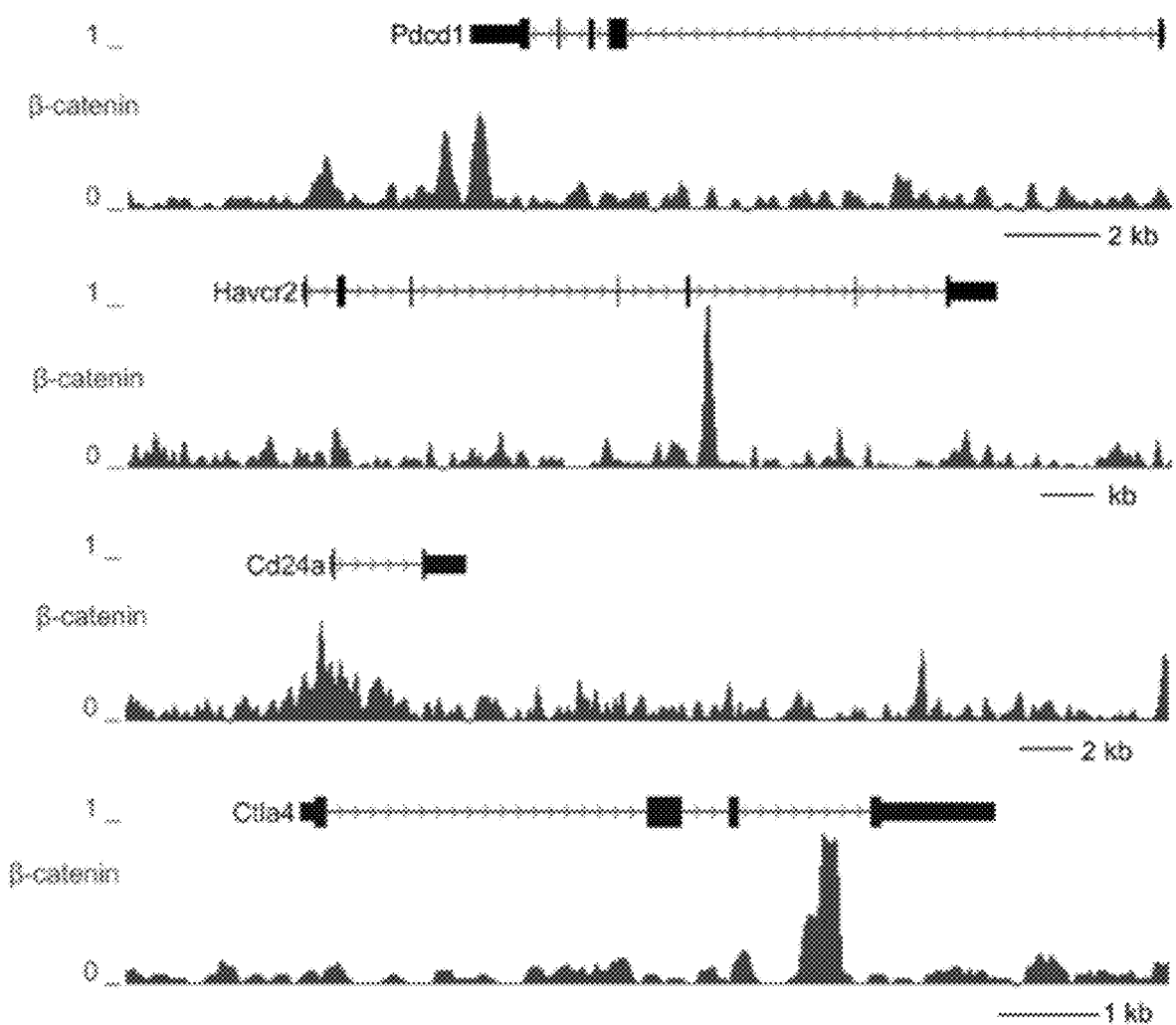
FIGS. 10A-10C show that β-catenin binds multiple immune checkpoint gene loci, and low-dose DXR has differential effects on IC genes in LSCs and blast cells.
Figure 10B:
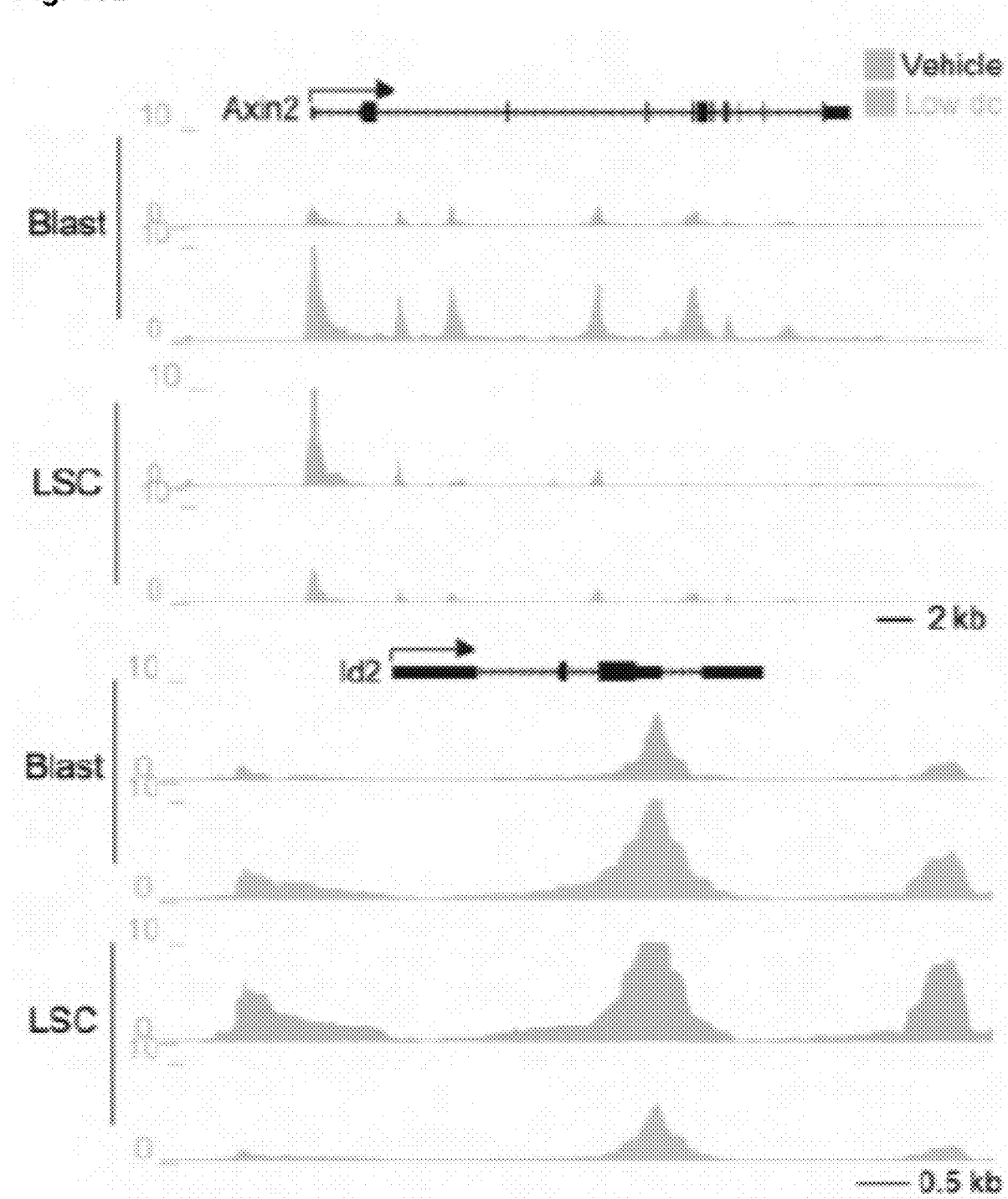
Figure 10C:
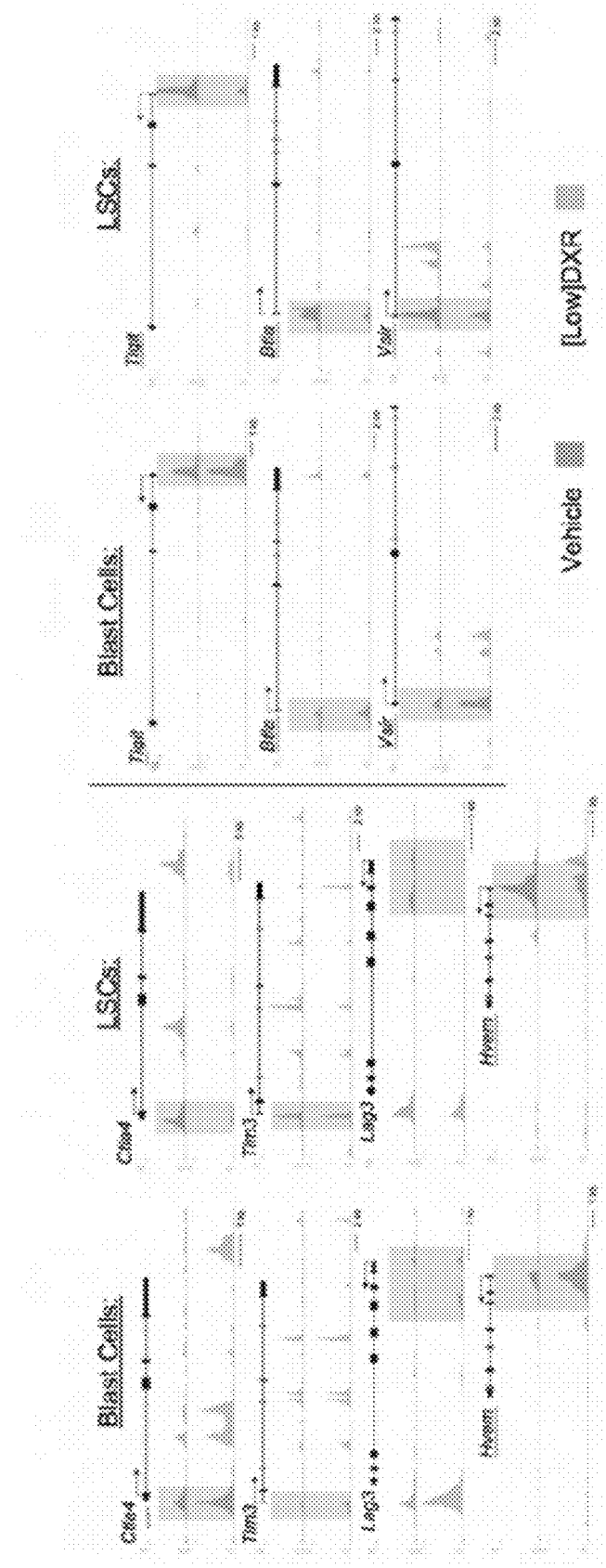

Beyond direct targeting of the Wnt pathway, LSCs from mice treated with [Low]DXR compared to control or chemotherapy revealed the most highly enriched involved upregulation of immune-related terms, particularly those involving T-cells (FIG. 4C). Since the therapeutic efficacy of doxorubicin depends on a significant contribution from the immune system, particularly CD8⁺ T cells (Galluzzi et al. 2015; Casares et al. 2005), we also measured the frequency of these cells after treatment with low or clinical dose DXR. [Low]DXR treatment showed a significant increase in CD8⁺ T cells; however clinical-dose DXR resulted in a significant reduction in these cells (FIG. 4D). While CD8⁺ T cells can eliminate cancer cells, some tumor populations resist CD8⁺ T cells by expressing immune checkpoints. Indeed, most LSCs were found to express immune checkpoints such as PD-L1 and CD24. PD-L1 levels associate with stemness indices in cancer and PD-L1 accumulation on cancer stem cells promotes immune evasion (Hsu et al. 2018; Malta et al. 2018). Similarly, CD24 serves as an immune checkpoint suppressing damage-induced immune responses and marks cancer stem cells exhibiting signatures of immune evasion (Jinesh et al. 2017; Chen et al. 2009). Interestingly, these populations were reduced with [Low]DXR treatment, but with clinical-dose DXR, this reduction was reversed (FIGS. 4E-4G). Rare TIM-3⁺ LSCs were also reduced with [Low] DXR but increased substantially with clinical-dose DXR. These data indicate that resistance of LSCs to clinical-DXR may involve not only immunosuppression of CD8⁺ T cells but also expression of immune checkpoints by resistant LSCs. However, with [Low]DXR, not only were CD8⁺ T cells more abundant, LSCs may be more susceptible to their immunosurveillance by reduced immune checkpoint expression. Indeed, using Flag-β-catenin in embryonic stem cells, ChIP-seq revealed that β-catenin binds multiple immune checkpoint gene loci at the promoter region and/or intergenic regions (FIGS. 10A-10C). In particular, CD24 is the most abundantly expressed immune checkpoint we examined in LSCs, and β-catenin binding of the Cd24 promoter region is essentially abolished with low-dose DXR treatment. However, this is partially reversed at high-doses (FIG. 4H). Genetic knock-down of β-catenin also reduced Cd24 expression, supporting a role for β-catenin upregulation of Cd24. (FIG. 4I). At high doses of DXR, the partial reversal of β-catenin binding and enrichment of CD24+LSCs suggest that resistance mechanisms are induced that lead to retention of CD24 expression in DXR-resistant LSCs. Indeed, comparing LSCs and HSPCs from mice treated with clinical DXR revealed increased expression of oncogenic signaling and other resistance pathways, which were not enriched with [Low]DXR treatment (FIG. 4C). PI3K/Akt Signaling in Cancer, Wnt Pathway Signaling, and PD-1 Signaling terms were among those uniquely enriched with clinical DXR treatment relative to others, further indicating how essential these pathways are to therapy resistance in LSCs, particularly since LSCs are relatively resistant to clinical DXR treatment compared to HSPCs (FIG. 3B). These data reveal mechanisms for the differential response of LSCs to [Low]DXR vs clinical DXR treatment, in particular the potential restoration of tumor-fighting T cells and inhibition of the immune checkpoints that resist them with [Low]DXR treatment but immunosuppression and maintenance or induction of those checkpoints at clinical doses.

Figure 4K:
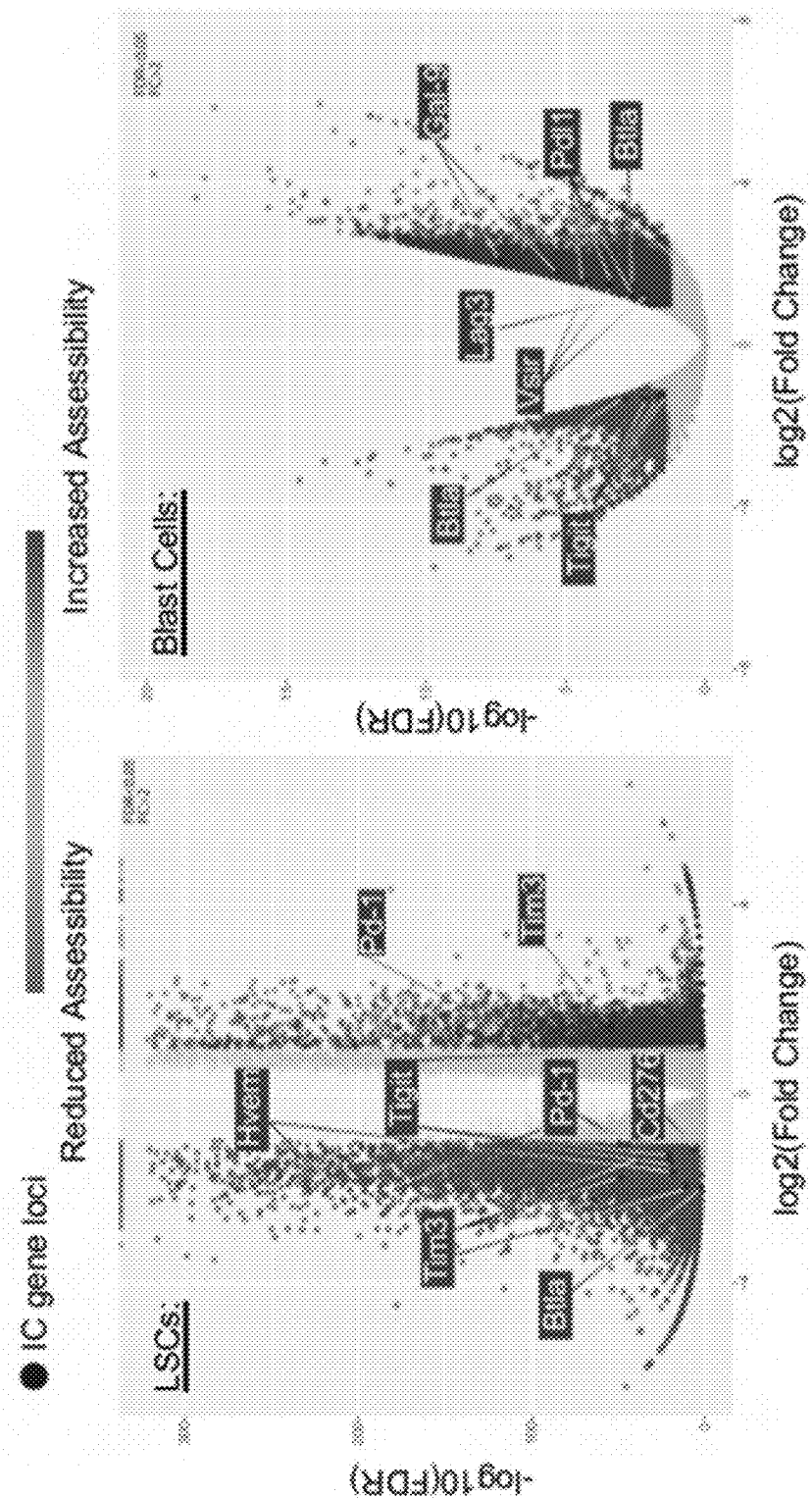
FIG. 4K shows that ATAC-seq was used to show genome wide changes chromatin accessibility in LSCs and blast cells. Inhibitory IC gene loci are highlighted (blue dots).
Figure 4L:
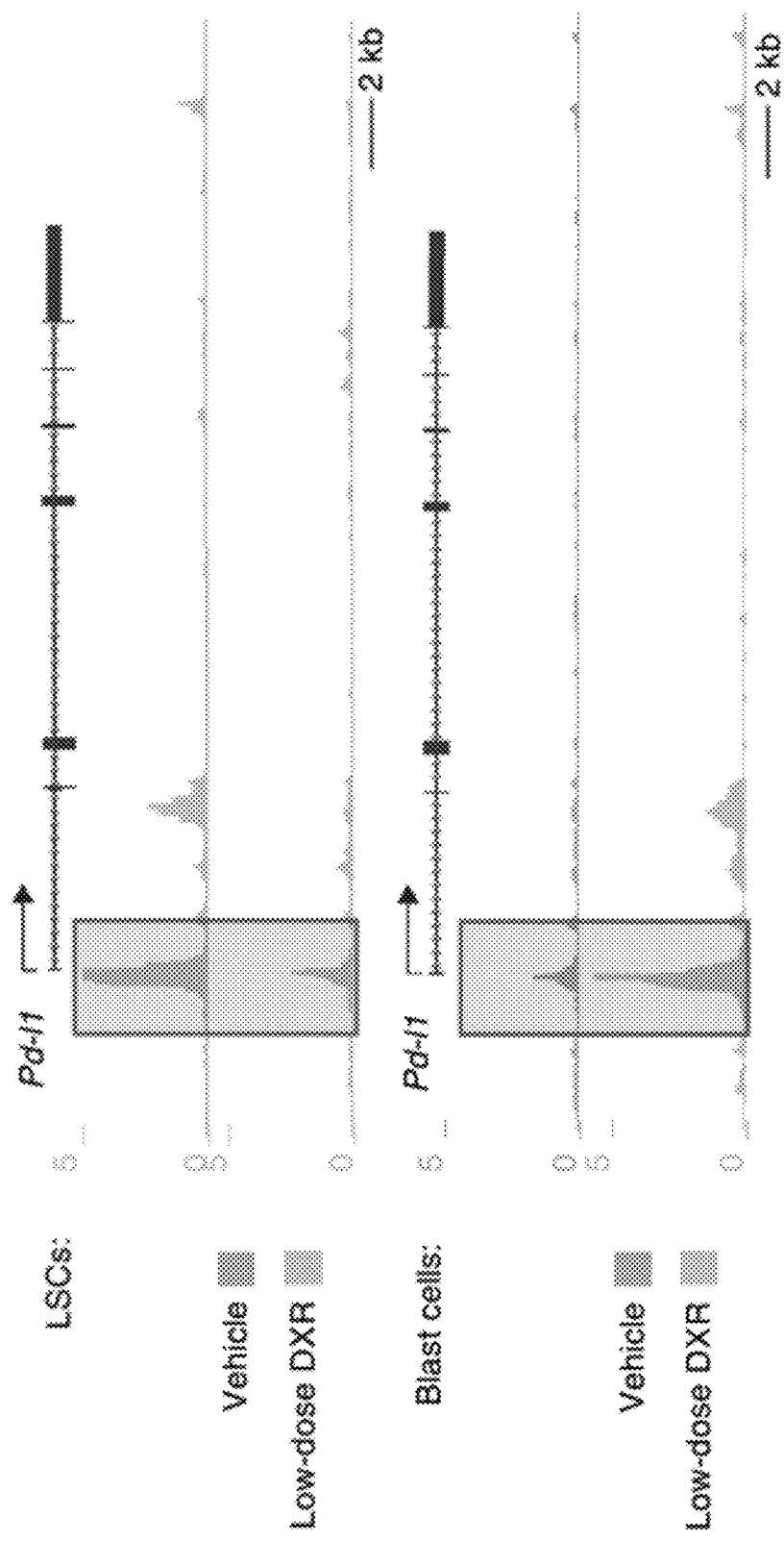
FIG. 4L shows the chromatin accessibility profiles of example IC genes observed by ATAC-seq in LSCs and blast cells. Cells were sorted from BM pooled from 20 leukemia mice treated with [Low]DXR and 8 leukemia mice treated with vehicle control at 15-30 k/replicate.
Figure 4M:
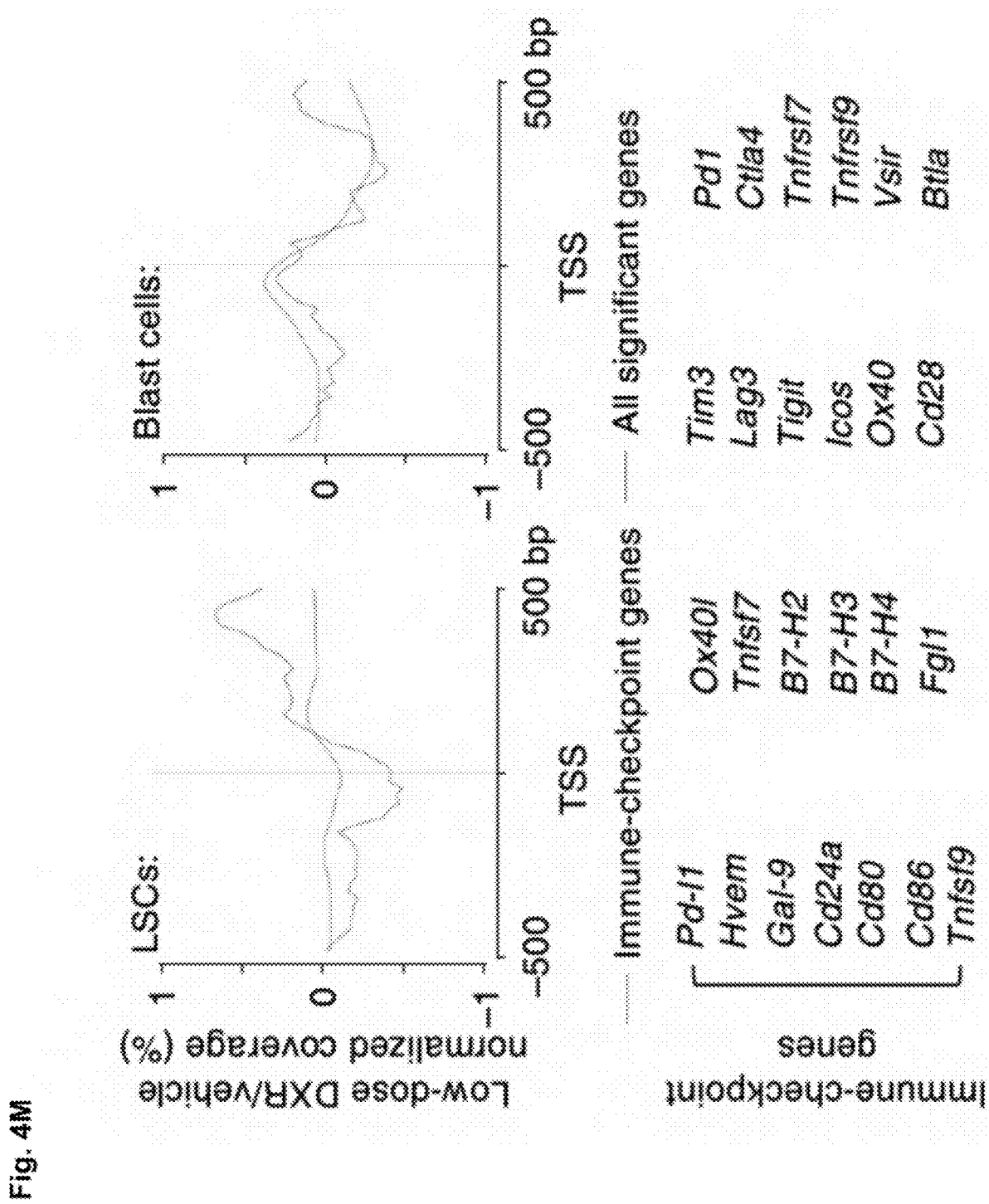
FIG. 4M is metagene analysis of LSCs showing chromatin accessibility near the transcriptional start site (TSS) in immune-checkpoint gene loci (listed) compared with all loci showing significant changes. Gene synonyms are listed here in parentheses Hvem (Tnfrsf14), Gal-9 (Lgals9), Ox40l (Tnfsf4), Tnfsf7 (Cd70), B7-H2 (Icosl), B7-H3 (Cd276), B7-H4 (Vtcn1), Pd1 (Pdcd1), Tnfrsf7 (Cd27), Tim3 (Havcr2), Ox40 (Tnfrsf4).
Figure 4N:
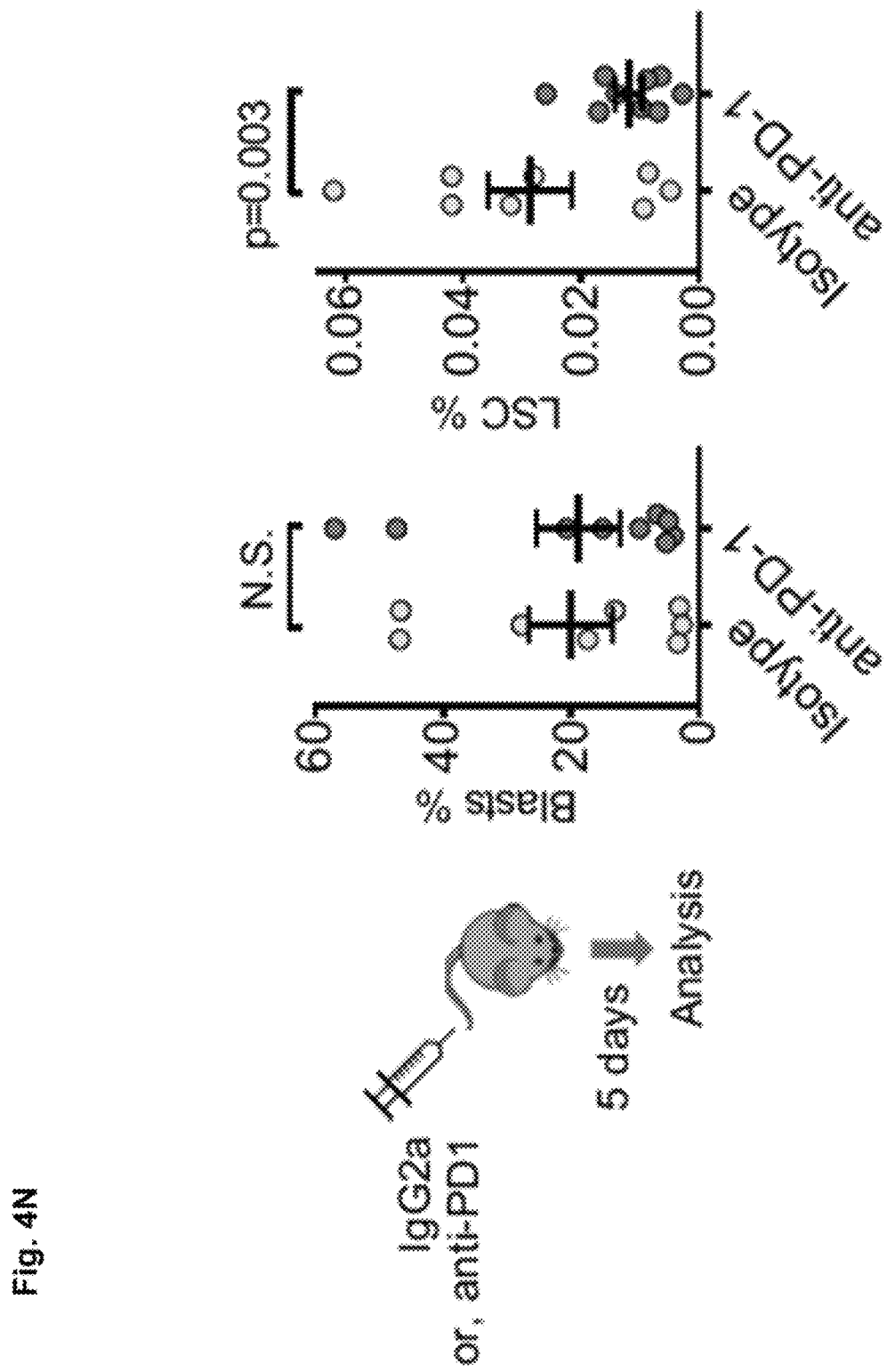
FIG. 4N shows that leukemia mice were treated with anti-PD1 antibody or isotype control and analyzed by FACS. n=8 (isotype) and 9 (anti-PD1) biologically independent mice; data are mean±s.e.m.
Figure 40:
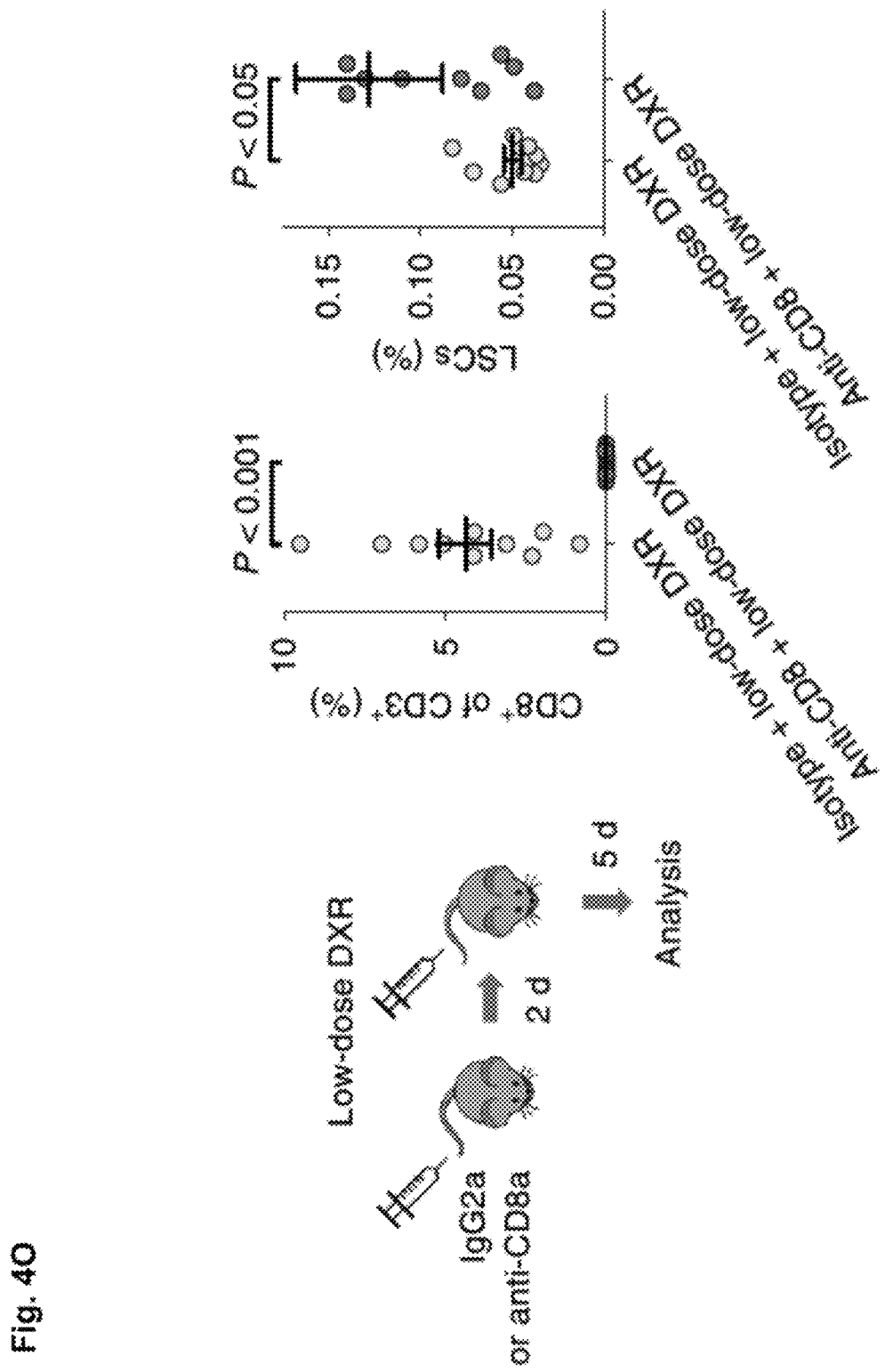

Although LSCs particularly after [Low]DXR treatment are too rare for ChIP-seq, we sorted LSCs and blast cells and used ATAC-seq to measure chromatin accessibility of IC genes. Accessibility in the promoter regions of Wnt target genes was reduced by [Low]DXR treatment in LSCs but not blast cells. In LSCs, IC gene accessibility near the transcriptional start site (TSS) was also reduced by [Low]DXR treatment compared to all significantly changed genes, but this was not observed in blast cells (FIG. 10B). Overall genome wide changes in accessibility to gene loci showed that IC loci in LSCs were predominantly less accessible in response to [Low]DXR treatment (13 loci reduced, 3 increased) whereas the opposite occurred in blast cells (4 reduced, 10 increased) (FIG. 4K and FIG. 4M). Indeed, in LSCs, multiple IC genes showed reduction in promoter accessibility by [Low]DXR treatment but either no reduction or increases in blast cells (FIG. 4L, FIG. 4M and FIG. 10C). Functionally, anti-PD-1 treatment of leukemia mice reduced LSCs but had no effect on blast cells (FIG. 4N). To test whether [Low]DXR's effectiveness depends on CD8+ T cells, we depleted this population immediately prior to [Low]DXR treatment. After CD8+ T cell depletion, [Low]DXR no longer significantly reduced LSCs (FIG. 4O). These data indicate that LSCs, unlike their blast progeny, exhibit unique properties of immune resistance that can be overcome by [Low]DXR treatment.

Example 5

Figure 5A:
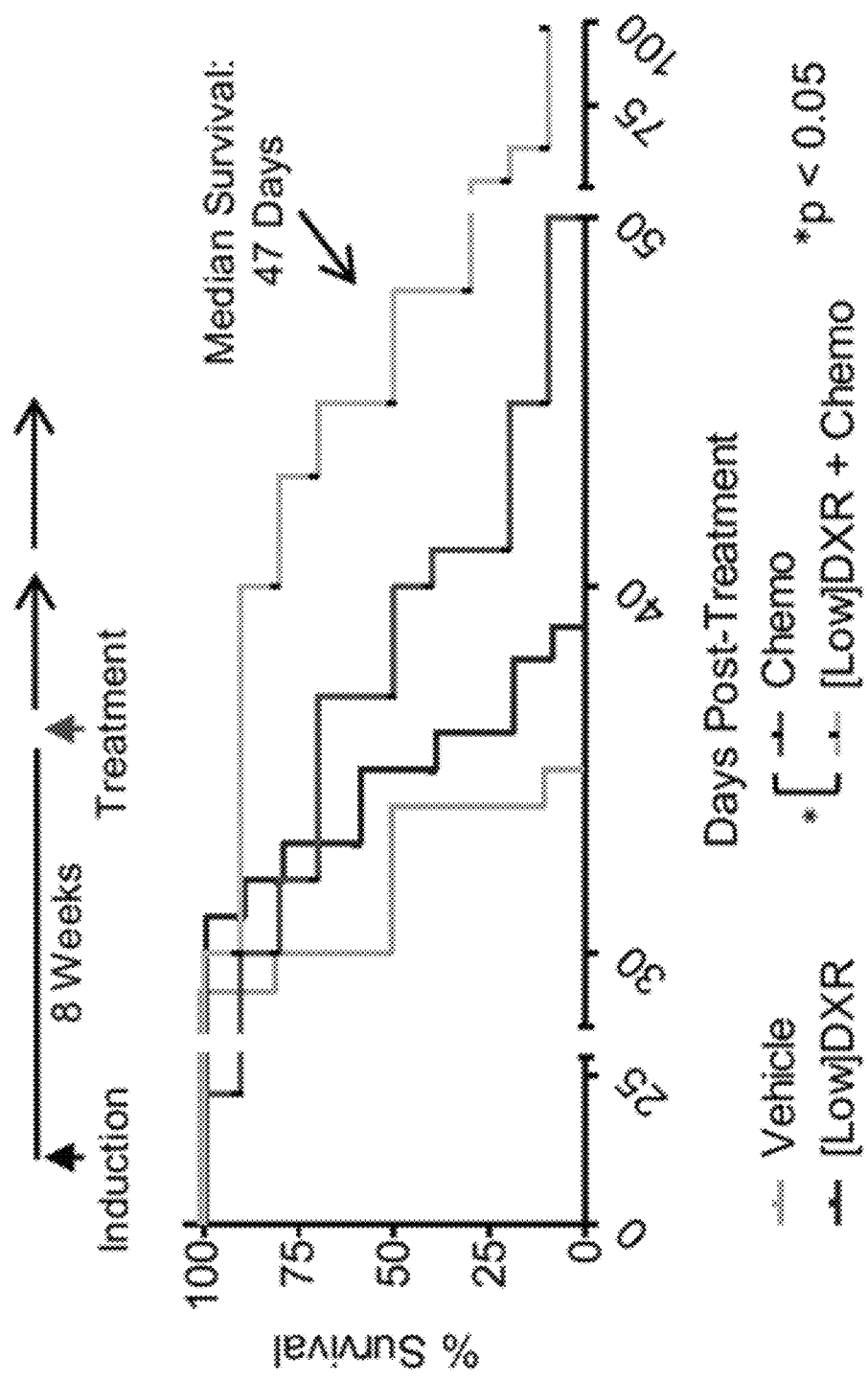

Targeting Chemoresistant LSCs with Low-Dose DXR Reduces Tumorigenicity and Increases Survival We next observed long-term survival of leukemic mice treated with [Low]DXR, chemotherapy, or combination treatment. Mice treated with chemotherapy alone showed somewhat improved overall survival (FIG. 5A), but [Low]DXR only treated mice showed no insignificant improvement, likely due to the insignificant effect of [Low]DXR treatment on blast cells (FIG. 3B and FIG. 5A). However, combining chemotherapy and [Low]DXR significantly increased survival compared to chemotherapy ($p<0.05$) or [Low]DXR ($p<0.01$) alone (FIG. 5A).

Figure 5B:
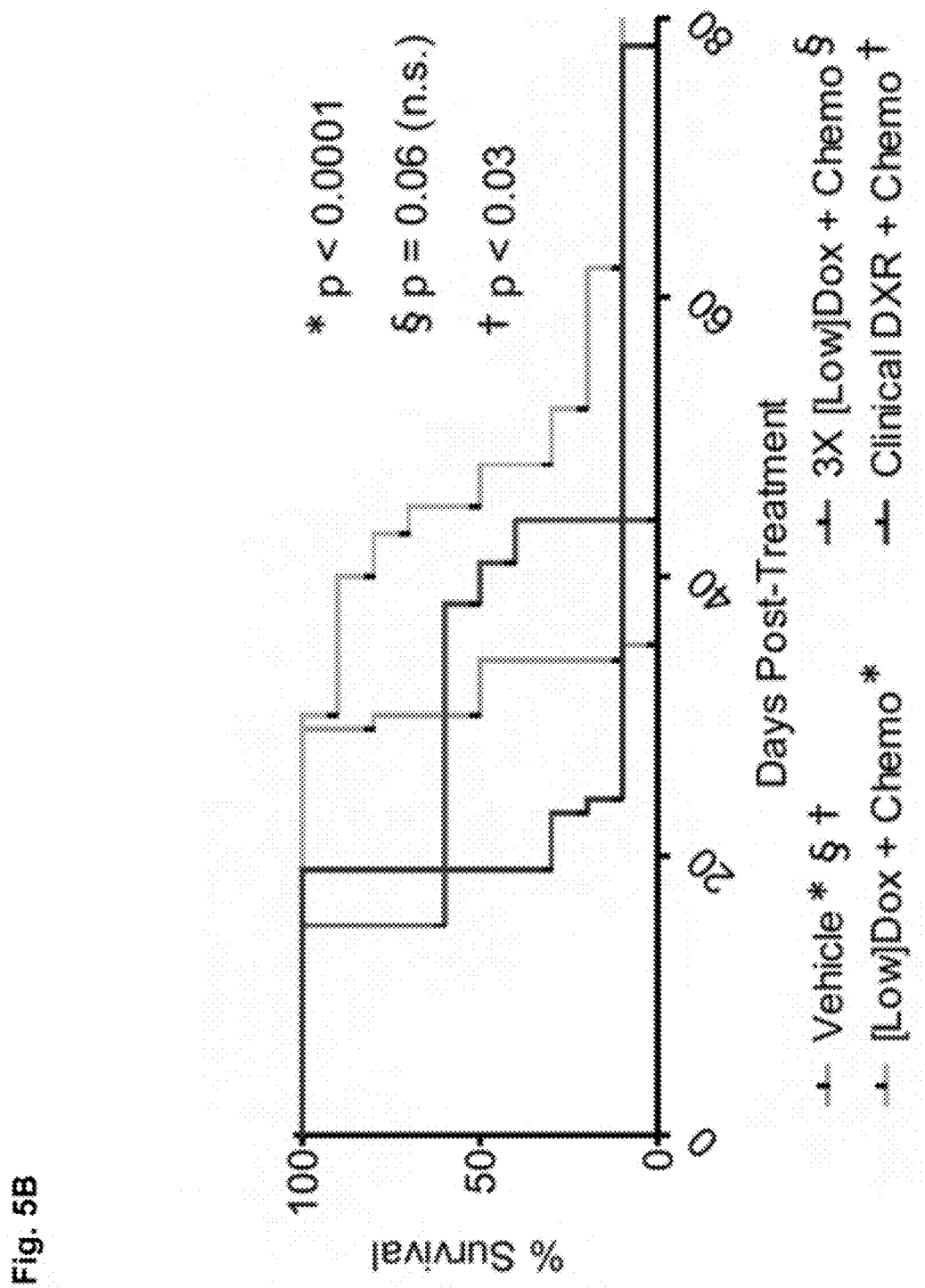

We also investigated whether higher doses of DXR also improved survival when combined with chemotherapy. While [Low]DXR+chemotherapy significantly improved survival, a 3-fold higher dose of DXR did not, while clinical-dose DXR significantly reduced survival compared to vehicle alone (FIG. 5B). These results show that using higher doses of DXR negates or even reverses the beneficial effect of [Low]DXR+chemotherapy treatment.

Figure 5C:
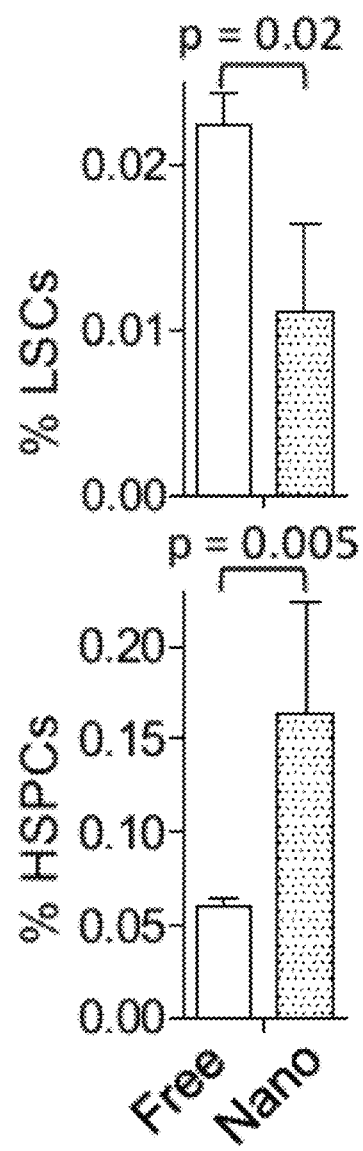
Figure 11B:
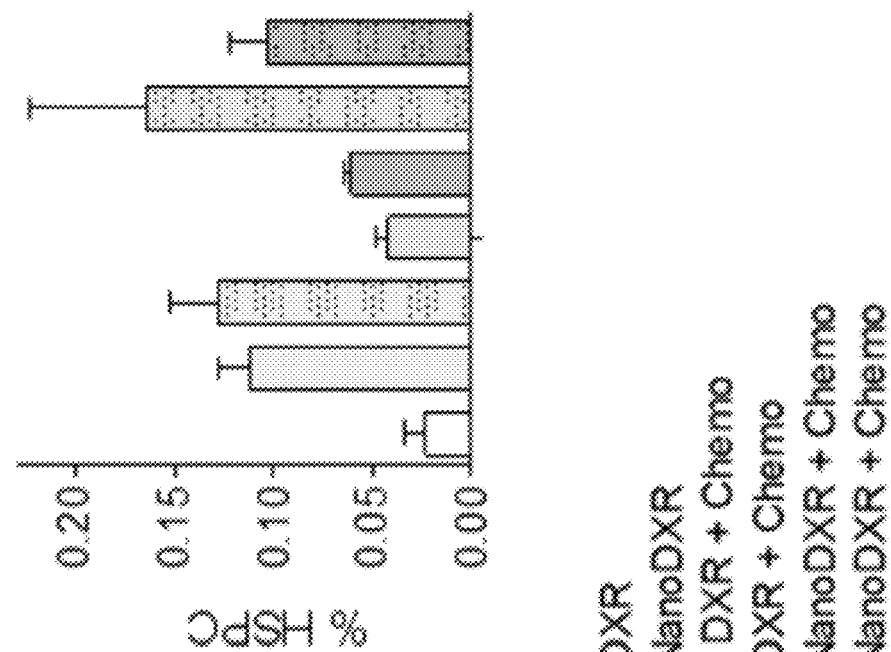
Figure 11A:
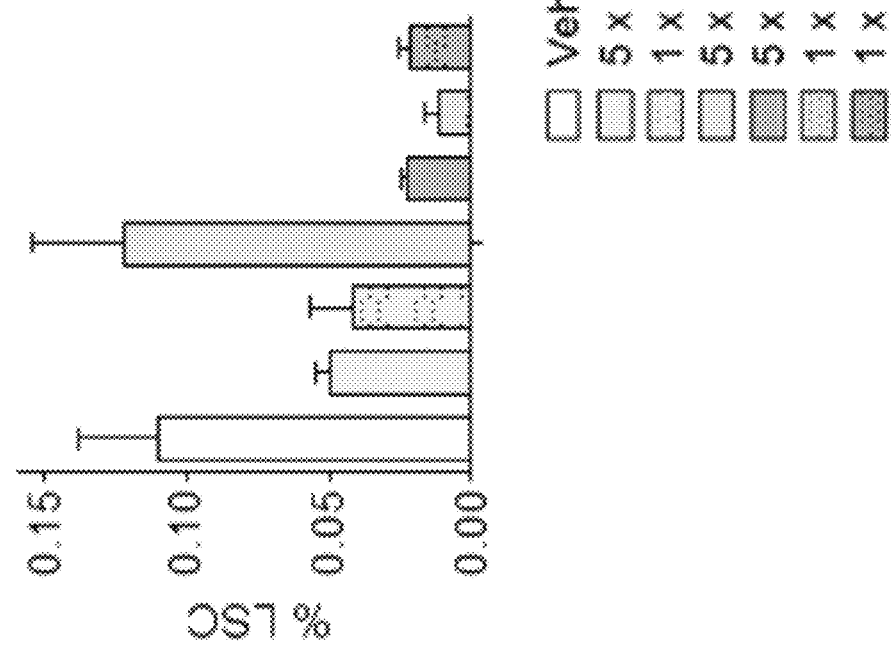

Since LSCs were still present following combination treatment (FIG. 3B), we tested whether maintenance treatment of [Low]DXR might better prevent LSCs from re-establishing leukemia. We used DXR-loaded nanoparticles (nanoDXR) to reduce tissue damage from multiple injections and allow for slow, sustained release of DXR.70 We tested multiple doses of free DXR and nanoDXR to further optimize this treatment and established a low-dose maintenance treatment schedule (FIG. 11A and FIG. 11B). This regimen significantly reduced LSCs compared to free [Low]DXR (FIG. 5C). Median survival was extended to 139 days, a 4.3-fold increase compared to control, with most mice succumbing only after cessation of maintenance [Low]nanoDXR (FIG. 5D and FIG. 5E).

Figure 11D:
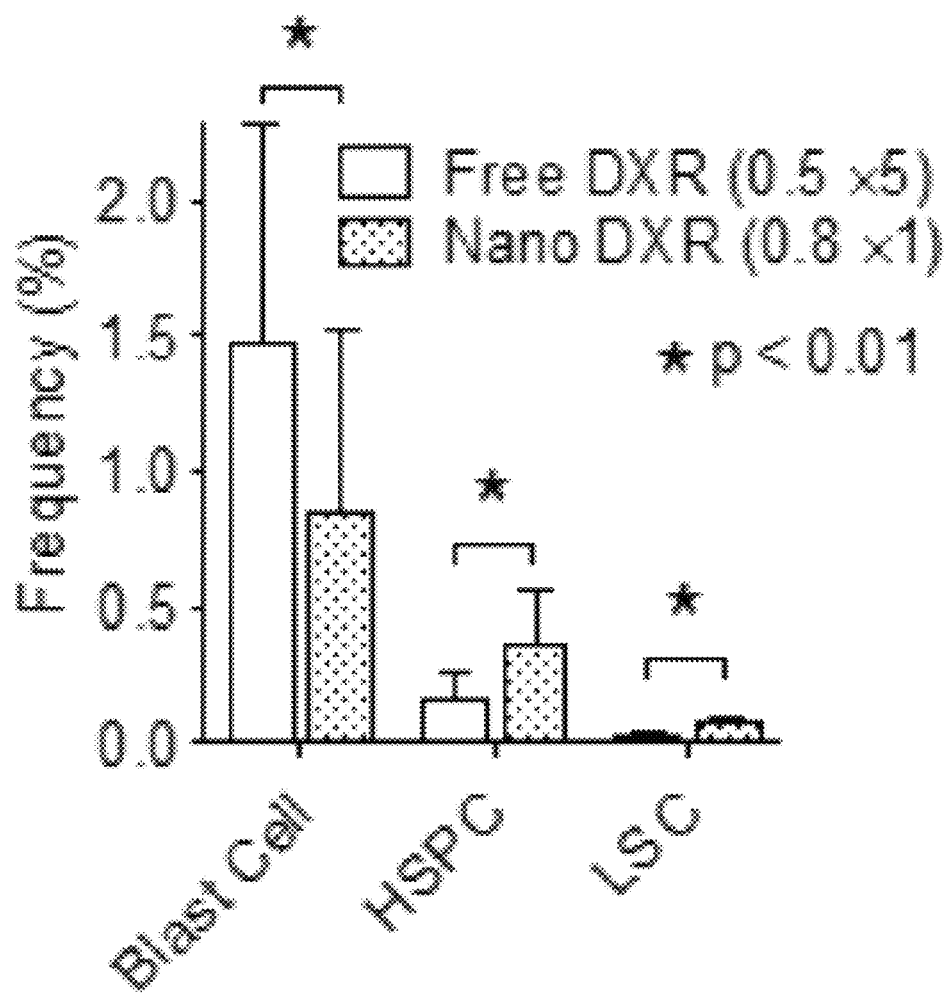

We further determined whether LSCs are not only phenotypically but also functionally reduced by [Low]DXR treatment. To test for tumorigenicity, one week after completion of treatment, we transplanted BM from treated leukemic mice into secondary recipients. Recipients of BM from mice treated with vehicle succumbed to leukemia in a similar manner to primary mutants following induction (FIG. 5F). However, recipients of BM from mice treated with chemotherapy succumbed more rapidly, although 25% of the group showed prolonged survival. Since LSCs are the tumorigenic population, reduced survival of most recipients in this group was consistent with functional LSC expansion induced by chemotherapy (FIG. 3B). Notably, we found that 27/30 recipients of BM from mice treated with [Low]DXR alone remained healthy nearly 6 months post-transplant (FIG. 5F and FIG. 5G). [Low]nanoDXR performed similarly (FIG. 11C and FIG. 11D). These data support the specific targeting of functional LSCs by targeted DXR treatment.

Recipients of BM from chemotherapy+[Low]DXR treated mice had a median survival significantly extended from 44.5 days to 104.5 days compared to the chemotherapy alone group (FIG. 5F). Thus, although combination treatment reduces phenotypic LSCs similarly to [Low]DXR alone (FIG. 3B), functional LSCs can ultimately recover with exposure to chemotherapy and thus the evolution of chemoresistance. Nonetheless, low-dose DXR treatment significantly reduces chemoresistant cells with tumorigenic activity (FIG. 5F and FIG. 11C).

Together, these data show first that functional, tumorigenic LSCs are differentially targeted by chemotherapy and [Low]DXR—with chemotherapy activating LSCs while [Low]DXR targets LSCs in tumorigenic assays. Second, that combination therapy is necessary to substantially improve survival in leukemic mice as chemotherapy eliminates blast cells while [Low]DXR reduces LSC frequency and prevents the resultant chemoresistant LSC expansion. And lastly, that chemotherapy combined with maintenance treatment using targeted/low dose, but not higher, clinical-dose DXR, substantially improves long-term survival (FIGS. 3A-3K and FIGS. 5A-5G).

Example 6

Low-Dose DXR Treatment Reduces Leukemia-Initiating Activity of Human Leukemia Exhibiting Chemoresistant $pS^{52}$-β-Cat+ LSCs To investigate the potential relevance of our animal model findings to patients, we tested whether [Low]DXR treatment could reduce $pS^{552}$-β-cat+ LSCs in pediatric T-ALLs exhibiting minimal residual disease (MRD). We obtained two MRD+ T-ALLs, which were analyzed by FACs for putative LSCs. Given the similar mechanisms responsible for relapse in pediatric ALL as our animal model (Hogan et al. 2011; Bhatla et al. 2012; Bolouri et al. 2018; Griffiths et al. 2010), lack of verified markers for T-ALL LSCs, and c-Kit's role in activating the PI3K pathway, we used similar FACs analysis to identify putative T-ALL LSCs in patient (Pt) samples. Both MRD+ T-ALLs were enriched in $pS^{552}$-β-cat+ LSCs after chemotherapy, either by increasing the LSC frequency (Pt 062) or the $pS^{552}$-β-cat+ fraction of LSCs (Pt 057), further suggesting these cells may represent chemoresistant LSCs (FIGS. 6A-6E). Patient-derived xenograft (PDX) mice were treated with [Low]DXR two weeks after transplantation. FACs analysis revealed that although engraftment of bulk blast cells was not significantly changed by [Low]DXR treatment, $pS^{552}$-β-cat+ LSCs were significantly reduced (FIGS. 6F-6K).

Figure 12A:
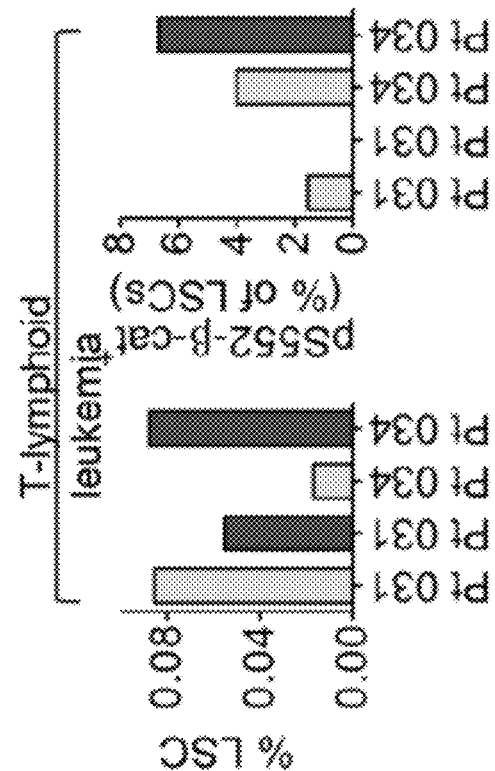
FIGS. 12A-12O show that low-dose DXR treatment reduces leukemia-initiating activity of human leukemia exhibiting chemoresistant pS$^{552}$-β-cat$^+$ LSCs but not in those lacking these cells.
Figure 12B:
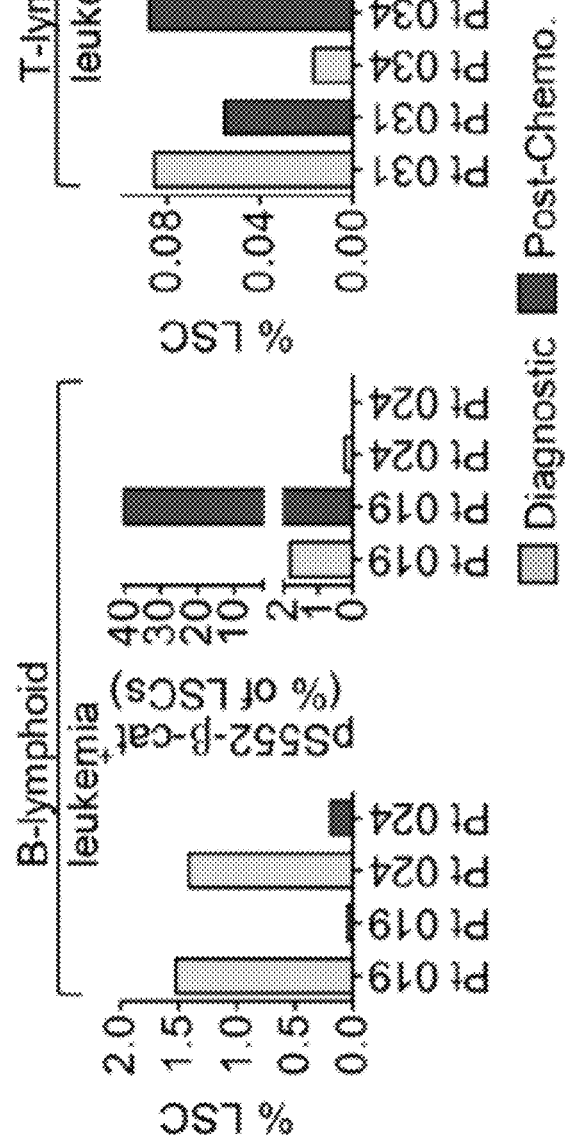
FIG. 12B is the summary of pediatric leukemia patients analyzed by FACS for LSCs and pS$^{552}$-β-cat$^+$ LSCs. T-lymphoid LSCs were identified as enriched in CD45$^+$ CD34$^+$ CD19$^+$ and CD45$^+$ c-Kit$^+$CD3$^+$ cells, respectively (Rabbani et al. 2005; Gewirtz, 1999; Gothert et al. 2005; Barker et al. 2018; Hsu et al. 2018). Bone marrow samples at diagnosis (untreated) are shown in grey; same-patient samples at day 29 post-chemotherapy treatment are red. Patient (Pt) samples 019 and 034, T-lymphoid leukemias exhibiting chemoresistant pS$^{552}$-β-cat$^+$ LSCs, were subjected to further in vivo treatment and analysis. Pt 024 and 031, B-lymphoid acute leukemias lacking chemoresistant pS$^{552}$-β-cat$^+$ LSCs, were also tested.
Figure 12C:
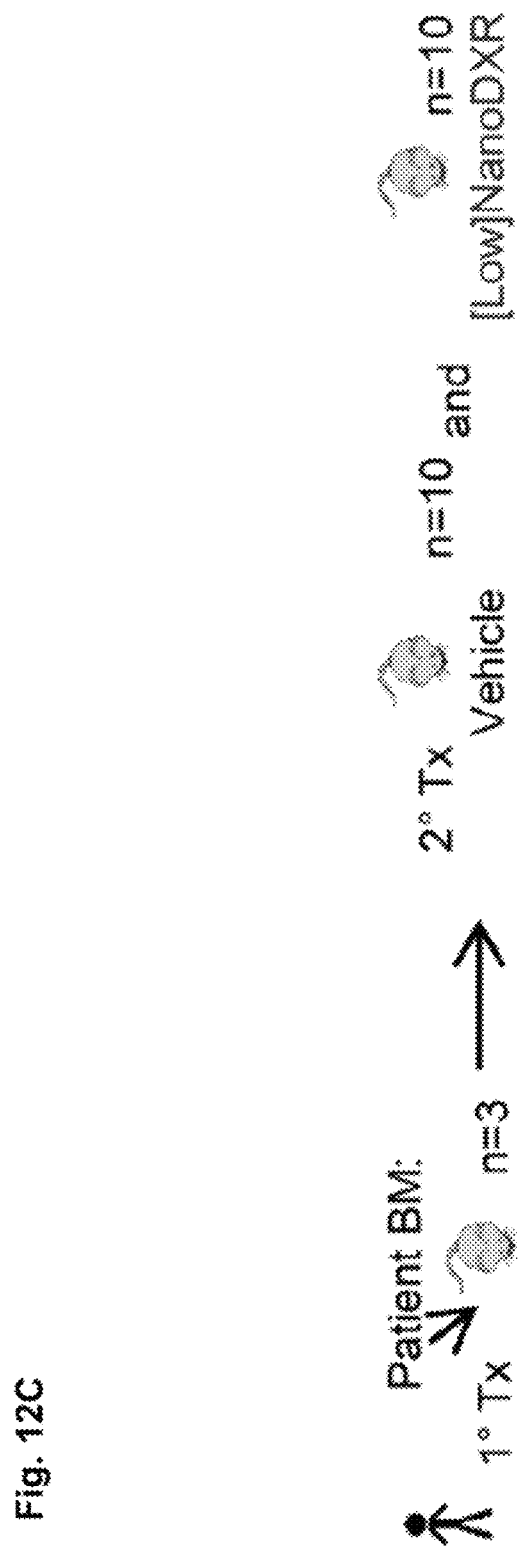
FIG. 12C provides the experimental schematic of establishment and treatment of patient-derived xenografts (PDX).
Figure 12D:
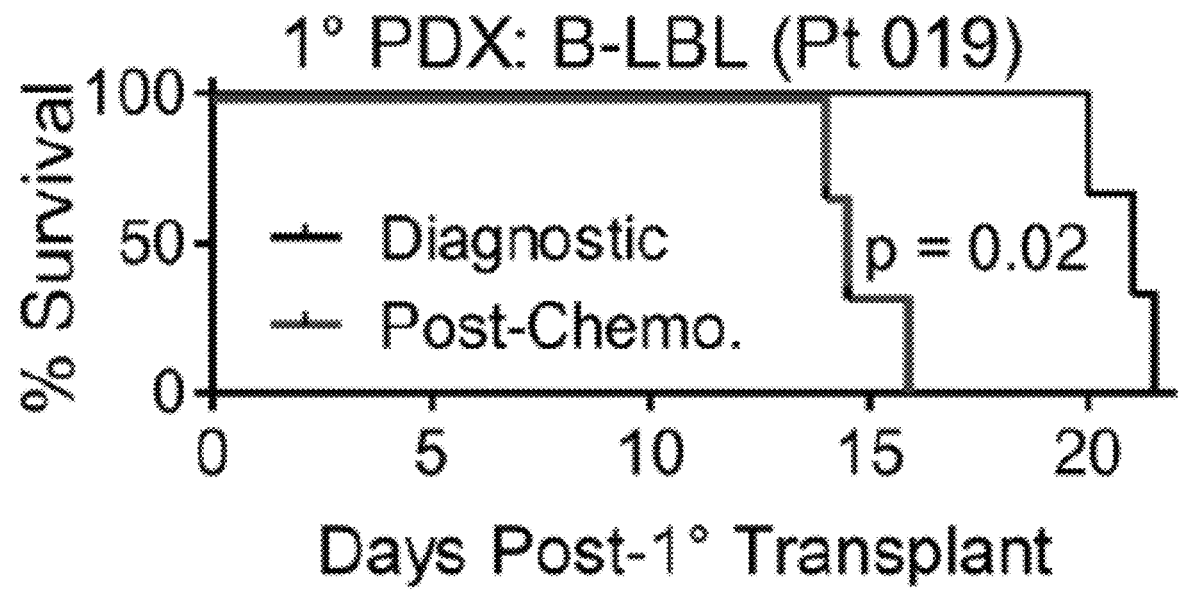
FIG. 12D is the Kaplan-Meier survival curve of 1° PDX recipients of diagnostic and post-chemotherapy BM from Pt 019.
Figure 12E:
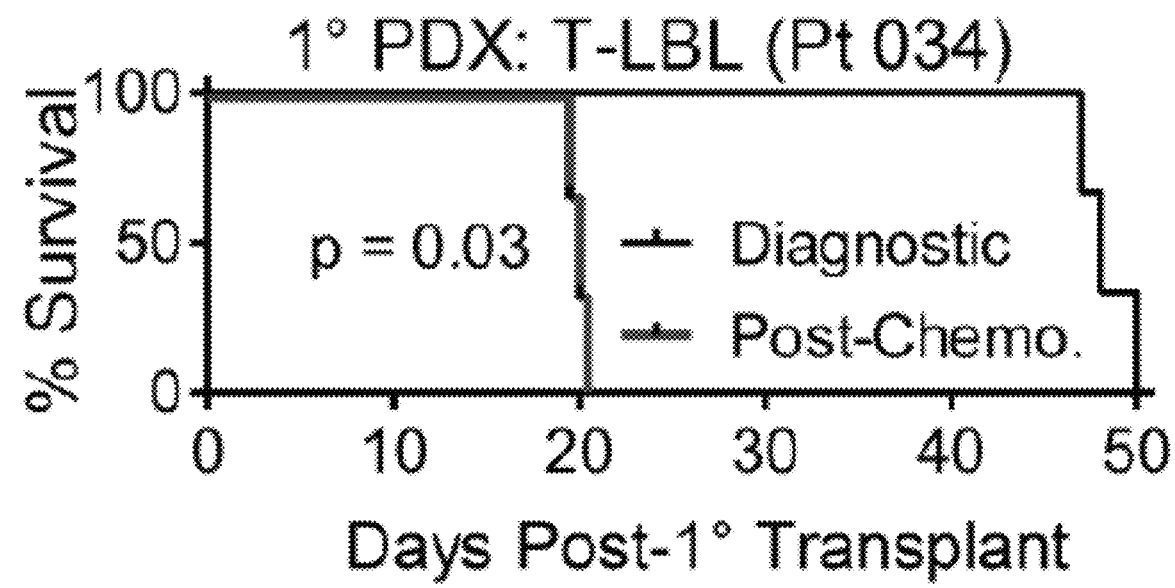
FIG. 12E is the Kaplan-Meier survival curve of 1° PDX recipients of diagnostic and post-chemotherapy BM from Pt 034.
Figure 12F:
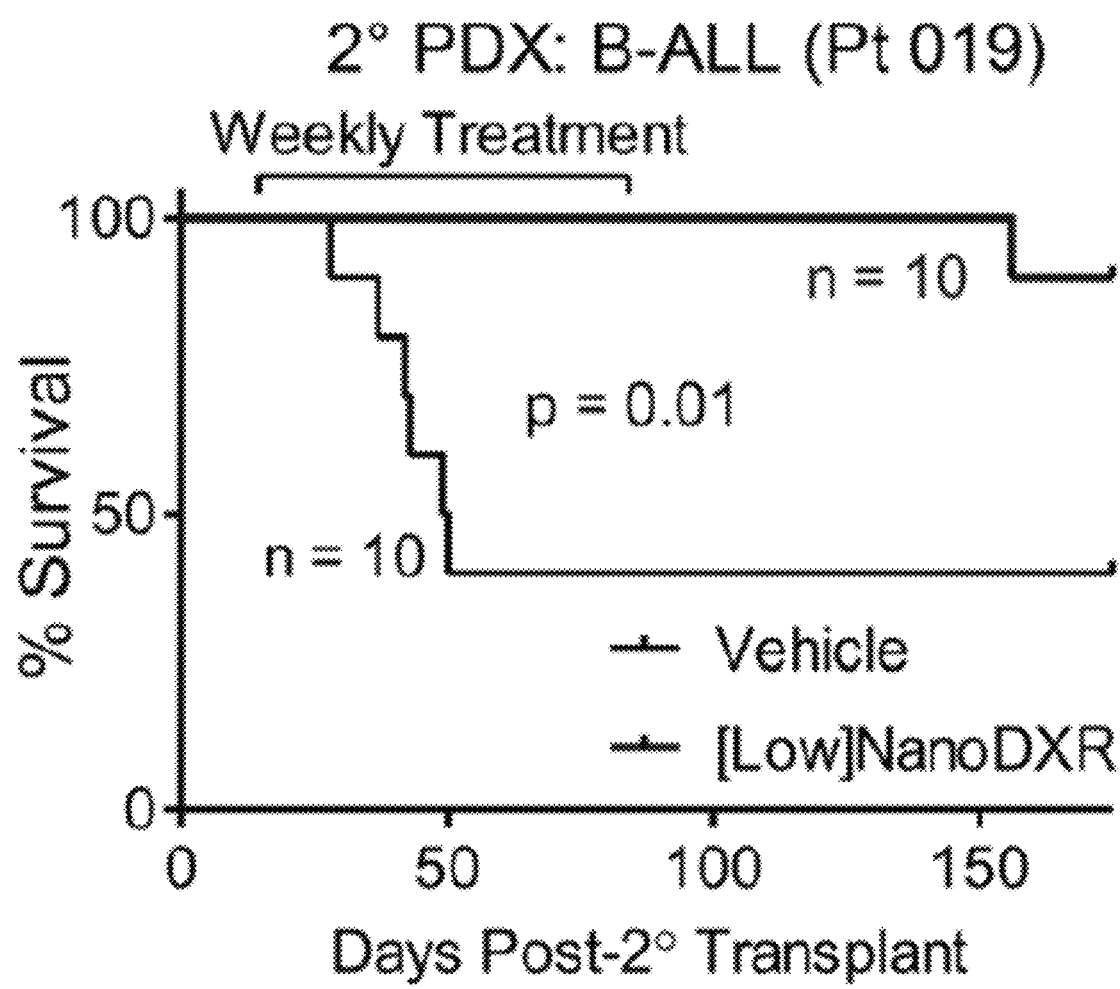
FIG. 12F is the Kaplan-Meier survival curve for 2° PDX recipients treated with vehicle or [Low]nanoDXR. Bone marrow was harvested from 1° recipients of diagnostic BM, transplanted into a larger set of 2° PDX recipients and treated with [Low] NanoDXR starting at day 14 post-transplant and continuing for up to 10 weeks.
Figure 12G:
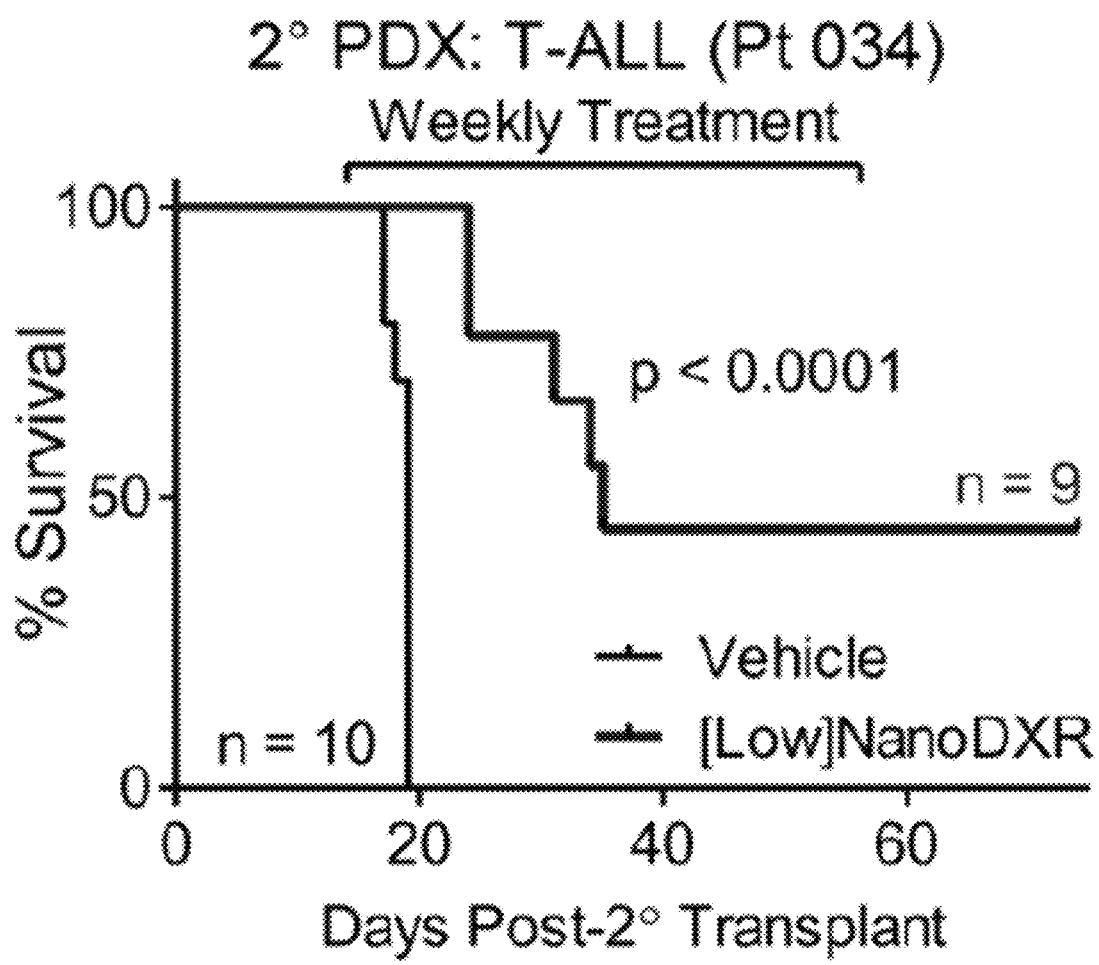
FIG. 12G is the Kaplan-Meier survival curve for 2° PDX recipients treated with vehicle or [Low]nanoDXR. Bone marrow was harvested from 1° recipients of post-chemotherapy BM, transplanted into a larger set of 2° PDX recipients and treated with [Low] NanoDXR starting at day 14 post-transplant and continuing for up to 10 weeks.
Figure 12H:
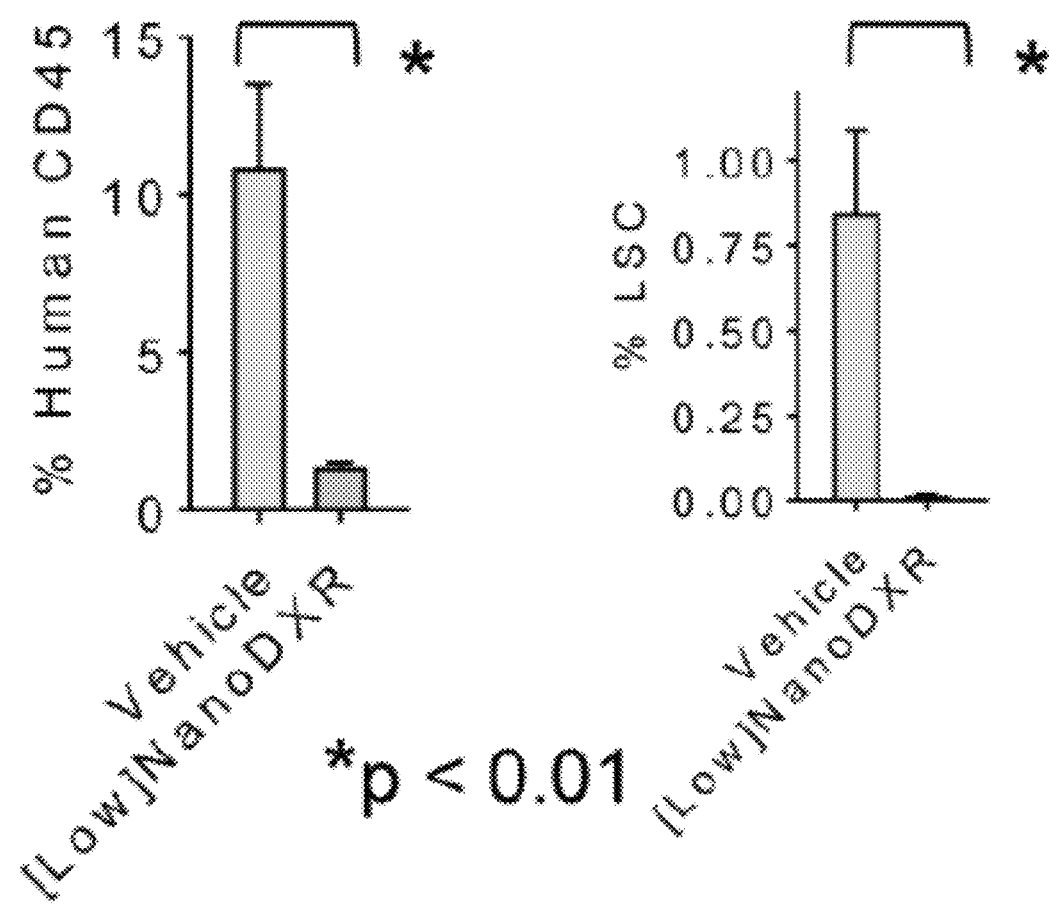
FIG. 12H shows that FACs analysis was performed on 2° PDX recipient BM from FIG. 12F. Human CD45$^+$ and human LSC engraftment was determined after succumbing to leukemia or at experimental endpoint. Graphs indicate frequency (%)+Std. Dev.
Figure 12I:
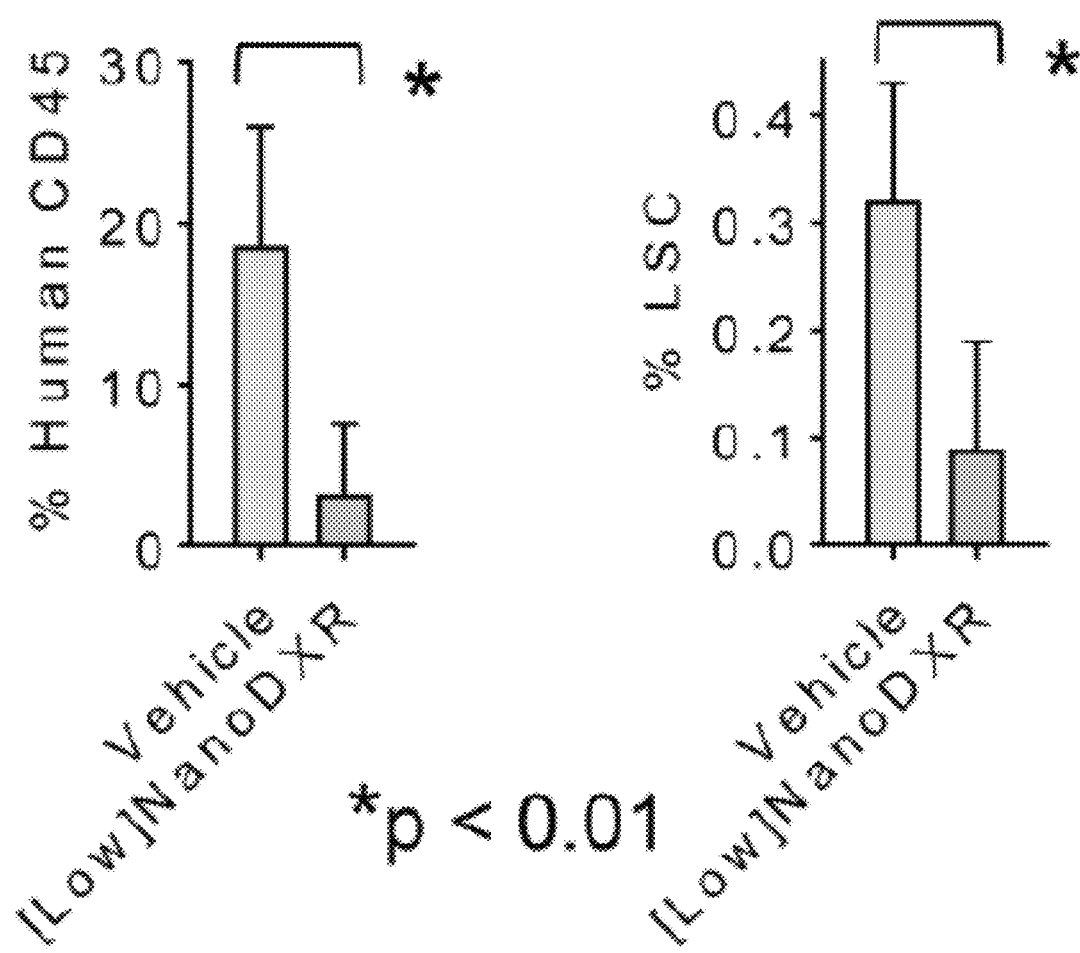
FIG. 12I shows that FACs analysis was performed on 2 PDX recipient BM from FIG. 12G. Human CD45$^+$ and human LSC engraftment was determined after succumbing to leukemia or at experimental endpoint. Graphs indicate frequency (%)+Std. Dev.
Figure 12J:
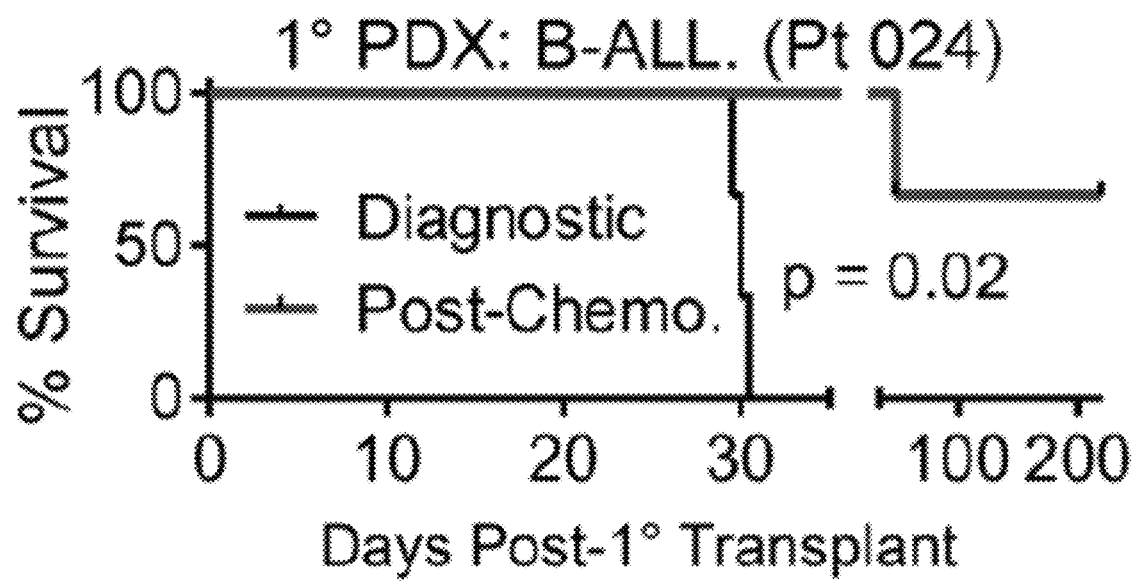
FIG. 12J shows the analysis of patient-derived xenografts (PDX) from Pt 024, which lack chemoresistant pS$^{552}$-β-cat$^+$ LSCs.
Figure 12K:
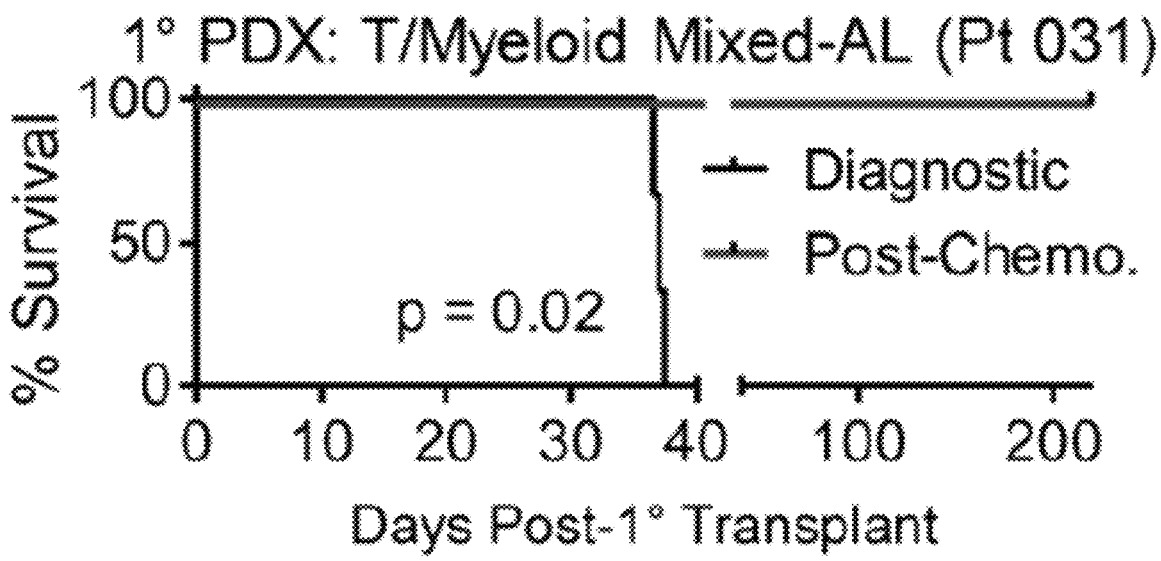
FIG. 12K shows the analysis of patient-derived xenografts (PDX) from Pt 031, which lack chemoresistant pS$^{552}$-β-cat$^+$ LSCs.
Figure 12L:
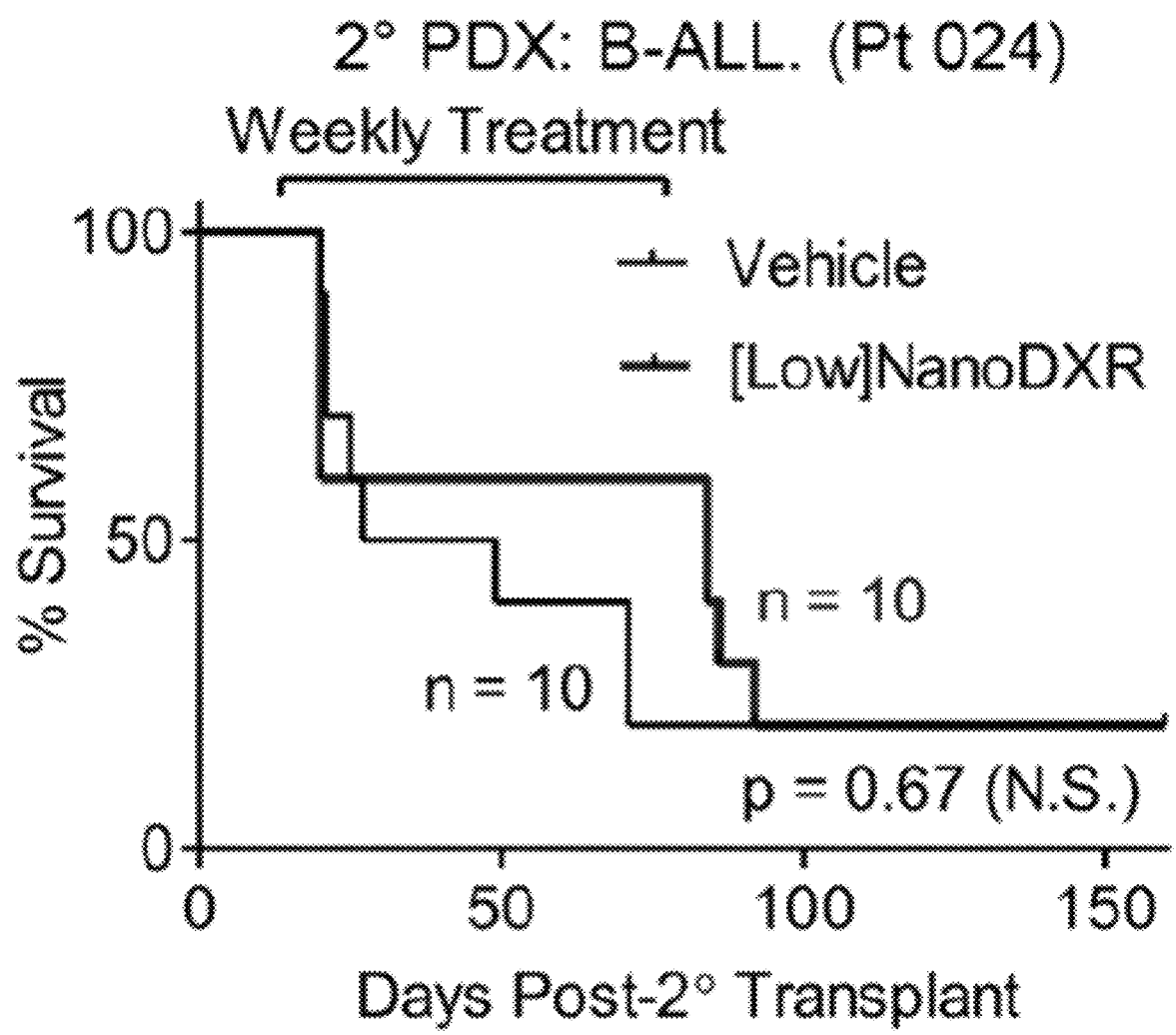
FIG. 12L is the Kaplan-Meier survival curve for 2° PDX recipients treated with vehicle or [Low]nanoDXR. Bone marrow was harvested from 1° recipients of diagnostic BM (FIG. 12D), transplanted into a larger set of 2° PDX recipients and treated with [Low] NanoDXR starting at day 14 post-transplant and continuing for up to 10 weeks.
Figure 12M:
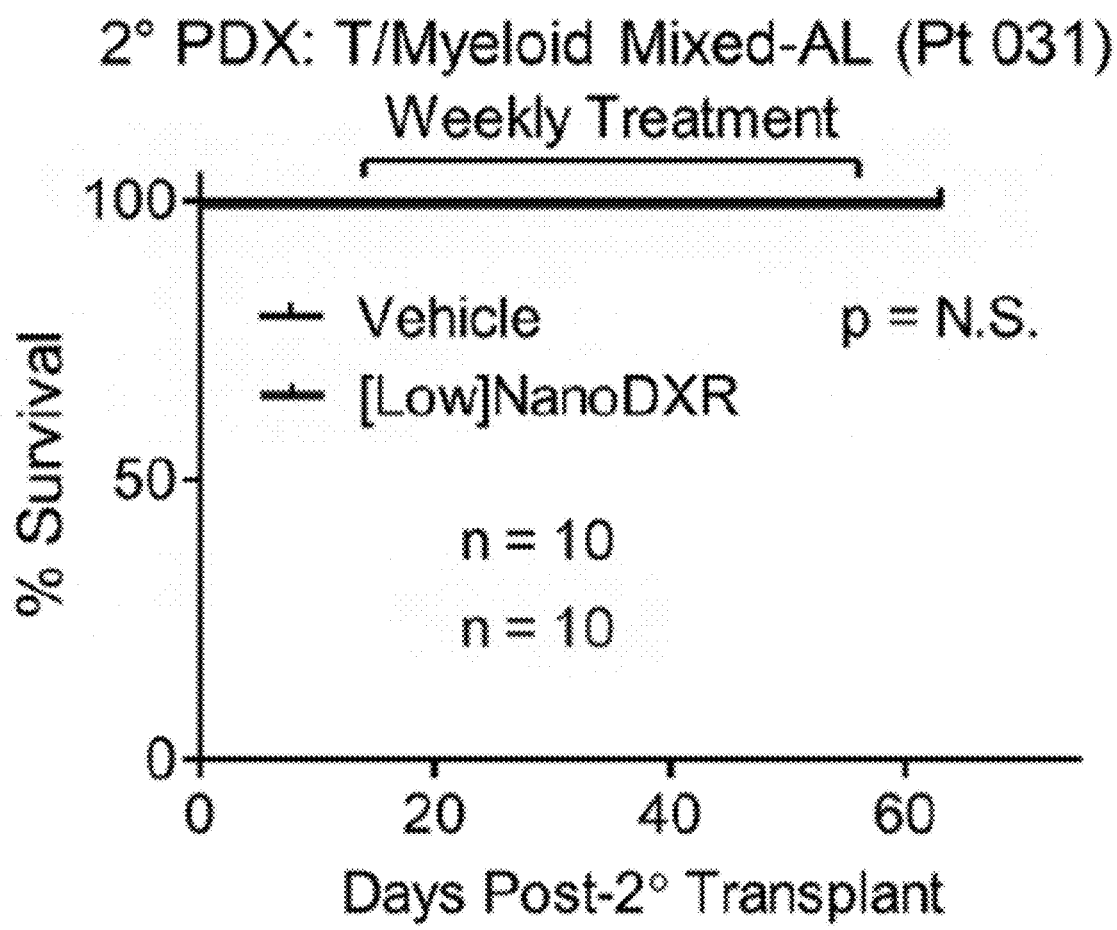
FIG. 12M is the Kaplan-Meier survival curve for 2° PDX recipients treated with vehicle or [Low]nanoDXR. Bone marrow was harvested from 1° recipients of diagnostic BM (FIG. 12E), transplanted into a larger set of 2° PDX recipients and treated with [Low] NanoDXR starting at day 14 post-transplant and continuing for up to 10 weeks.
Figure 12N:
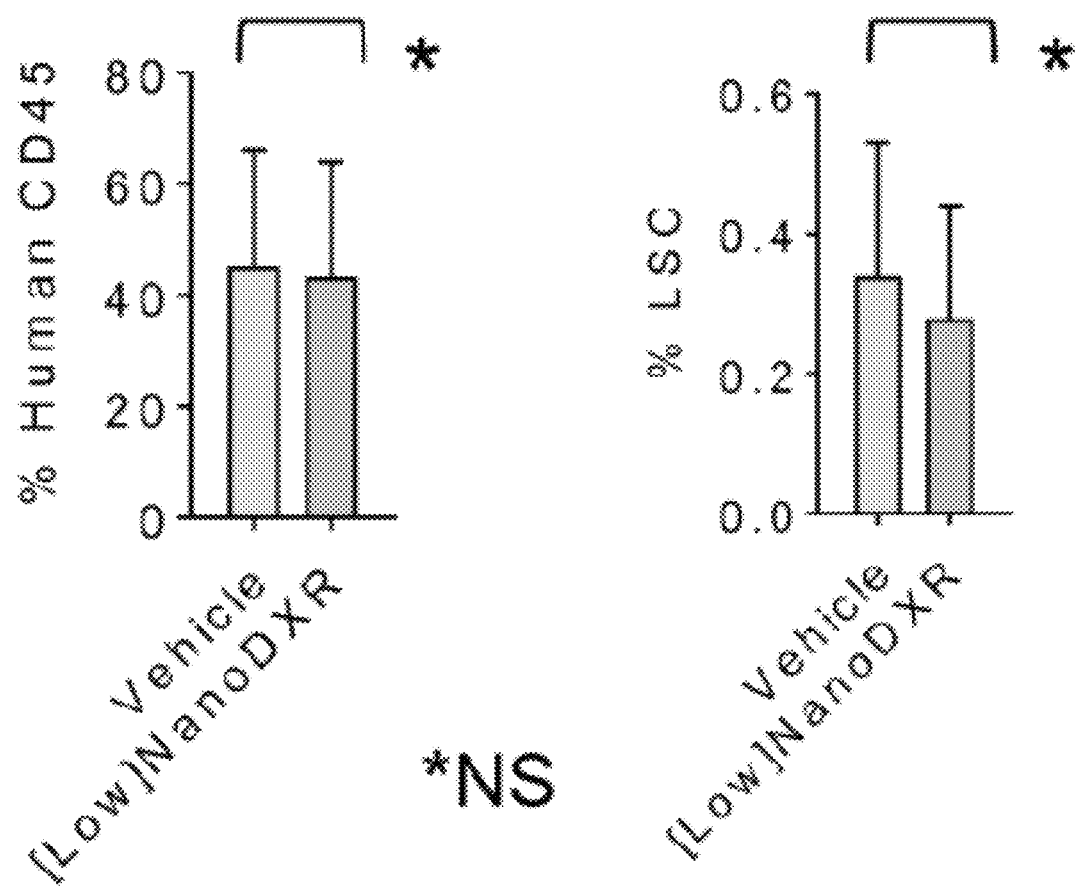
FIG. 12N shows that FACs analysis was performed on 2° PDX recipient BM from FIG. 12D. Human CD45$^+$ and human LSC engraftment was determined after succumbing to leukemia or at experimental endpoint. Graphs indicate frequency (%)+Std. Dev. (N.S.=not significant).
Figure 12O:
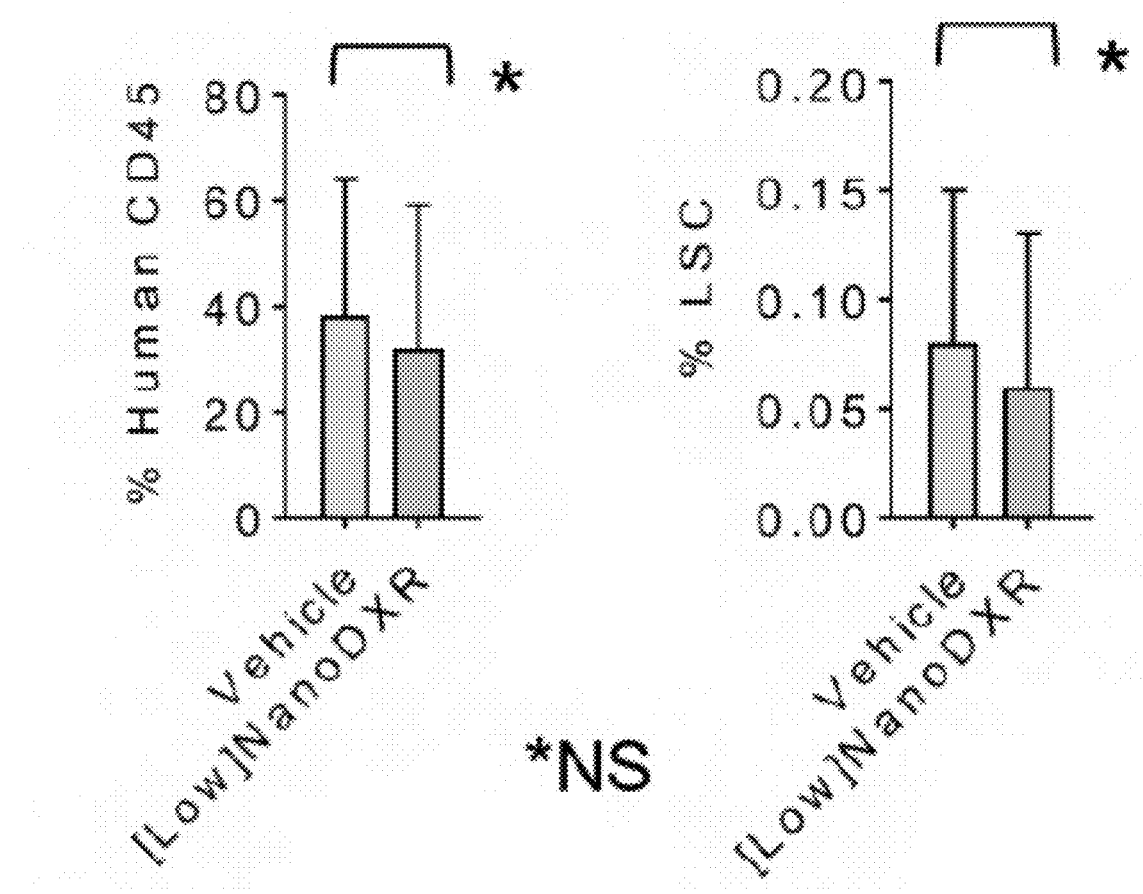

To determine how indicative chemoresistant human LSCs expressing $pS^{552}$-β-catenin were to tumorigenic capacity and further test how effective [Low]DXR is at targeting them, additional leukemia BM samples were analyzed by FACS for phenotypic LSCs (Hong et al. 2008; Castor et al. 2005; Kong et al. 2008; Wilson et al. 2010; Eguchi et al. 2015) and $pS^{52}$-β-catenin expression. We obtained paired samples not only at diagnosis but also at day 29 post-chemotherapy treatment with sufficient cell number and viability for in vivo PDX analysis for several BM samples. We found that some Pt samples contained chemoresistant $pS^{552}$-β-cat+ LSCs (FIG. 12A and FIG. 12B; Table 2). We selected diagnostic and post-chemotherapy treated B and T-lymphoid leukemia samples that either had or lacked chemoresistant $pS^{552}$-β-cat+ LSCs for tumorigenic analysis (FIG. 12C). Samples containing chemoresistant $pS^{552}$-β-cat+ LSCs showed rapid leukemia development in NSG recipients, with post-chemotherapy BM samples resulting in recipients succumbing to leukemia significantly faster than the same sample collected at diagnosis (FIG. 12D and FIG. 12E). However, while samples lacking chemoresistant $pS^{552}$-β-cat+ LSCs resulted in leukemogenesis using diagnostic BM, post-chemotherapy BM from these particular samples did not induce leukemia in recipients (FIG. 12J and FIG. 12K). These results are consistent with enriched tumorigenicity of chemoresistant but not chemosensitive $pS^{552}$-β-cat+ LSCs in patient samples.

Since low-dose DXR treatment could prevent the establishment of leukemia in our animal leukemia model (FIG. 5F), we tested whether it could also inhibit tumorigenicity of patient BM containing chemoresistant $pS^{552}$-β-cat+ LSCs. BM was harvested from primary (1°) recipients and transplanted into secondary (2°) recipients, which were treated with low-dose DXR or vehicle control. Recipients of Pt samples containing chemoresistant $pS^{552}$-β-cat+ LSCs showed significantly improved survival, reduced leukemia engraftment and LSC frequency compared to vehicle control (FIGS. 12F-12I); however, those lacking chemoresistant $pS^{552}$-β-cat+ LSCs showed no significant difference in survival, leukemia engraftment or LSC frequency (FIGS. 12L-12O). These data based on detailed in vivo treatment of PDX recipient mice using 4 ALL Pt samples exhibiting chemoresistance and 2 Pt samples exhibiting chemosensitivity are consistent with low-dose DXR's potential for targeting chemoresistant $pS^{552}$-β-cat+ LSCs not only in our animal model but patient samples.

TABLE 2

Pediatric ALL Sample Characteristics and Analysis.

| Diagnosis | Sample # | Diagnostic BM | Post-Chemo BM | 1° Transplant | 2° Tranplant | Induction Protocol | Chemo |
|---|---|---|---|---|---|---|---|
| B-ALL | 006 | X | | Diag. | | AALL0932 | Dex, Vin, Peg |
| B-ALL | 007 | X | | Diag. | | AALL1131 (DS arm) | Dex, Vin, Peg |
| B-ALL | 010 | X | | Diag. | | AALL0932 | Dex, Vin, Peg |
| B-ALL | 012 | X | | Diag. | | AALL0932 | Dex, Vin, Peg |
| B-ALL | 015 | X | X | | | AALL0932 | Dex, Vin, Peg |
| B-ALL | 019 | X | X | Diag.; Post-Chemo. | Diag. | AALL0932 | Dex, Vin, Peg |
| B-ALL | 022 | X | | | | AALL0932 | Dex, Vin, Peg |
| B-ALL | 024 | X | X | Diag.; Post-Chemo. | Diag. | AALL0932 | Dex, Vin, Peg |
| B-ALL | 028 | X | | | | AALL1131 | Dex, Vin, Peg, DNO |
| B-ALL | 029 | X | | | | AALL0932 | Dex, Vin, Peg |
| T-Mye | 031 | X | X | Diag.; Post-Chemo. | Diag. | AALL1231 | Dex, Vin, Peg, DNO |
| T-ALL | 034 | X | X | Diag.; Post-Chemo. | Post-Chemo. | AALL1231 | Dex, Vin, Peg, DNO |
| B-ALL | 037 | X | X | Diag. | | AALL0932 | Dex, Vin, Peg |

| Diagnosis | Sample # | BM Blasts Day 0 | BM Blasts Day 29 | Remission Day 29 | MRD | LSC (%) Diagnostic/Post-Chemo. BM | $pS^{552}$-βcat+ (% of LSC) Diagnostic/Post-Chemo. BM |
|---|---|---|---|---|---|---|---|
| B-ALL | 006 | 85% | 0% | Yes | Neg. | 0.81 | 0.686 |
| B-ALL | 007 | 95% | 0% | Yes | Neg. | 0.40 | 0.539 |
| B-ALL | 010 | 35-45% | 0%-0.01% | Yes | Pos. | 0.20 | 1.69/1.28 |
| B-ALL | 012 | 98% | 0.02% | Yes | Pos. | 0.32 | 1.28 |
| B-ALL | 015 | 80% | 0% | Yes | Neg. | 0.25/0.11 | 1.37/37.6 |
| B-ALL | 019 | 80% | 0% | Yes | Neg. | 1.52/0.05 | 1.82/40.2 |
| B-ALL | 022 | 85% | 0% | Yes | Neg. | 0.68 | 1.2 |
| B-ALL | 024 | 90% | 0% | Yes | Neg. | 1.41/0.19 | 0.249/0.000 |
| B-ALL | 028 | 93% | 0% | Yes | Neg. | 1.11 | 0.951 |
| B-ALL | 029 | 92% | 0% | Yes | Neg. | 0.49 | 1.15 |
| T-Mye | 031 | 85% | 2.80% | Partial | Pos. | 0.09/0.06 | 1.57/0.000 |
| T-ALL | 034 | 73% | 17% | No | Pos. | 0.02/0.09 | 4.00/6.67 |
| B-ALL | 037 | 84% | 5-10% | No | Pos. | 0.21/0.92 | 7.10/3.81 |

(B-, T-ALL = B-cell, T-cell acute lymphoblastic leukemia, respectively; T-Mye = T/Myeloid Mixed Acute Leukemia)
(Dex = Dexamethasone; Vin = Vincristine; Peg = Pagasparagase; DNO = Daunorubicin)

Figure 6A:
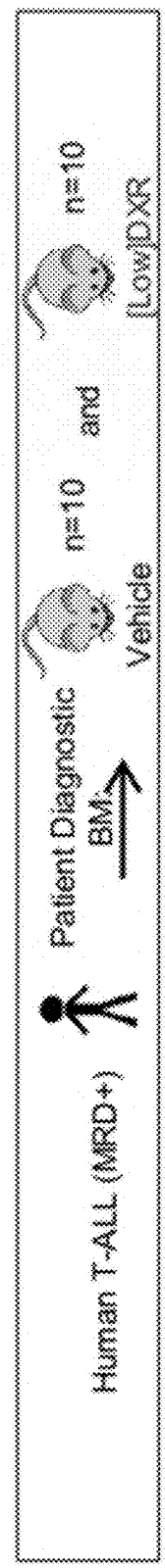
FIGS. 6A-6N show that low-dose DXR treatment reduces persistent $pS^{552}$-β-cat$^+$ cells from MRD$^+$ human leukemia.
Figure 6L:
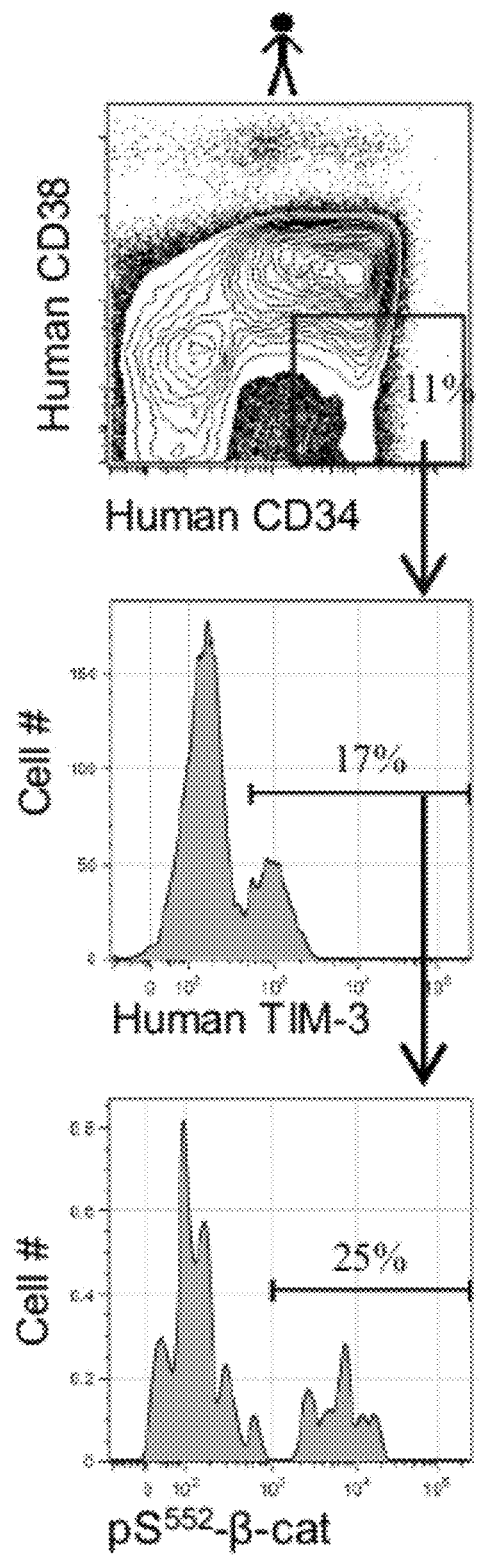
FIG. 6L shows that relapsed/refractory adult AML patients received one cycle of low-dose DNR (6.75 mg/m$^2$ daily for 5 days (days 1-5). Pre-treatment (day 0) and post-treatment BM samples were collected and analyzed by FACs. Shown are representative FACs plots showing gating strategy for analysis.
Figure 6M:
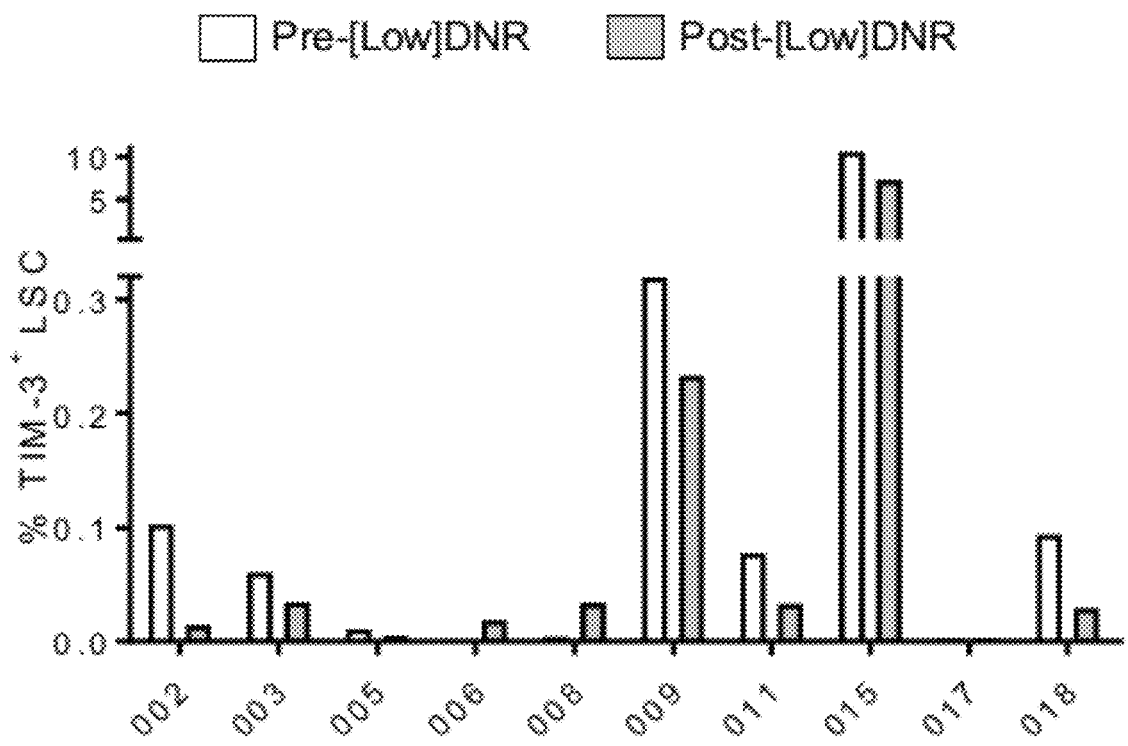
FIG. 6M shows that LSCs (identified as CD45$^+$ CD34$^+$ CD38− TIM-3$^+$ cells) (Malta et al. 2018; Jinesh et al. 2017) was quantified according to gating represented in FIG. 6L at pre- and post-low dose DNR as indicated.
Figure 6N:
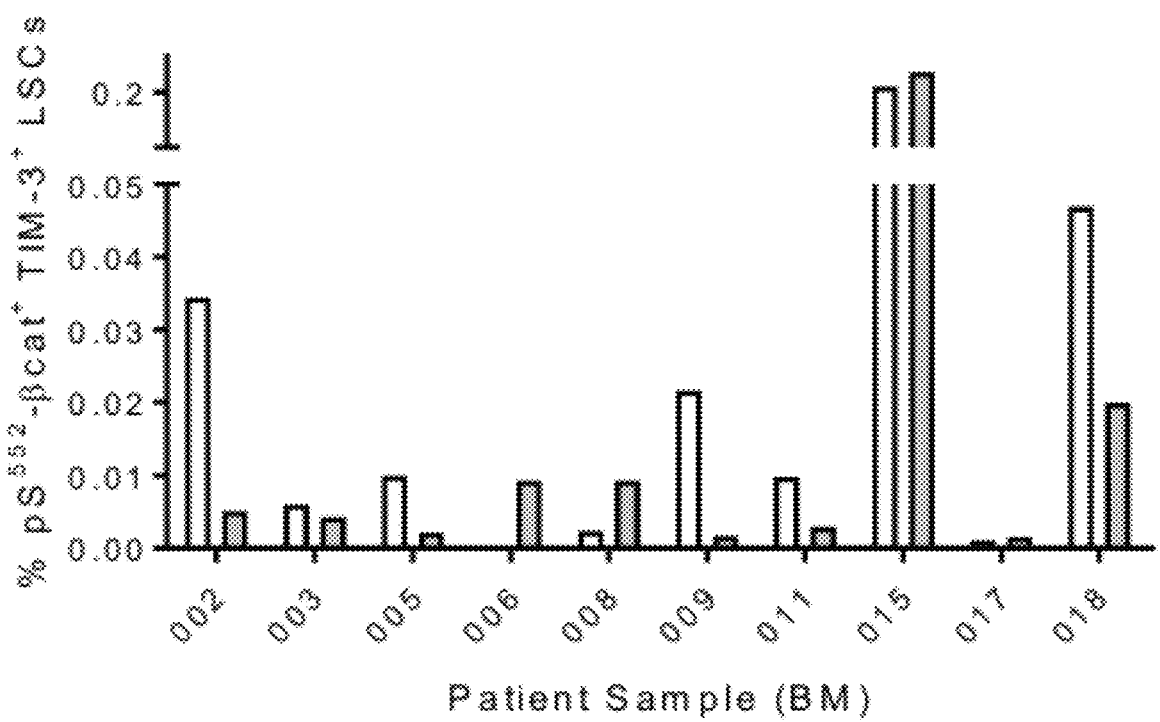
Figure 13A:
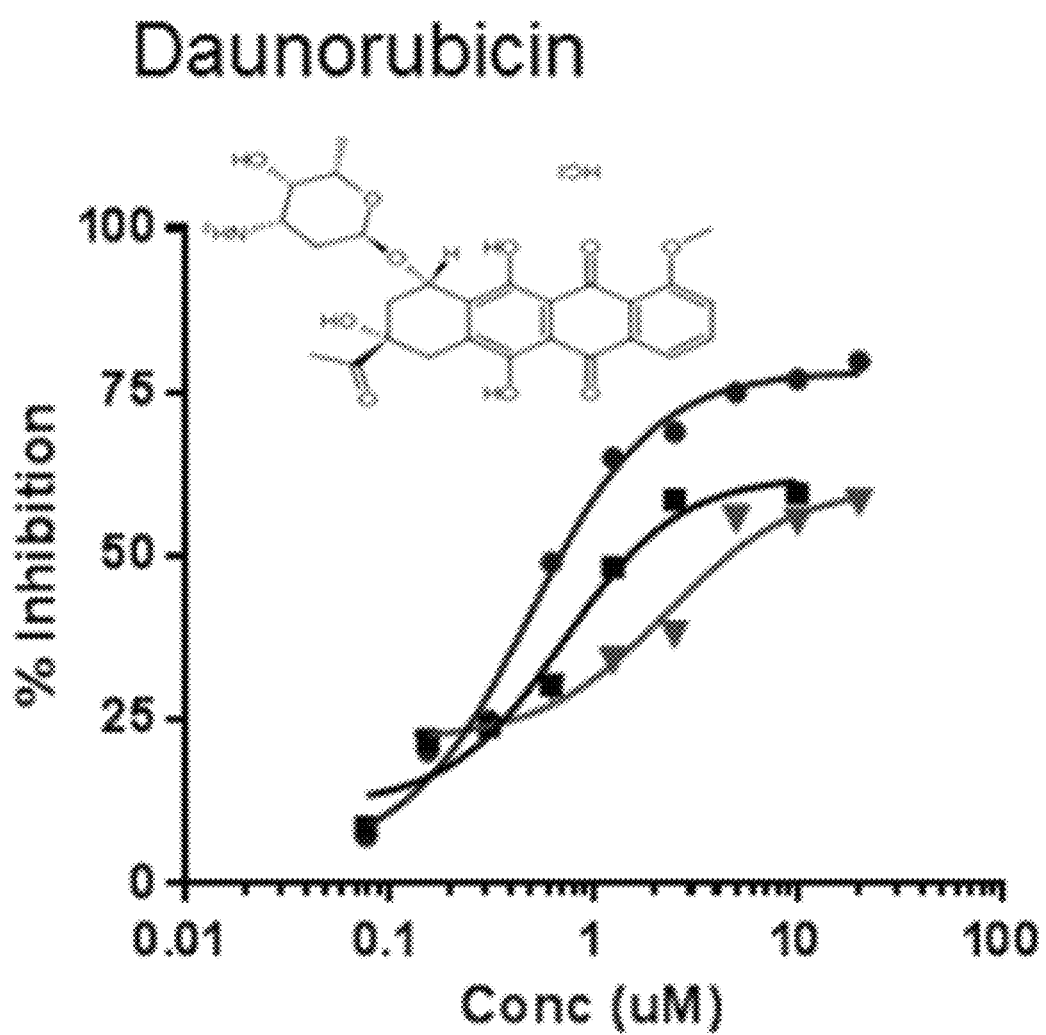
FIGS. 13A-13B show that low-dose daunorubicin performs similarly to low-dose doxorubicin.
Figure 13B:
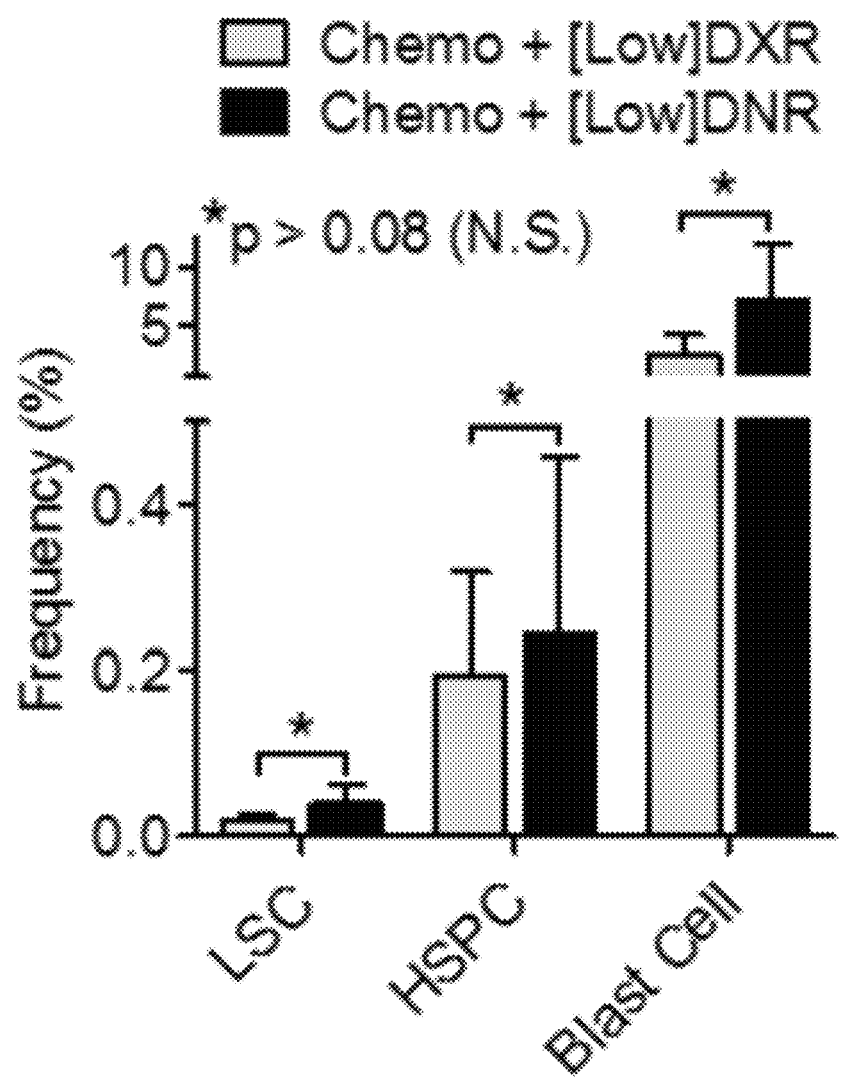

To further test whether chemoresistant pS$^{52}$-β-cat$^+$ LSCs could be reduced in patients, we conducted a pilot clinical trial using low-dose anthracycline treatment on relapse or refractory adult AML patients (see Supplemental Methods and Table 3 for Pt characteristics). Daunorubicin (DNR) is the anthracycline analog of DXR used in AML treatment and similarly inhibits pS$^{552}$-β-catenin (FIGS. 13A-13B). Patients were treated with one cycle of low-dose DNR (6.75 mg/m$^2$; $\frac{1}{40}^{th}$ the standard dose) for 5 consecutive days and BM samples were drawn at day 0 (pre-treatment) and day 8 post-treatment. FACS analysis determined the frequency of AML LSCs, distinguished from HSPCs by TIM-3 expression (Kikushige et al. 2010; Jan et al. 2011), pre- and post-low-dose DNR treatment. LSCs were typically rare, as expected (Kikushige et al. 2010), showing a pattern of response to low-dose DNR similar to pS$^2$-β-cat$^+$ LSCs. Specifically, 5/10 patients (Pt 002, 005, 009, 011, and 018) showed substantial reductions in pS$^{552}$-β-cat$^+$ LSCs, 3/8 (Pt 003, 015, and 017) were unchanged, and 2/8 (Pt 006 and 008) initially had very low or absent pS$^{552}$-β-cat$^+$ LSCs (FIGS. 6L-6N). While future studies will determine the impact on patient outcomes of low-dose anthracycline treatment, these data indicate that pS$^{552}$-β-cat$^+$ LSCs can be reduced in 5/10 relapsed/refractory patients.

interaction at low doses, we found that DXR could be repurposed as a targeted therapy for resistant LSCs, in part by inhibiting multiple immune checkpoints. Notably, LSCs but not blast cells exhibit unique properties of immune resistance, which can be reduced with low-dose DXR.

While our data show that immune resistance is a major mechanism for LSCs' role in tumor escape, our pre-clinical studies involved immunocompromised mice, so intrinsic mechanisms must also occur. The cooperative role of the Wnt/β-catenin and PI3K/Akt pathway in stem cell regulation and the hijacking of stem cell properties by leukemia-initiating cells likely represent an additional mechanism for low-dose DXR's effect. Recent links between tumor-initiating stem cells and immune resistance may indicate that these properties are not mutually exclusive (Miao et al. 2019).

Figure 14A:
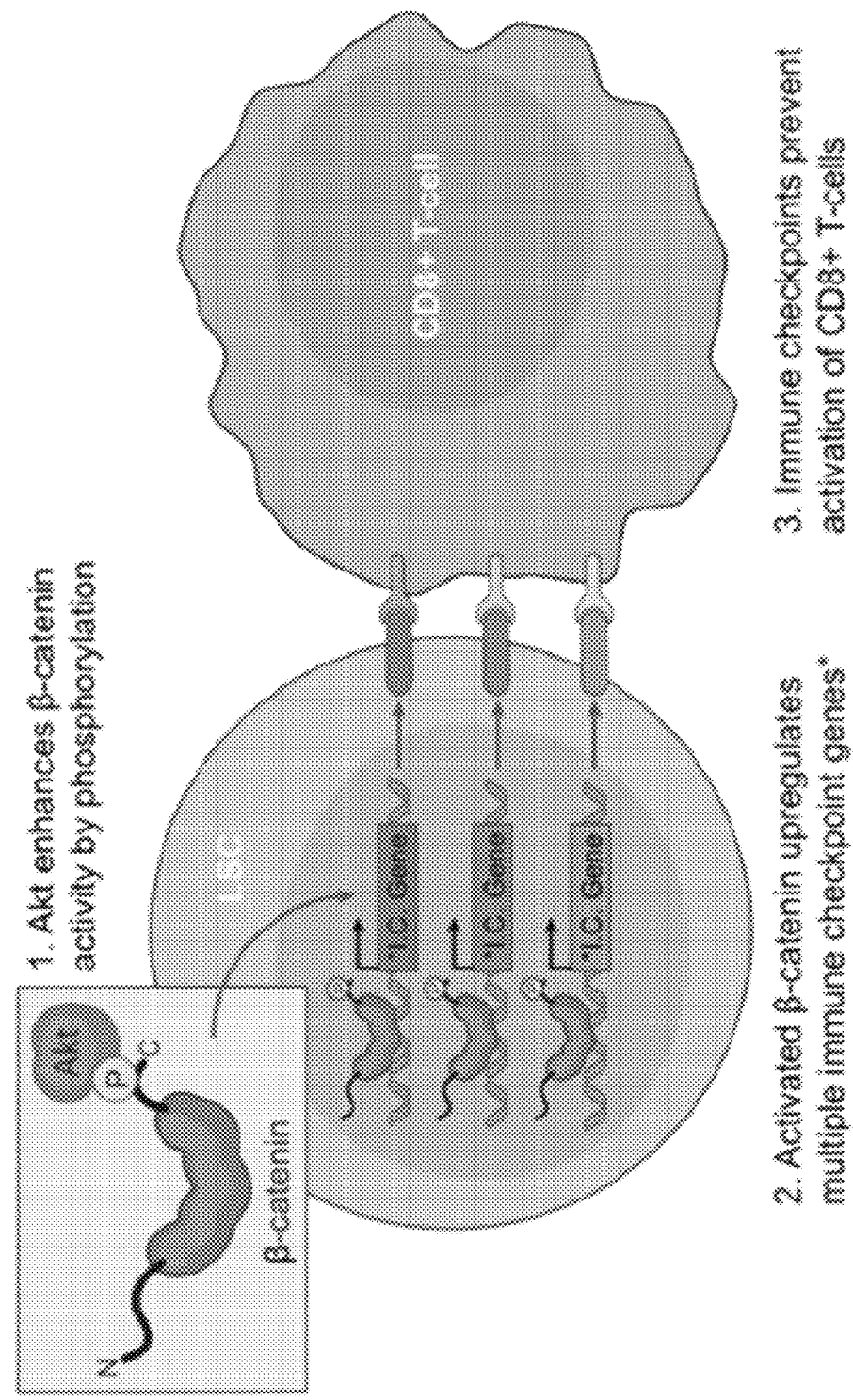

In contrast to our targeted use, typical clinical doses of DXR, while highly effective at reducing the absolute numbers of all cell types, stimulated resistance mechanisms, including immune checkpoints, in LSCs. However, low-dose DXR uniquely targets LSCs, which are responsible for tumor escape (FIGS. 14A-14B). Despite using chemotherapeutic drugs for more than half a century, their mechanism of action is still not fully understood (Weinberg, 2014). DXR

TABLE 3

Relapsed/Refactory AML Patient Characteristics.

| Patient Study ID | M/F | Age | Disease Characteristics | de novo vs Secondary | # Prior Treatments | Prior Treatment | Original Diagnosis Cytogenetics | Study Entry Cytogenetics | NGS |
|---|---|---|---|---|---|---|---|---|---|
| AML 002 | M | 70 | 1st relapse | de novo | 1 | 7 + 3 | tetrasomy 13 | tetrasomy 13 | JAK3; RUNX1 |
| AML 003 | M | 58 | Primary induction failure | de novo | 3 | 7 + 3; hidac; dacogen | complex | complex | TP53 |
| AML 005 | F |  | 2nd relapse | de novo | 3 | 7 + 3; 2 cycles HIDAC; mylotarg; haplo bone marrow | inversion 16 | normal? | different panel used but 0 |
| AML 006 | M | 59 | Primary induction failure | secondary to MDS | 2 | 7 + 3; hidac | Normal | Normal | CBL |
| AML 008 | F | 40 | 1st relapse | de novo |  | 7 + 3/SCT; Dacogen; Flu-Ara-C | MLL; complex | MLL; complex | none |
| AML 009 | F | 77 | 2nd relapse | secondary to MDS | 2 | dacogen/ sapecitabine; dacogen |  | del 7; der1q | NA |
| AML 011 | F | 74 | 1st relapse | de novo | 1 | Dacogen | Normal | trisomy 4 | IDH1; NPM1; NF1; TET2 |
| AML 015 | M | 66 | 1st relapse | de novo | 3 | 7 + 3, hidac consolidation; dacogen salvage; INCB salvage | complex | complex | ASXL1; STAG2 |

Example 7

Discussion

Considering the cooperative role of the Wnt/β-catenin and PI3K/Akt pathway in resistance to anti-cancer therapies, including immune escape, the Pten:β-cat$^{Act}$ double mutant mice served as an ideal model to study cancer therapy resistance. Using this model, we found that cooperative Akt:β-catenin signaling is particularly critical for therapy-resistant LSCs. Investigating the mechanism underlying this resistance, we unexpectedly found that β-catenin binds to multiple immune checkpoint genes, which are expressed on LSCs. In identifying DXR as an inhibitor of Akt:β-catenin acts as a topoisomerase II inhibitor at high concentrations and, even though it exhibits the broadest spectrum of anti-cancer activity known, causes severe cardiotoxicity, necessitating a maximum lifetime dosage (Rabbani et al. 2005). Furthermore, DNA damage at high doses increases the risk of secondary malignancy. Recent work has shown that levels of topoisomerase II is often a poor predictor of DXR's clinical activity and our work suggests a more efficacious use for this drug, which continues to serve as a backbone of anti-cancer therapy for multiple tumor types (Nitiss, 2009).

Accumulating evidence suggests that the therapeutic efficacy of certain conventional chemotherapies, particularly anthracyclines, relies not only on direct cytotoxicity but also on restoring anti-cancer immune responses (Galluzzi et al. 2015; Casares et al. 2005). Our data show that repurposing DXR as a targeted therapy inhibits expression of multiple immune checkpoints on the cells responsible for therapy resistance and relapse. However, clinical doses induce oncogenic resistance mechanisms, reversing this effect. Although we used TIM-3 here only as a marker to distinguish LSCs from HSPCs in AML patients, TIM-3 also serves as an immune checkpoint, which plays a role in immune escape (Anderson, 2014; Anderson et al. 2016). Similarly, PD-L1 expression indicates stemness and resistance to therapy in multiple cancers (Hsu et al. 2018; Malta et al. 2018). CD24 is widely used as a cancer stem cell marker and selectively suppresses immune responses to damage (Jinesh et al. 2017; Chen et al. 2009). While multiple immune checkpoints were suppressed with low-dose DXR, this reduction was reversed at the typical clinical doses. Our pre-clinical and early clinical data indicate that Akt-activated β-catenin could serve as a biomarker indicating patients who might benefit from low-dose anthracycline therapy. Our finding that β-catenin binds multiple immune checkpoints indicates that the Wnt pathway may have a role in stem cells far beyond its well-known role in self-renewal, particularly in protecting stem cells from the immune system. This finding opens up a possibility of using low dose DXR to prime treatment-resistant cancer (stem) cells prior to subsequentanti-immune-checkpoint treatment.

REFERENCES

The following references, to the extent that they provide exemplary procedural or other details supplementary to those set forth herein, are specifically incorporated herein by reference.

1 Kuttesch, J. F., Jr. Multidrug resistance in pediatric oncology. *Invest New Drugs* 14, 55-67 (1996).
2 Greaves, M. & Maley, C. C. Clonal evolution in cancer. *Nature* 481, 306-313 (2012).
3 Kreso, A. & Dick, J. E. Evolution of the cancer stem cell model. *Cell Stem Cell* 14, 275-291 (2014).
4 Dick, J. E. Stem cell concepts renew cancer research. *Blood* 112, 4793-4807 (2008).
Eppert, K. et al. Stem cell gene expression programs influence clinical outcome in human leukemia. *Nat Med* 17, 1086-1093 (2011).
6 Greaves, M. Darwinian medicine: a case for cancer. *Nat Rev Cancer* 7, 213-221 (2007).
7 Greaves, M. Cancer stem cells renew their impact. *Nat Med* 17, 1046-1048 (2011).
8 Ding, L. et al. Clonal evolution in relapsed acute myeloid leukaemia revealed by whole-genome sequencing. *Nature* 481, 506-510 (2012).
9 Hanahan, D. & Weinberg, R. A. Hallmarks of cancer: the next generation. *Cell* 144, 646-674 (2011).
Holohan, C., Van Schaeybroeck, S., Longley, D. B. & Johnston, P. G. Cancer drug resistance: an evolving paradigm. *Nat Rev Cancer* 13, 714-726 (2013).
11 Cleary, M. L. Regulating the leukemia stem cell. Best practice & research. *Clinical haematology* 22, 483-487 (2009).
12 Peng, W. et al. Loss of PTEN Promotes Resistance to T Cell-Mediated Immunotherapy. *Cancer discovery* 6, 202-216 (2016).
13 Fruman, D. A. et al. The PI3K Pathway in Human Disease. *Cell* 170, 605-635 (2017).
14 Ciraolo, E., Morello, F. & Hirsch, E. Present and future of PI3K pathway inhibition in cancer: perspectives and limitations. *Current medicinal chemistry* 18, 2674-2685 (2011).
Cully, M., You, H., Levine, A. J. & Mak, T. W. Beyond PTEN mutations: the PI3K pathway as an integrator of multiple inputs during tumorigenesis. *Nat Rev Cancer* 6, 184-192 (2006).
16 Fruman, D. A. & Rommel, C. PI3K and cancer: lessons, challenges and opportunities. *Nature reviews. Drug discovery* 13, 140-156 (2014).
17 Hennessy, B. T., Smith, D. L., Ram, P. T., Lu, Y. & Mills, G. B. Exploiting the PI3K/AKT pathway for cancer drug discovery. *Nature reviews. Drug discovery* 4, 988-1004 (2005).
18 Koren, S. & Bentires-Alj, M. Tackling Resistance to PI3K Inhibition by Targeting the Epigenome. *Cancer Cell* 31, 616-618 (2017).
19 Thorpe, L. M., Yuzugullu, H. & Zhao, J. J. PI3K in cancer: divergent roles of isoforms, modes of activation and therapeutic targeting. *Nat Rev Cancer* 15, 7-24 (2014).
Gutierrez, A. et al. High frequency of PTEN, PI3K, and AKT abnormalities in T-cell acute lymphoblastic leukemia. *Blood* 114, 647-650 (2009).
21 Hogan, L. E. et al. Integrated genomic analysis of relapsed childhood acute lymphoblastic leukemia reveals therapeutic strategies. *Blood* 118, 5218-5226 (2011).
22 Bhatla, T. et al. Epigenetic reprogramming reverses the relapse-specific gene expression signature and restores chemosensitivity in childhood B-lymphoblastic leukemia. *Blood* 119, 5201-5210 (2012).
23 Bolouri, H. et al. The molecular landscape of pediatric acute myeloid leukemia reveals recurrent structural alterations and age-specific mutational interactions. *Nat Med* 24, 103-112 (2018).
24 Griffiths, E. A. et al. Acute myeloid leukemia is characterized by Wnt pathway inhibitor promoter hypermethylation. *Leukemia & lymphoma* 51, 1711-1719 (2010).
Dandekar, S. et al. Wnt inhibition leads to improved chemosensitivity in paediatric acute lymphoblastic leukaemia. *Br J Haematol* 167, 87-99 (2014).
26 Kandoth, C. et al. Mutational landscape and significance across 12 major cancer types. *Nature* 502, 333-339 (2013).
27 Huang, J., Nguyen-McCarty, M., Hexner, E. O., Danet-Desnoyers, G. & Klein, P. S. Maintenance of hematopoietic stem cells through regulation of Wnt and mTOR pathways. *Nat Med* 18, 1778-1785 (2012).
28 Korkaya, H. et al. Regulation of mammary stem/progenitor cells by PTEN/Akt/beta-catenin signaling. *PLoS Biol* 7, e1000121 (2009).
29 Huang, J. et al. Pivotal role for glycogen synthase kinase-3 in hematopoietic stem cell homeostasis in mice. *J Clin Invest* 119, 3519-3529 (2009).
Conley, S. J. et al. Antiangiogenic agents increase breast cancer stem cells via the generation of tumor hypoxia. *Proc Natl Acad Sci USA* 109, 2784-2789 (2012).
31 He, X. C. et al. PTEN-deficient intestinal stem cells initiate intestinal polyposis. *Nat Genet* 39, 189-198 (2007).
32 Perry, J. M. et al. Cooperation between both Wnt/{beta}-catenin and PTEN/PI3K/Akt signaling promotes primitive hematopoietic stem cell self-renewal and expansion. *Genes Dev* 25, 1928-1942 (2011).

33 Knapp, D. J. et al. Distinct signaling programs control human hematopoietic stem cell survival and proliferation. *Blood* 129, 307-318 (2017).

34 Shlush, L. I. et al. Identification of pre-leukaemic haematopoietic stem cells in acute leukaemia. *Nature* 506, 328-333 (2014).

Reya, T., Morrison, S. J., Clarke, M. F. & Weissman, I. L. Stem cells, cancer, and cancer stem cells. Nature 414, 105-111 (2001).

36 Nguyen, L. V., Vanner, R., Dirks, P. & Eaves, C. J. Cancer stem cells: an evolving concept. *Nat Rev Cancer* 12, 133-143 (2012).

37 Clevers, H. The cancer stem cell: premises, promises and challenges. *Nat Med* 17, 313-319 (2011).

38 Zhou, H. et al. Combined inhibition of beta-catenin and Bcr-Abl synergistically targets tyrosine kinase inhibitor-resistant blast crisis chronic myeloid leukemia blasts and progenitors in vitro and in vivo. *Leukemia* (2017).

39 Kurtova, A. V. et al. Blocking PGE-induced tumour repopulation abrogates bladder cancer chemoresistance. *Nature* (2014).

Heidel, F. H. et al. Genetic and pharmacologic inhibition of beta-catenin targets imatinib-resistant leukemia stem cells in CML. *Cell Stem Cell* 10, 412-424 (2012).

41 Zhao, C. et al. Loss of beta-catenin impairs the renewal of normal and CML stem cells in vivo. *Cancer Cell* 12, 528-541 (2007).

42 Toska, E. et al. PI3K pathway regulates ER-dependent transcription in breast cancer through the epigenetic regulator KMT2D. *Science* 355, 1324-1330 (2017).

43 Tenbaum, S. P. et al. beta-catenin confers resistance to PI3K and AKT inhibitors and subverts FOXO3a to promote metastasis in colon cancer. *Nat Med* 18, 892-901 (2012).

44 Kaveri, D. et al. beta-Catenin activation synergizes with Pten loss and Myc overexpression in Notch-independent T-ALL. *Blood* 122, 694-704 (2013).

Guo, W. et al. Multi-genetic events collaboratively contribute to Pten-null leukaemia stem-cell formation. *Nature* 453, 529-533 (2008).

46 Roderick, J. E. et al. c-Myc inhibition prevents leukemia initiation in mice and impairs the growth of relapsed and induction failure pediatric T-ALL cells. *Blood* 123, 1040-1050 (2014).

47 Schubert, S. et al. Targeting the MYC and PI3K Pathways Eliminates Leukemia-Initiating Cells in T-cell Acute Lymphoblastic Leukemia. *Cancer Res* 74, 7048-7059 (2014).

48 Dail, M. et al. Loss of oncogenic Notch1 with resistance to a PI3K inhibitor in T-cell leukaemia. *Nature* 513, 512-516 (2014).

49 Huang, W., Chang, H. Y., Fei, T., Wu, H. & Chen, Y. G. GSK3 beta mediates suppression of cyclin D2 expression by tumor suppressor PTEN. *Oncogene* 26, 2471-2482 (2007).

50 Lechman, E. R. et al. Attenuation of miR-126 activity expands HSC in vivo without exhaustion. *Cell Stem Cell* 11, 799-811 (2012).

51 Xu, C. et al. beta-Catenin/POU5F1/SOX2 transcription factor complex mediates IGF-I receptor signaling and predicts poor prognosis in lung adenocarcinoma. *Cancer Res* 73, 3181-3189 (2013).

52 Cancer Genome Atlas Research, N. et al. Integrated genomic characterization of endometrial carcinoma. *Nature* 497, 67-73 (2013).

53 Guezguez, B. et al. GSK3 Deficiencies in Hematopoietic Stem Cells Initiate Pre-neoplastic State that Is Predictive of Clinical Outcomes of Human Acute Leukemia. *Cancer Cell* 29, 61-74 (2016).

54 Al-Dhfyan, A., Alhoshani, A. & Korashy, H. M. Aryl hydrocarbon receptor/cytochrome P450 1A1 pathway mediates breast cancer stem cells expansion through PTEN inhibition and beta-Catenin and Akt activation. *Mol Cancer* 16, 14 (2017).

55 Brown, J. B. et al. Epithelial phosphatidylinositol-3-kinase signaling is required for beta-catenin activation and host defense against *Citrobacter rodentium* infection. *Infect Immun* 79, 1863-1872 (2011).

56 Lee, G. et al. Phosphoinositide 3-kinase signaling mediates beta-catenin activation in intestinal epithelial stem and progenitor cells in colitis. *Gastroenterology* 139, 869-881, 881 e861-869 (2010).

57 Sharma, P., Hu-Lieskovan, S., Wargo, J. A. & Ribas, A. Primary, Adaptive, and Acquired Resistance to Cancer Immunotherapy. *Cell* 168, 707-723 (2017).

58 Spranger, S., Bao, R. & Gajewski, T. F. Melanoma-intrinsic beta-catenin signalling prevents anti-tumour immunity. *Nature* 523, 231-235 (2015).

59 Spranger, S. & Gajewski, T. F. Impact of oncogenic pathways on evasion of antitumour immune responses. *Nat Rev Cancer* 18, 139-147 (2018).

60 Galluzzi, L., Buque, A., Kepp, O., Zitvogel, L. & Kroemer, G. Immunological Effects of Conventional Chemotherapy and Targeted Anticancer Agents. *Cancer Cell* 28, 690-714 (2015).

61 Casares, N. et al. Caspase-dependent immunogenicity of doxorubicin-induced tumor cell death. *J Exp Med* 202, 1691-1701 (2005).

62 Rabbani, A., Finn, R. M. & Ausio, J. The anthracycline antibiotics: antitumor drugs that alter chromatin structure. *Bioessays* 27, 50-56 (2005).

63 Gewirtz, D. A. A critical evaluation of the mechanisms of action proposed for the antitumor effects of the anthracycline antibiotics adriamycin and daunorubicin. *Biochem Pharmacol* 57, 727-741 (1999).

64 Gothert, J. R. et al. In vivo fate-tracing studies using the Scl stem cell enhancer: embryonic hematopoietic stem cells significantly contribute to adult hematopoiesis. *Blood* 105, 2724-2732 (2005).

65 Barker, N. & Clevers, H. Catenins, Wnt signaling and cancer. *Bioessays* 22, 961-965 (2000).

66 Hsu, J. M. et al. STT3-dependent PD-L1 accumulation on cancer stem cells promotes immune evasion. *Nature communications* 9, 1908 (2018).

67 Malta, T. M. et al. Machine Learning Identifies Stemness Features Associated with Oncogenic Dedifferentiation. *Cell* 173, 338-354 e315 (2018).

68 Jinesh, G. G., Manyam, G. C., Mmeje, C. O., Baggerly, K. A. & Kamat, A. M. Surface PD-L1, E-cadherin, CD24, and VEGFR2 as markers of epithelial cancer stem cells associated with rapid tumorigenesis. *Scientific reports* 7, 9602 (2017).

69 Chen, G. Y., Tang, J., Zheng, P. & Liu, Y. CD24 and Siglec-10 selectively repress tissue damage-induced immune responses. *Science* 323, 1722-1725 (2009).

70 Tran, T. H. et al. Long circulating self-assembled nanoparticles from cholesterol-containing brush-like block copolymers for improved drug delivery to tumors. *Biomacromolecules* 15, 4363-4375 (2014).

71 Hong, D. et al. Initiating and cancer-propagating cells in TEL-AML1-associated childhood leukemia. *Science* 319, 336-339 (2008).

72 Castor, A. et al. Distinct patterns of hematopoietic stem cell involvement in acute lymphoblastic leukemia. *Nat Med* 11, 630-637 (2005).

73 Kong, Y. et al. CD34+CD38+CD19+ as well as CD34+CD38-CD19+ cells are leukemia-initiating cells with self-renewal capacity in human B-precursor ALL. *Leukemia* 22, 1207-1213 (2008).

74 Wilson, K. et al. Flow minimal residual disease monitoring of candidate leukemic stem cells defined by the immunophenotype, CD34+CD38lowCD19+ in B-lineage childhood acute lymphoblastic leukemia. *Haematologica* 95, 679-683 (2010).

75 Eguchi, M., Eguchi-Ishimae, M. & Ishii, E. [Recent progress in leukemic stem cell research for childhood leukemia]. *Rinsho Ketsueki* 56, 1871-1881 (2015).

76 Kikushige, Y. et al. TIM-3 is a promising target to selectively kill acute myeloid leukemia stem cells. *Cell Stem Cell* 7, 708-717 (2010).

77 Jan, M. et al. Prospective separation of normal and leukemic stem cells based on differential expression of TIM3, a human acute myeloid leukemia stem cell marker. *Proc Natl Acad Sci USA* 108, 5009-5014 (2011).

78 Weinberg, R. A. *The biology of cancer*. Second edition. edn, (2014).

79 Nitiss, J. L. Targeting DNA topoisomerase II in cancer chemotherapy. *Nat Rev Cancer* 9, 338-350 (2009).

80 Anderson, A. C. Tim-3: an emerging target in the cancer immunotherapy landscape. *Cancer Immunol Res* 2, 393-398 (2014).

81 Anderson, A. C., Joller, N. & Kuchroo, V. K. Lag-3, Tim-3, and TIGIT: Co-inhibitory Receptors with Specialized Functions in Immune Regulation. *Immunity* 44, 989-1004 (2016).

82 Lesche, R. et al. Cre/loxP-mediated inactivation of the murine Pten tumor suppressor gene. *Genesis* 32, 148-149 (2002).

83 Harada, N. et al. Intestinal polyposis in mice with a dominant stable mutation of the beta-catenin gene. *Embo J* 18, 5931-5942 (1999).

84 Hu, Y. & Smyth, G. K. ELDA: extreme limiting dilution analysis for comparing depleted and enriched populations in stem cell and other assays. *Journal of immunological methods* 347, 70-78 (2009).

91 Freireich, E. J., Gehan, E. A., Rall, D. P., Schmidt, L. H. & Skipper, H. E. Quantitative comparison of toxicity of anticancer agents in mouse, rat, hamster, dog, monkey, and man. *Cancer chemotherapy reports. Part 1* 50, 219-244 (1966).

92 Kim, D. et al. TopHat2: accurate alignment of transcriptomes in the presence of insertions, deletions and gene fusions. *Genome Biol* 14, R36 (2013).

93 Anders, S., Pyl, P. T. & Huber, W. HTSeq—a Python framework to work with high-throughput sequencing data. *Bioinformatics* 31, 166-169 (2015).

94 Robinson, M. D., McCarthy, D. J. & Smyth, G. K. edgeR: a Bioconductor package for differential expression analysis of digital gene expression data. *Bioinformatics* 26, 139-140 (2010).

95 Miao, Y. et al. Adaptive Immune Resistance Emerges from Tumor-Initiating Stem Cells. *Cell* 177, 1172-1186 e1114, doi:10.1016/j.cell.2019.03.025 (2019).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for treating or ameliorating the effects of a cancer in a human subject comprising administering to the subject a first agent, which is daunorubicin or pharmaceutically acceptable salt thereof, and a therapeutically effective amount of a second agent, which is a chemotherapeutic, wherein daunorubicin is administered at 6.75 mg/m$^2$ daily, for 5 consecutive days.

2. The method according to claim 1, wherein the second agent is selected from nelarabine, dexamethasone, and combinations thereof.

3. The method according to claim 1, wherein the first and second agents are co-administered.

4. The method according to claim 1, wherein the first agent is administered prior to the second agent.

5. The method according to claim 1, wherein the second agent is administered prior to the first agent.

6. The method according to claim 1, wherein the administration of the first and second agents to the subject provides a synergistic effect in the treatment of the cancer.

7. The method according to claim 1, wherein the cancer is selected from the group consisting of bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, multiple myeloma, neuroblastoma, neuroendocrine cancer, ovarian cancer, pancreatic cancer, prostate cancer, rectal cancer, renal cell carcinoma, rhabdoid cancer, sarcomas, and urinary track cancer.

8. The method according to claim 1, wherein the cancer is selected from the group consisting of acute myeloid leukemia (AML), chronic myeloid leukemia (CML), acute lymphocytic leukemia (ALL), and chronic lymphocytic leukemia (CLL).

9. The method according to claim 1, wherein the cancer in the subject is relapsed or refractory.

10. The method according to claim 1, wherein the cancer in the subject is chemoresistant.

* * * * *